United States Patent
Bandarage et al.

(10) Patent No.: US 7,858,790 B2
(45) Date of Patent: Dec. 28, 2010

(54) MODULATORS OF MUSCARINIC RECEPTORS

(75) Inventors: Upul K. Bandarage, Lexington, MA (US); Jinwang Xu, Framingham, MA (US); Robert J. Davies, Somerville, MA (US); Paul S. Charifson, Framingham, MA (US); Rieko Arimoto, Tewksbury, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 11/823,762

(22) Filed: Jun. 28, 2007

(65) Prior Publication Data

US 2008/0033002 A1 Feb. 7, 2008

Related U.S. Application Data

(60) Provisional application No. 60/817,385, filed on Jun. 29, 2006.

(51) Int. Cl.
*C07D 471/00* (2006.01)
(52) U.S. Cl. ....................................................... 546/18
(58) Field of Classification Search ................... 546/18; 514/278
See application file for complete search history.

(56) References Cited

U.S. PATENT DOCUMENTS

| | | | |
|---|---|---|---|
| 3,654,287 A | 4/1972 | Dykstra | |
| 3,666,764 A * | 5/1972 | Campbell et al. | 546/17 |
| 3,959,475 A | 5/1976 | Bauer et al. | |
| 3,962,259 A | 6/1976 | Bauer et al. | |
| 4,233,307 A | 11/1980 | Ono et al. | |
| 4,349,549 A | 9/1982 | Roszkowski et al. | |
| 4,558,049 A | 12/1985 | Bernardi et al. | |
| 5,091,387 A | 2/1992 | Evans et al. | |
| 5,219,860 A * | 6/1993 | Chambers et al. | 514/278 |
| 5,536,716 A | 7/1996 | Chen et al. | |
| 5,576,321 A | 11/1996 | Krushinski, Jr. et al. | |
| 5,578,593 A * | 11/1996 | Chen et al. | 514/212.02 |
| 5,614,523 A | 3/1997 | Audia et al. | |
| 5,627,196 A | 5/1997 | Audia et al. | |
| 5,652,235 A | 7/1997 | Chen et al. | |
| 5,658,921 A | 8/1997 | Perregaard et al. | |
| 5,741,789 A | 4/1998 | Hibschman et al. | |
| 5,789,402 A | 8/1998 | Audia et al. | |
| 5,817,679 A | 10/1998 | Shen et al. | |
| 5,885,999 A | 3/1999 | Elliott et al. | |
| 6,013,652 A | 1/2000 | Maccoss et al. | |
| 6,130,217 A | 10/2000 | Arnold et al. | |
| 6,166,040 A | 12/2000 | Fairhurst et al. | |
| 6,326,372 B1 | 12/2001 | Evans et al. | |
| 6,326,375 B1 | 12/2001 | Fukami et al. | |
| 6,436,962 B1 | 8/2002 | Hoffman et al. | |
| 6,566,367 B2 | 5/2003 | Bakthavatchalam et al. | |
| 6,720,324 B2 | 4/2004 | Marzabadi et al. | |
| 6,828,440 B2 | 12/2004 | Goehring et al. | |
| 6,869,960 B2 | 3/2005 | Ito et al. | |
| 6,943,199 B2 | 9/2005 | De Lombaert et al. | |
| 7,045,527 B2 | 5/2006 | Chen et al. | |
| 7,205,417 B2 | 4/2007 | Fukami et al. | |
| 2002/0188124 A1 | 12/2002 | Fukami et al. | |
| 2003/0036652 A1 | 2/2003 | Bakthavatchalam et al. | |
| 2003/0158219 A1 | 8/2003 | Ito et al. | |
| 2004/0054177 A1 | 3/2004 | Otake et al. | |
| 2004/0072847 A1 | 4/2004 | Bakthavatchalam et al. | |
| 2004/0122074 A1 | 6/2004 | Dow et al. | |
| 2004/0142956 A1 | 7/2004 | Chen et al. | |
| 2004/0204397 A1 | 10/2004 | Chaturvedula et al. | |
| 2005/0033048 A1 | 2/2005 | Bakthavatchalam et al. | |
| 2005/0153998 A1 | 7/2005 | Ito et al. | |
| 2005/0176703 A1 | 8/2005 | Gabriel et al. | |
| 2005/0215576 A1 | 9/2005 | Degnan et al. | |
| 2005/0250814 A1 | 11/2005 | Zhou et al. | |
| 2005/0261332 A1 | 11/2005 | Distefano et al. | |
| 2006/0040964 A1 | 2/2006 | Bakthavatchalam et al. | |
| 2006/0058778 A1 | 3/2006 | Arcusa Villacampa et al. | |
| 2006/0111380 A1 | 5/2006 | Otake et al. | |
| 2006/0173027 A1 | 8/2006 | Marzabadi et al. | |
| 2006/0183904 A1 | 8/2006 | Guo et al. | |
| 2006/0211722 A1 | 9/2006 | Jiao et al. | |
| 2006/0217372 A1 | 9/2006 | Blanco-Pillado et al. | |
| 2007/0254903 A1 | 11/2007 | Boatman et al. | |

FOREIGN PATENT DOCUMENTS

| | | |
|---|---|---|
| CN | 1535967 | 10/2004 |
| DE | 2444728 A1 | 4/1975 |
| DE | 3342164 | 11/1983 |
| DE | 3433327 | 3/1985 |

(Continued)

OTHER PUBLICATIONS

Bymaster et al Drug Development Research 1997, 40, 158-170.*

(Continued)

*Primary Examiner*—Rita J Desai
*Assistant Examiner*—John Mabry
(74) *Attorney, Agent, or Firm*—Honigman Miller Schwartz and Cohn LLP; Christopher C. Forbes; Jonathan P. O'Brien

(57) ABSTRACT

The present invention relates to modulators of muscarinic receptors. The present invention also provides compositions comprising such modulators, and methods therewith for treating muscarinic receptor mediated diseases.

29 Claims, No Drawings

FOREIGN PATENT DOCUMENTS

| | | |
|---|---|---|
| EP | 0065864 | 12/1982 |
| EP | 0070171 | 1/1983 |
| EP | 0128886 | 12/1984 |
| EP | 0414289 A1 | 2/1991 |
| EP | 0 445 974 | 9/1991 |
| EP | 0444945 A2 | 9/1991 |
| EP | 0486280 A2 | 5/1992 |
| EP | 0518805 | 12/1992 |
| EP | 0533243 | 3/1993 |
| EP | 0615977 | 9/1994 |
| EP | 0722941 | 7/1996 |
| EP | 1 415 986 | 5/2004 |
| GB | 1575800 | 10/1980 |
| GB | 2131021 | 11/1983 |
| GB | 2308064 A | 6/1997 |
| GB | 2355264 | 9/2000 |
| GB | 2355456 | 9/2000 |
| JP | 59059685 | 4/1984 |
| JP | 2001/278886 | 10/2001 |
| JP | 2002/316987 | 10/2002 |
| WO | WO 94/19367 | 9/1994 |
| WO | WO 94/22846 | 10/1994 |
| WO | WO 95/09631 * | 4/1995 |
| WO | WO 9511029 | 4/1995 |
| WO | WO 95/14025 | 5/1995 |
| WO | WO 9528389 | 10/1995 |
| WO | WO 9741878 | 11/1997 |
| WO | WO 9741879 | 11/1997 |
| WO | WO 9906434 | 2/1999 |
| WO | WO 9932489 | 7/1999 |
| WO | WO 99/64002 | 12/1999 |
| WO | WO 0006146 | 2/2000 |
| WO | WO0006153 A1 | 2/2000 |
| WO | WO 0006545 | 2/2000 |
| WO | WO 0038720 | 7/2000 |
| WO | WO 01/02386 | 1/2001 |
| WO | WO-01-22919 | 4/2001 |
| WO | WO 01/29027 | 4/2001 |
| WO | WO 0122919 | 4/2001 |
| WO | WO 0145707 | 6/2001 |
| WO | WO 0164213 A1 | 9/2001 |
| WO | WO 02/48152 | 6/2002 |
| WO | WO 02/070511 * | 9/2002 |
| WO | WO 02/085354 * | 10/2002 |
| WO | WO 02094825 | 11/2002 |
| WO | WO02094825 A1 | 11/2002 |
| WO | WO 03/014083 | 2/2003 |
| WO | WO 03/037271 | 5/2003 |
| WO | WO 03/064425 | 8/2003 |
| WO | WO 03/095427 | 11/2003 |
| WO | WO 03/104236 | 12/2003 |
| WO | WO 03106457 | 12/2003 |
| WO | WO 2004004714 | 1/2004 |
| WO | WO2004010942 A2 | 2/2004 |
| WO | WO2004010943 A2 | 2/2004 |
| WO | WO2004011427 A2 | 2/2004 |
| WO | WO 2004/028459 | 4/2004 |
| WO | WO 2004/050652 | 6/2004 |
| WO | WO 2004/074273 | 9/2004 |
| WO | WO 2004/089307 | 10/2004 |
| WO | WO 2005/016913 | 2/2005 |
| WO | WO 2005/063254 | 7/2005 |
| WO | WO 2005 063745 | 7/2005 |
| WO | WO 2005/065779 | 7/2005 |
| WO | WO 2005/075484 | 8/2005 |
| WO | WO 2005/100360 | 10/2005 |
| WO | WO-2006-001958 | 1/2006 |
| WO | WO 2006/023852 | 3/2006 |
| WO | WO 2006/028239 | 3/2006 |
| WO | WO 2006/058303 | 6/2006 |
| WO | WO 2007/077122 | 7/2007 |

OTHER PUBLICATIONS

Custers, Franciscus G. J., et al., Vesamicol and some of its derivatives: Questionalbe ligands for selectively labeling acetylcholine transporters in rat brain, *European Journal of Pharmacology*, 338 (1997) 177-183.

De Laszlo, S.E., et al., A Nonpeptidic Agonist Ligand of the Human C5A Receptor: Synthesis, Binding Affinity Optimization and Functional Characterization, *Bioorganic & Medicinal Chemistry Letters*, vol. 7, No. 2, pp. 213-218, 1997.

Efange, S. M. N., et al., (+)-p-([$^{18}$F]Fluorobenzyl) Spirotrozamicol {(+)-[$^{18}$F]Spiro-FBT}: Synthesis and Biological Evaluation of a High-Affinity Ligand for the Vesicular Acetylcholine Transporter (VAChT), *Nuclear Medicine & Biology*, vol. 26. 26, pp. 189-192, 1999.

Malstrom, Rickard E., et al., Pharmacology of H 394/84, a dihydropyridine neuropeptide Y $Y_1$ receptor antagonist, in vivo, *European Journal of Pharmacology* 418 (2001) 95-104.

Morrow, Duane F., et al., Synthesis of Some New 17-Spiro-Substituted Steroids, *Journal of Medicinal Chemistry*, vol. 10, No. 2, Feb. 27, 1967.

Nargund, Ravi P., et al., Peptidomimetic Growth Hormone Secretagogues: Synthesis and Biological Activities of Analogs Varied at the Indole Nucleus of the Prototypical Spiropiperidine L-162,752, *Bioorganic & Medicinal Chemistry Letters*, vol. 6, No. 14, pp. 1731-1736, 1996.

Nargund, Ravi P., et al., Synthesis and Biological Activities of Camphor-Based Non-Peptide Growth Hormone Secretagogues, *Bioorganic & Medicinal Chemistry Letters*, vol. 6, No. 11, pp. 1265-1270, 1996.

Oprea, Tudor I., et al., Is There a Difference between Leads and Drugs? A Historical Perspective, *J. Chem. Inf. Comput. Sci*, 2001, 41. 1308-1315.

Pasternak, Alexander, et al., Potent, Orally Bioavailable Somatostatin Agonists: Good Absorption Achieved by Urea Backbone Cyclization, *Bioorganic & Medicinal Chemistry Letters* 9 (1999) 491-496.

Patchett, A. A., et al., The Synthesis of 17β-Amino-17α-(2'-carboxyethyl)androstane Lactams, Research Laboratories of Merck & Co., In., Rahway, New Jersey, Nov. 1962, vol. 27, pp. 3822-3828.

Pettibone, D. J., et al., Identification of an Orally Active, Nonpeptidyl Oxytocin Antagonist, *The Journal of Pharmacology and Experimental Therapeutics*, vol. 264, No. 1, 1993, pp. 308-314.

Takemoto, Toshiyasu, et at., Asymmetric synthesis of enantiomerically pure spiro[((2S)-hydroxy)indane-1,4' -piperidine], *Tetrahedron: Asymmetry*, 10 (1999) 1787-1793.

Tata, James R., et al., The Synthesis and Activity of Spiroindane Growth Hormone Secretagogues, *Bioorganic & Medicinal Chemistry Letters*, vol. 7, No. 6, pp. 663-668, 1997.

Williams, Peter D., et al., 1-(((7,7-Dimethyl-2(S)-(2(S)-amino-4-(methylsulfonyl)butyramido)bicycle[2.2.1]-heptan-1(S)-yl)methyl)sulfonyl)-4-(2-methylphenyl)piperazine (L-368,899): An Orally Bioavailable, Non-Peptide Oxytocin Antagonist with Potential Utility for Managing Preterm Labor, *J. Med. Chem.* 1994, 37, 555-571.

Abdel-Magid, A.F., et al., "Reductive Amination of Aldehydes and Ketones with Sodium Triacetoxyborohydride. Studies on Direct and Indirect Amination Procedures," *J. Org. Chem.*, 61, pp. 3849-3862 (1996).

Caulfield, M.P., et al., "Classification of Muscarinic Acetylcholine Receptors," International Union of Pharmacology. XVII, *Pharmacol. Rev.*, 50, pp. 279-290 (1998).

Caulfield, M.P., et al., "Muscarinic Receptors-Characterization, Coupling, and Function," *Pharmacol. Ther.*, 58, pp. 319-379 (1993).

Chambers, Mark S., et al, "Spiropiperdines as high-affinity, selective o' ligands," *Journal of Medicinal Chemistry* (1992), 35(11), 2033-9.

Chiavarelli, S., et al., Preparation of spirocyclic template 1,2,3,4-tetrahydrospiro [isoquinoline-4,4'-piperidine] compounds, *Gazzetta Chimica Italiana*, 1960, 90, 189; CN1535967.

Dhar, T.G., Murali, "Design and synthesis of a novel $\alpha_{1a}$ adrenoceptor-selective antagonists," Journal of Medicinal Chemistry (1999), 42 (23), 4778-4793.

Dooseop, Kim, et al., Discovery of human CCR5 antagonists containing hydantoins for the treatment of HIV-1 infection, Bioorganic and Medicinal Chemistry Letters, vol. 11, No. 24, Dec. 17, 2001, pp. 3099-3102, Elsevier Science Ltd.

Efange, Simon M.N., et al, "N-Hydroxyalkyl Derivatives of 3β-Phenyltropane and Methylspiro [1H-indoline-3,4'-piperdine]: Vesamicol Analogues with Affinity or Monaomine Transporters," J. Med. Chem. (1997) vol. 40, pp. 3905-3914.

Efange, Simon M.N., et al., "Spirovesamicols: Conformationally restricted analogs of 2-(4-Phenylpiperdino) cyclohexanol (Vesamicol, AH5183) as potential modulators of presynaptic cholinergic function," Journal of Medicinal Chemistry (1994), 37 (16), 2574-82.

Efange, Simon M.N., et al., Vesamicol Analogues as Sigma Ligands; Biochemical Pharmacology, vol. 49, No. 6 pp. 791-797, 1995.

Evans, Ben E., et al., "Orally active, nonpeptide oxytocin antagonists," Journal of Medicinal Chemistry (1992) 35(21), 3919-3927.

Felder, Christian C., et al., "Therapeutic Opportunities for Muscarinic Receptors in the Central Nervous System," J. Med., Chem., 43 (23), pp. 4333-4353 (2000).

Freireich, et al., "Quantitative Comparison of Toxicity of Anticancer Agents in Mouse, Rat, Hamster, Dog, Monkey and Man," Cancer Chemotherapy. Rep., 50: 219 (1966).

Hulme, E.C., et al., "Muscarinic Receptor Subtypes," Ann. Rev. Pharmacol Toxicol., 30, pp. 633-673 (1990).

International Search Report and Written Opinion of the International Searching Authority for International Application No. PCT/US2005/042967.

Matier, W.L., et al., "Novel Cyclizations and Ring-Opening Reactions of 3-Phenylidene Derivatives," Journal of Organic Chemistry, American Chemical Society, Eason, US, vol. 36, No. 5, 1971, pp. 650-654.

Moltzen, Ejner K., et al., o' Ligands with Subnanomolar affinity and preference for the o' bonding site, Journal of Medicinal Chemistry (1995), 38 (11), 2009-17.

PCT International Search Report for International Application No. PCT/US2006/049412.

Yang, Lihu, et al., "The design and synthesis of non-peptide somatostatin receptor agonists," Peptides for the New Millennium, Proceedings of the American Peptide Symposium, $16^{th}$, Minneapolis, MN, Jun. 26-Jul. 1, 1999 (2000), Meeting Date 1999, 250-252.

Yang, Lihu, et al., "Potent 3-spiropiperdine growth hormone secretagogues," Bioorganic & Medicinal Chemistry Letters 8 (1998) 107-112.

Bignan, G., "Preparation of 3-Spirocyclic Indolin-2-ones as Ligands for the ORL-1 Receptor", Bioorganic and Medicinal Chem. Lett, 15 (2005), pp. 5022-5026.

Butera, J., "Recent Approaches to the Treatment of Urinary Incontinence: A Survey of Patent Activity from 1995 to 1998", Expert Opinion on Therapeutic Patents, 8(8) (1998), pp. 1017-1035.

Reimann, E., "Synthese und pharmakologische Prüfung Homologer und hydroxylierter 3,4-Dihydro-1'-methylspiro [naphthalin-(2H),4'-piperidine]", Archiv. Der. Pharmazie, VCH Verlagsgesellschaft MBH, Weinheim, DE, 323 (1990), pp. 35-39.

* cited by examiner

MODULATORS OF MUSCARINIC RECEPTORS

CLAIM OF PRIORITY

This application hereby claims the benefit of U.S. provisional patent application Ser. No. 60/817,385, which was filed on Jun. 29, 2006, and is hereby incorporated by reference.

TECHNICAL FIELD OF THE INVENTION

The present invention relates to modulators of muscarinic receptors. The present invention also provides compositions comprising such modulators, and methods therewith for treating muscarinic receptor mediated diseases.

BACKGROUND OF THE INVENTION

The neurotransmitter acetylcholine binds to two types of cholinergic receptors: the ionotropic family of nicotinic receptors and the metabotropic family of muscarinic receptors. Muscarinic receptors belong to the large superfamily of plasma membrane-bound G protein coupled receptors (GPCRs). To date, five subtypes of muscarinic receptors ($M_1$-$M_5$) have been cloned and sequenced from a variety of species, and show a remarkably high degree of homology across species and receptor subtype. These $M_1$-$M_5$ muscarinic receptors are predominantly expressed within the parasympathetic nervous system which exerts excitatory and inhibitory control over the central and peripheral tissues and participate in a number of physiologic functions, including heart rate, arousal, cognition, sensory processing, and motor control.

Muscarinic agonists such as muscarine and pilocarpine, and antagonists, such as atropine have been known for over a century, but little progress has been made in the discovery of receptor subtype-selective compounds, thereby making it difficult to assign specific functions to the individual receptors. See, e.g., DeLapp, N. et al., "Therapeutic Opportunities for Muscarinic Receptors in the Central Nervous System," J. Med. Chem., 43(23), pp. 4333-4353 (2000); Hulme, E. C. et al., "Muscarinic Receptor Subtypes," Ann. Rev. Pharmacol. Toxicol., 30, pp. 633-673 (1990); Caulfield, M. P. et al., "Muscarinic Receptors-Characterization, Coupling, and Function," Pharmacol. Ther., 58, pp. 319-379 (1993); Caulfield, M. P. et al., International Union of Pharmacology. XVII. "Classification of Muscarinic Acetylcholine Receptors," Pharmacol. Rev., 50, pp. 279-290 (1998), the disclosures of which are incorporated herein by reference.

The Muscarinic family of receptors is the target of a large number of pharmacological agents used for various diseases, including leading drugs for COPD, asthma, urinary incontinence, glaucoma, Alzheimer's (AchE inhibitors). Despite the large therapeutic value of this family, cholinergic drugs are limited by the lack of selectivity of these agents, with significant activation of the parasympathetic autonomous system and elevated incidence of adverse effects. The molecular cloning of the muscarinic receptors and the identification of the physiological role of specific isoforms using knock-out mice, has recently delineated novel opportunities for selective muscarinic ligands, and has helped to define the selectivity profile that is required for enhanced efficacy and reduced side effects.

There is a need for modulators of muscarinic receptors $M_1$-$M_5$. There is also a need for methods for treating muscarinic receptor-mediated diseases.

There is also a need for modulators of muscarinic receptors that are selective as to subtypes $M_1$-$M_5$.

SUMMARY OF THE INVENTION

The present invention provides methods of modulating the activity of a muscarinic receptor (e.g., $M_1$, $M_2$, $M_3$, $M_4$, $M_5$, or combinations thereof) using compounds of formula I:

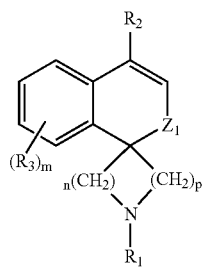

I or a pharmaceutically acceptable salt thereof, wherein $Z_1$, $R_1$, $R_2$, $R_3$, m, n and p are described below.

DETAILED DESCRIPTION

I. Definitions

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "muscarinic receptor," without a prefix specifying the receptor subtype, refers to one or more of the five receptor subtypes $M_1$-$M_5$.

The term "modulating" as used herein means increasing or decreasing, e.g. activity, by a measurable amount. Compounds that modulate muscarinic activity by increasing the activity of the muscarinic receptors are called agonists. Compounds that modulate muscarinic activity by decreasing the activity of the muscarinic receptors are called antagonists. An agonist interacts with a muscarinic receptor to increase the ability of the receptor to transduce an intracellular signal in response to endogenous ligand binding. An antagonist interacts with a muscarinic receptor and competes with the endogenous ligand(s) or substrate(s) for binding site(s) on the receptor to decrease the ability of the receptor to transduce an intracellular signal in response to endogenous ligand binding.

The phrase "treating or reducing the severity of a muscarinic receptor mediated disease" refers both to treatments for diseases that are directly caused by muscarinic activities and alleviation of symptoms of diseases not directly caused by muscarinic activities. Examples of diseases whose symptoms may be affected by muscarinic activity include, but are not limited to, CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, Parkinson's disease, peripheral disorders such as reduction of intra ocular pressure in Glaucoma and treatment of dry eyes and dry mouth including Sjögren's Syndrome, bradhycardia, gastric acid secretion, asthma, GI disturbances and wound healing.

As described herein, compounds of the invention may optionally be substituted with one or more substituents, such as are illustrated generally above, or as exemplified by particular classes, subclasses, and species of the invention.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-8 (e.g., 1-6 or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-$SO_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as halo, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-$SO_2$—, cycloaliphatic-$SO_2$—, or aryl-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-$SO_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-6 or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-$SO_2$—, aliphaticamino-$SO_2$—, or cycloaliphatic-$SO_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refers to an amido group such as —N($R^X$)—C(O)—$R^Y$ or —C(O)—N($R^X$)$_2$, when used terminally, and —C(O)—N($R^X$)— or —N($R^X$)—C(O)—when used internally, wherein $R^X$ and $R^Y$ are defined below. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —$NR^XR^Y$ wherein each of $R^X$ and $R^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic) aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic) carbonyl, each of which being defined herein and being optionally substituted. Examples of amino groups include alkylamino, dialkylamino, or arylamino. When the term "amino" is not the terminal group (e.g., alkylcarbonylamino), it is represented by —$NR^X$—. $R^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more C$_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic) carbonyl]; sulfonyl [e.g., aliphatic-SO$_2$— or amino-SO$_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl) aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy) alkyl)aryl; (((dialkyl)amino)alkyl)aryl; (nitroalkyl)aryl; (((alkylsulfonyl)amino)alkyl)aryl; ((heterocycloaliphatic) carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a C$_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a C$_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2] octyl, bicyclo[3.3.1]nonyl, bicyclo[3.3.2]decyl, bicyclo [2.2.2]octyl, adamantyl, azacycloalkyl, or ((aminocarbonyl)cycloalkyl)cycloalkyl. A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-dienyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl. A cycloalkyl or cycloalkenyl group can be optionally substituted with one or more substituents such as aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-SO$_2$— and aryl-SO$_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, "cyclic moiety" includes cycloaliphatic, heterocycloaliphatic, aryl, or heteroaryl, each of which has been defined previously.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b] thiopheneyl, 2-oxa-bicyclo[2.2.2]octyl, 1-aza-bicyclo[2.2.2] octyl, 3-aza-bicyclo[3.2.1]octyl, and 2,6-dioxa-tricyclo [3.3.1.0$^{3,7}$]nonyl. A monocyclic heterocycloalkyl group can be fused with a phenyl moiety such as tetrahydroisoquinoline. A "heterocycloalkenyl" group, as used herein, refers to a mono- or bicyclic (e.g., 5- to 10-membered mono- or bicyclic) non-aromatic ring structure having one or more double bonds, and wherein one or more of the ring atoms is a heteroatom (e.g., N, O, or S). Monocyclic and bicycloheteroaliphatics are numbered according to standard chemical nomenclature.

A heterocycloalkyl or heterocycloalkenyl group can be optionally substituted with one or more substituents such as aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic)carbonylamino, (aryl)carbonylamino, (araliphatic) carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic) carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1, 2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic) oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic) carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl) amino)heteroaryl]; (cyanoalkyl)heteroaryl; (alkoxy)heteroaryl; (sulfamoyl)heteroaryl [e.g., (aminosulfonyl) heteroaryl]; (sulfonyl)heteroaryl [e.g., (alkylsulfonyl) heteroaryl]; (hydroxyalkyl)heteroaryl; (alkoxyalkyl) heteroaryl; (hydroxy)heteroaryl; ((carboxy)alkyl)heteroaryl; (((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl, and (haloalkyl)heteroaryl [e.g., trihaloalkylheteroaryl].

A "heteroaraliphatic (such as a heteroalkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—$NR^XR^Y$ or —$NR^X$—CO—O—$R^Z$ wherein $R^X$ and $R^Y$ have been defined above and $R^Z$ can be aliphatic, aryl, araliphatic, heterocycloaliphatic, heteroaryl, or heteroaraliphatic.

As used herein, a "carboxy" group refers to —COOH, —COOR$^X$, —OC(O)H, —OC(O)R$^X$ when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfonamide" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—Rx when used terminally and —S(O)— when used internally, wherein R$^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$— when used internally, wherein Rx has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$— or the like.

As used herein, a "sulfoxy" group refers to —O—SO—R$^X$ or —SO—O—R$^X$, when used terminally and —O—S(O)— or —S(O)—O— when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, an "aminoalkyl" refers to the structure (R$^X$)$_2$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ have been defined above.

As used herein, a "guanidine" group refers to the structure —N=C(N(R$^X$R$^Y$))N(R$^X$R$^Y$) or —NR$^X$—C(=NR$^X$)NR$^X$R$^Y$ wherein R$^X$ and R$^Y$ have been defined above.

As used herein, the term "amidino" group refers to the structure —C=(NR$^X$)N(R$^X$R$^Y$) wherein R$^X$ and R$^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent to at the end of the substituent bound to the rest of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, "cyclic group" includes mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxabicyclo[2.2.2]octyl, 1-azabicyclo[2.2.2]octyl, 3-azabicyclo[3.2.1]octyl, and 2,6-dioxa-tricyclo[3.3.1.0$^{3,7}$]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "aliphatic chain" refers to a branched or straight aliphatic group (e.g., alkyl groups, alkenyl groups, or alkynyl groups). A straight aliphatic chain has the structure —[CH$_2$]$_v$—, where v is 1-6. A branched aliphatic chain is a straight aliphatic chain that is substituted with one or more aliphatic groups. A branched aliphatic chain has the structure —[CHQ]$_v$- or —[CQQ]$_v$- where Q is hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables in formulae (I, Ia, and Ib), e.g., R$_1$, R$_2$, and R$_3$, and other variables contained therein encompass specific groups, such as alkyl and aryl. Unless otherwise noted, each of the specific groups for the variables R$_1$, R$_2$, and $R_3$, and other variables contained therein can be optionally substituted with one or more substituents described herein. Each substituent of a specific group is further optionally substituted with one to three of halo, cyano, oxo, alkoxy, hydroxy, amino, nitro, aryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, New York, 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, (Z) and (E) conformational isomers, and tautomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

II. Compounds

A. Generic Compounds

The present invention provides methods of modulating the activity of a muscarinic receptor comprising the step of contacting said receptor with a compound of formula I:

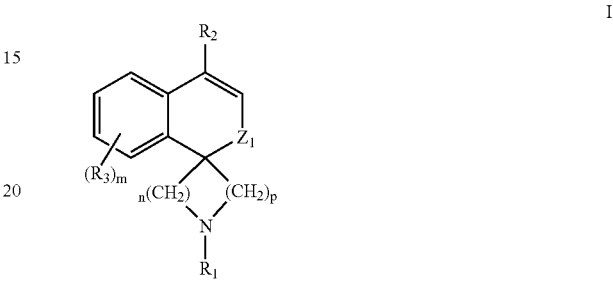

I or a pharmaceutically acceptable salt thereof.

$R_1$ is an optionally substituted aliphatic, an optionally substituted cycloaliphatic, or an optionally substituted heterocycloaliphatic.

$R_2$ is —$Z^B R_5$, wherein each $Z^B$ is independently a bond or an optionally substituted branched or straight $C_{1-6}$ aliphatic chain wherein up to two carbon units of $Z^B$ are optionally and independently replaced by —C(O)—, —CS—, —C(O)NR$^B$—, —C(O)NR$^B$NR$^B$—, —C(O)O—, —OC(O)—, —NR$^B$C(O)O—, —O—, —NR$^B$CONR$^B$—, —OC(O)NR$^B$—, —NR$^B$NR$^B$—, —NR$^B$C(O)—, —S—, —SO—, —SO$_2$—, —NR$^B$—, —SO$_2$NR$^B$—, —NR$^B$SO$_2$—, or —NR$^B$SO$_2$NR$^B$—. Each $R_5$ is independently $R^A$, halo, —OH, —NH$_2$, —NO$_2$, —CN, or —OCF$_3$. Each $R^B$ is independently an optionally substituted aliphatic, an optionally substituted cycloaliphatic, an optionally substituted heterocycloaliphatic, an optionally substituted aryl, or an optionally substituted heteroaryl.

Each $R_3$ is independently —$Z^D R_8$, wherein each $Z^D$ is independently a bond or an optionally substituted branched or straight $C_{1-8}$ aliphatic chain wherein up to two carbon units of $Z^D$ are optionally and independently replaced by —C(O)—, —CS—, —C(O)NR$^D$—, —C(O)NR$^D$NR$^D$—, —OC(O)—, —C(O)O—, —NR$^D$C(O)O—, —O—, —NR$^D$C(O)NR$^D$—, —OC(O)NR$^D$—, —NR$^D$NR$^D$—, —NR$^D$C(O)—, —S—, —SO—, —SO$_2$—, —NR$^D$—, —SO$_2$NR$^D$—, —NR$^D$SO$_2$—, or —NR$^D$SO$_2$NR$^D$—. Each $R_8$ is independently $R^D$, halo, —OH, —CN, or —OCF$_3$. Each $R^D$ is independently hydrogen, an optionally substituted $C_{1-8}$ aliphatic group, an optionally substituted cycloaliphatic, an optionally substituted heterocycloaliphatic, an optionally substituted aryl, an optionally substituted heteroaryl.

$Z_1$ is a bond, —O—, —NR$_6$—, or —C(R$_6$)$_2$—, wherein each $R_6$ is independently —$Z^C R_7$, wherein each $Z^C$ is independently a bond or an optionally substituted branched or straight $C_{1-6}$ aliphatic chain wherein up to two carbon units of $Z^C$ are optionally and independently replaced by —C(O)—, —CS—, —C(O)NR$^C$—, —C(O)NR$^C$NR$^C$—, —C(O)O—, —OC(O)—, —NR$^C$C(O)O—, —O—, —NR$^C$C(O)NR$^C$—, —OC(O)NR$^C$—, —NR$^C$NR$^C$—, —NR$^C$C(O)—, —S—, —SO—, —SO$_2$—, —NR$^C$—, —SO$_2$NR$^C$—, —NR$^C$SO$_2$—, or —NR$^C$SO$_2$NR$^C$—. Each $R_7$ is independently $R^C$, halo, —OH, —NH$_2$, —NO$_2$, —CN, or —OCF$_3$. Each R$^C$ is independently hydrogen, an optionally substituted aliphatic, an optionally substituted cycloaliphatic, an optionally substituted heterocycloaliphatic, an optionally substituted aryl, or an optionally substituted heteroaryl.

m is 0-4.
n is 0-6.
p is 0-6; and
n+p is 2, 3, 4, 5, or 6.

B. Specific Compounds

1. Substituent R$_1$:

R$_1$ is hydrogen, an optionally substituted aliphatic, an optionally substituted cycloaliphatic, or an optionally substituted heterocycloaliphatic.

In some embodiments, R$_1$ is —Z$^A$R$_4$, wherein each Z$^A$ is independently a bond or an optionally substituted branched or straight C$_{1-2}$ aliphatic chain wherein up to two carbon units of Z$^A$ are optionally and independently replaced by —C(O)—, —CS—, —C(O)NR$^A$—, —C(O)NR$^A$NR$^A$—, —C(O)O—, —OC(O)—, —NR$^A$C(O)O—, —O—, —NR AC(O)NR$^A$—, —OC(O)NR$^A$—, —NR$^A$NR$^A$—, —NR$^A$C(O)—, —S—, —SO—, —SO$_2$—, —NR$^A$—, —SO$_2$NR$^A$—, —NR$^A$SO$_2$—, or —NR$^A$SO$_2$NR$^A$—. Each R$_4$ is independently R$^A$, halo, —OH, —NH$_2$, —NO$_2$, —CN, or —OCF$_3$. Each R$^A$ is independently hydrogen or an optionally substituted aliphatic, an optionally substituted cycloaliphatic, or an optionally substituted heterocycloaliphatic. However, in several embodiments, when Z$^A$ is a bond and R$_4$ is R$^A$, then R$^A$ is an optionally substituted aliphatic, an optionally substituted cycloaliphatic, or an optionally substituted heterocycloaliphatic.

In several embodiments, R$_1$ is an optionally substituted aliphatic. For example, R$_1$ is an alkyl, an alkenyl, or an alkynyl, each of which is optionally substituted. In several examples, R$_1$ is an optionally substituted C$_{1-12}$ aliphatic. In other embodiments, R$_1$ is an optionally substituted straight C$_{1-12}$ aliphatic. In several examples, R$_1$ is a methyl, ethyl, propyl, butyl, pentyl, hexyl, heptyl, or octyl, each of which is optionally substituted with 1-3 of halo or a cycloaliphatic, a heterocycloaliphatic, an alkylsulfanyl, an alkoxy, an amino, an acyl, or combinations thereof, each of which is optionally substituted. In other examples, R$_1$ is an optionally substituted branched C$_{1-12}$ aliphatic. In several examples, R$_1$ is isopropyl, 3,3-dimethylbutyl, 2,2-dimethylbutane, tert-butyl, 3-methylbutyl, butyl, 2-ethylbutyl, propyl, butan-3-one-yl, butan-2-one-yl, but-2-yn-yl, methoxyethyl, isopentyl, or 3,7-dimethyloctyl.

In several embodiments R$_1$ is an optionally substituted cycloaliphatic. For example, R$_1$ is a monocyclic cycloaliphatic or a bicyclic cycloaliphatic, each of which is optionally substituted. In other examples, R$_1$ is an optionally substituted 3-8 membered monocyclic cycloaliphatic. In additional examples, R$_1$ is cyclopropyl, cyclobutyl, cyclopentyl, cyclohexyl, cycloheptyl, or cyclooctyl, each of which is optionally substituted with 1-3 of halo, aliphatic, hydroxy, alkoxycarbonyl, cycloaliphatic, or combinations thereof. In several examples, R$_1$ is an optionally substituted 7-10 membered bicyclic cycloaliphatic. In several examples, R$_1$ is an optionally substituted 7-10 membered bicyclic cycloalkyl or an optionally substituted 7-10 membered bicyclic cycloalkenyl. For example, R$_1$ is bicyclo[2.1.1]hexane-yl, bicyclo [2.2.1]heptane-yl, bicyclo[2.2.2]octane-yl, bicyclo[3.1.1] heptane-yl, bicyclo[3.2.1]octane-yl, or bicyclo[3.3.1] nonane-yl, each of which is optionally substituted with 1-3 of halo, aliphatic, hydroxy, amino, acyl, or combinations thereof. In other examples, R$_1$ is an optionally substituted bicyclo[2.1.1]hex-2-ene-yl, bicyclo[2.2.1]hept-2-ene-yl, or bicyclo[2.2.2]oct-2-ene-yl, each of which optionally substituted with 1-3 of halo, aliphatic, hydroxy, amino, acyl, or combinations thereof.

In several embodiments, R$_1$ is an optionally substituted heterocycloaliphatic. For example, R$_1$ is a monocyclic heterocycloaliphatic or a bicyclic heterocycloaliphatic, each of which is optionally substituted. In other examples, R$_1$ is an optionally substituted 3-8 membered monocyclic heterocycloaliphatic having 1-3 heteroatoms selected from N, O, and S. In additional examples, R$_1$ is tetrahydrofuran-yl, tetrahydro-2H-thiopyran-yl, pyrrolidine-yl, imidazolidine-yl, 1,4-dioxane-yl, morpholine-yl, piperidine-yl, piperazine-yl, tetrahydro-2H-pyran-yl, pyrazolidine-yl, or thiomorpholine-yl, each of which is optionally substituted with 1-3 of halo, aminocarbonyl, alkoxycarbonyl, acyl, carboxy or combinations thereof. In other examples, R$_1$ is an optionally substituted 7-10 membered bicyclic heterocycloaliphatic having 1-2 heteroatoms selected from N, O, and S. In other examples, R$_1$ is an optionally substituted 7-10 membered bridged bicyclic heterocycloaliphatic, or R$_1$ is an optionally substituted 7-10 membered fused bicyclic heterocycloaliphatic. In other examples, R$_1$ is 8-azabicyclo[3.2.1]octane-yl, or azabicyclo [2.2.1]heptane-yl, each of which is optionally substituted.

In several alternative embodiments, R$_1$ is one selected from: cyclohexylmethyl; 3,3-dimethylbutyl; bicyclo[2.2.1] hept-5-en-2-yl; cyclohept-1-yl; bicyclo[2.2.1]heptane-2-yl; 1-ethoxycarbonylpiperidine-4-yl; 8-ethoxycarbonyl-8-azabicyclo[3.2.1]octane-3-yl; 3-methylbutyl; (tetrahydro-2H-pyran-4-yl)ethyl; 4-(methyl(sulfanyl))butyl; 3,7-dimethyl-7-methoxyoctyl; (tetrahydro-2H-thiopyran-4-yl)ethyl; cyclohexyl; cycloheptyl; cyclopentyl; (N,N-dimethylaminocarbonyl)piperidine-4-yl; N-acetylpiperidine-4-yl; 1-(cyclopropyl(carbonyl))piperidine-4-yl; (prop-2-ynoxy(carbonyl))piperidine-4-yl; piperidine-4-yl; propoxycarbonylpiperidine-4-yl; (prop-2-enoxy(carbonyl)) piperidine-4-yl; (morpholine-4-yl(carbonyl))piperidine-4-yl; and 1-methoxycarbonylpiperidine-4-yl; bicyclo[2.2.1] hept-5-en-2-ylmethyl; and isopropylcarbonylpiperidine-4-yl.

2. Substituent R$_2$:

R$_2$ is —Z$^B$R$_5$, wherein each Z$^B$ is independently a bond or an optionally substituted branched or straight C$_{1-10}$ aliphatic chain wherein up to two carbon units of Z$^B$ are optionally and independently replaced by —C(O)—, —CS—, —C(O) NR$^B$—, —C(O)NR$^B$NR$^B$—, —C(O)O—, —OC(O), —NR$^B$C(O)O—, —O—, —NR$^B$C(O)NR$^B$—, —OC(O) NR$^B$—, —NR$^B$NR$^B$—, —NR$^B$C(O)—, —S—, —SO—, —SO$_2$—, —NR$^B$—, —SO$_2$NR$^B$—, —NR$^B$SO$_2$—, or —NR$^B$SO$_2$NR$^B$—. Each R$_5$ is independently R$^B$, halo, —OH, —NH$_2$, —NO$_2$, —CN, or —OCF$_3$. Each R$^B$ is independently an optionally substituted aliphatic, an optionally substituted cycloaliphatic, an optionally substituted heterocycloaliphatic, an optionally substituted aryl, or an optionally substituted heteroaryl.

In several embodiments, $R_2$ is $—Z^B R_5$, wherein each $Z^B$ is $—C(O)—$, $—O—$, $—C(O)O—$, $—C(O)NR^B—$, or $—NR^B C(O)—$; each $R_5$ is independently $R^B$, halo, $—OH$, $—NH_2$, $—NO_2$, $—CN$, or $—OCF_3$; and each $R^B$ is independently an optionally substituted aliphatic, an optionally substituted cycloaliphatic, an optionally substituted heterocycloaliphatic, an optionally substituted aryl, or an optionally substituted heteroaryl. In several examples, each $R^B$ is independently an aliphatic, a cycloaliphatic, a heterocycloaliphatic, an aryl, or a heteroaryl, each of which is optionally substituted with 1-3 of hydroxy, alkyl, cycloalkyl, heterocycloalkyl, aryl, heteroaryl, or combinations thereof.

In several embodiments, $R_2$ is an amido group. For example, $R_2$ is an optionally substituted aminocarbonyl. In other examples, $R_2$ is an optionally substituted aliphaticaminocarbonyl. Specifically, $R_2$ is an optionally substituted straight or branched ($C_{1-10}$ aliphatic(amino))carbonyl. In several examples, $R_2$ is pent-3-ylaminocarbonyl, methylaminocarbonyl, 1-methylbutylaminocarbonyl, isopropylaminocarbonyl, or N,N-diethylaminocarbonyl, each of which is optionally substituted. In several alternative examples, $R_2$ is an optionally substituted cycloaliphaticaminocarbonyl. For example, $R_2$ is an optionally substituted monocyclic cycloaliphaticaminocarbonyl or an optionally substituted bicyclic cycloaliphaticaminocarbonyl. In other examples, $R_2$ is a cyclobutylaminocarbonyl, a cyclopentylaminocarbonyl, a cyclohexylaminocarbonyl, a cycloheptylaminocarbonyl, or a cyclooctylaminocarbonyl, each of which is optionally substituted with 1-3 of halo, hydroxy, cyano, nitro, aliphatic, cycloaliphatic, heterocycloaliphatic, aryl, heteroaryl, or combinations thereof. In several alternative examples, $R_2$ is an optionally substituted heterocycloaliphaticaminocarbonyl. For example, $R_2$ is an optionally substituted monocyclic heterocycloaliphaticaminocarbonyl or an optionally substituted bicyclic heterocycloaliphaticaminocarbonyl. In other examples, $R_2$ is (tetrahydrofuranyl)aminocarbonyl, (tetrahydropyranyl)aminocarbonyl, (pyrrolidineyl)aminocarbonyl, (3-pyrrolineyl)aminocarbonyl, (2-pyrrolineyl)aminocarbonyl, (imidazolidineyl)aminocarbonyl, (piperidinyl)aminocarbonyl, (piperazinyl)aminocarbonyl, or (morpholinyl)aminocarbonyl, each of which is optionally substituted with 1-3 of halo, hydroxy, cyano, nitro, aliphatic, cycloaliphatic, heterocycloaliphatic, aryl, heteroaryl, or combinations thereof.

In several embodiments, $R_2$ is an acyl group. In several examples, $R_2$ is a carboxy group. For example, $R_2$ is hydroxycarbonyl, i.e., carboxylic acid, or $R_2$ is an (aliphatic(oxy))carbonyl, a (cycloaliphatic(oxy))carbonyl, a (heterocycloaliphatic(oxy))carbonyl, an (aryl(oxy))carbonyl, or a (heteroaryl(oxy))carbonyl, each of which is optionally substituted. In several examples, $R_2$ is an optionally substituted straight or branched ($C_{1-8}$ aliphatic(oxy))carbonyl group. In several examples, $R_2$ is methoxycarbonyl, ethoxycarbonyl, propoxycarbonyl, butoxycarbonyl, isopropoxycarbonyl, or tert-butoxycarbonyl, each of which is optionally substituted. In several examples, $R_2$ is an optionally substituted monocyclic or bicyclic (heterocycloaliphatic(oxy))carbonyl group. In several examples, $R_2$ is a (piperidinyl(oxy))carbonyl, a (pyrrolidineyl(oxy))carbonyl, a (piperazineyl(oxy))carbonyl, or a (morpholineyl(oxy))carbonyl, each of which is optionally substituted. In other embodiments, $R_2$ is an acyl such as an optionally substituted (heterocycloliphatic)carbonyl. In several embodiments, $R_2$ is one selected from (isopentyl)aminocarbonyl; (pentane-3-yl)aminocarbonyl; (methyl)aminocarbonyl; (1-methylbutyl)aminocarbonyl; (isopropyl)aminocarbonyl; (N,N-dimethyl)aminocarbonyl; (N,N-diethyl)aminocarbonyl; (ethoxy)carbonyl; carboxy; (piperidine-1-yl)carbonyl; (cyclopropyl)aminocarbonyl; (pyrrolidine-1-yl)carbonyl; (cyclohexyl)aminocarbonyl; cyano; and (cyclobutyl)aminocarbonyl.

3. Substituent $R_3$

Each $R_3$ is independently $—Z^D R_8$, wherein each $Z^D$ is independently a bond or an optionally substituted branched or straight $C_{1-8}$ aliphatic chain wherein up to two carbon units of $Z^D$ are optionally and independently replaced by $—C(O)—$, $—CS—$, $—C(O)NR^D—$, $—C(O)NR^D NR^D—$, $—C(O)O—$, $—OC(O)—$, $—NR^D C(O)O—$, $—O—$, $—NR^D C(O)NR^D—$, $—OC(O)NR^D—$, $—NR^D NR^D—$, $—NR^D C(O)—$, $—S—$, $—SO—$, $—SO_2—$, $—NR^D—$, $—SO_2 NR^D—$, $—NR^D SO_2—$, or $—NR^D SO_2 NR^D—$.

Each $R_8$ is independently $R^D$, halo, $—OH$, $—CN$, or $—OCF_3$;

Each $R^D$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

In several examples, $R_3$ is independently hydrogen, halo, or optionally substituted $C_{1-6}$ aliphatic.

In several examples, $R_3$ is an optionally substituted $C_{1-6}$ aliphatic. For example, $R_3$ is an optionally substituted methyl, ethyl, propyl, butyl, ethenyl, propenyl, butenyl, or combinations thereof, each of which is optionally substituted.

4. $Z_1$ Group $Z_1$ is a bond, $—O—$, $—NR_6—$, or $—C(R_6)_2—$, wherein each $R_6$ is independently $—Z^C R_7$, wherein each $Z^C$ is independently a bond or an optionally substituted branched or straight $C_{1-6}$ aliphatic chain wherein up to two carbon units of $Z^C$ are optionally and independently replaced by $—C(O)—$, $—CS—$, $—C(O)NR^C—$, $—C(O)NR^C NR^C—$, $—C(O)O—$, $—OC(O)—$, $—NR^C C(O)O—$, $—O—$, $—NR^C C(O)NR^C—$, $—OC(O)NR^C—$, $—NR^C NR^C—$, $—NR^C C(O)—$, $—S—$, $—SO—$, $—SO_2—$, $—NR^C—$, $—SO_2 NR^C—$, $—NR^C SO_2—$, or $NR^C SO_2 NR^C—$. Each $R_7$ is independently $R^C$, halo, $—OH$, $—NH_2$, $—NO_2$, $—CN$, or $—OCF_3$. Each $R^C$ is independently hydrogen, an optionally substituted aliphatic, an optionally substituted cycloaliphatic, an optionally substituted heterocycloaliphatic, an optionally substituted aryl, or an optionally substituted heteroaryl.

In many examples, $Z_1$ is a bond.

In one group of examples, $Z_1$ is $—NR_6—$, and $R_6$ is a hydrogen, or $R_6$ is (aliphatic)carbonyl, (aliphatic)sulfonyl, (cycloaliphatic)carbonyl, arylcarbonyl, heteroarylcarbonyl, (alkyl)aminocarbonyl, arylsulfonyl, alkoxycarbonyl, (cycloalkoxy)carbonyl, or heterocycloalkoxycarbonyl, each of which is optionally substituted with 1-3 of halo, aliphatic, alkoxy, cycloalkyl, or combinations thereof.

In another group of examples, $Z_1$ is a bond, $—O—$, $—NR_6—$, or $—C(R_6)_2—$, wherein each $R_6$ is independently hydrogen, halo, hydroxyl, or optionally substituted $C_{1-5}$ aliphatic.

5. Groups m, n, and p m is 0-4; n is 0-6; p is 0-6; and n+p is 2, 3, 4, 5, or 6.

In several examples, n is 2 and p is 2. In other examples, n is 1 and p is 3.

In several examples, m is 0, 1, 2, 3, or 4.

C. Subgeneric Compounds

Another aspect of the present invention provides compounds of formula Ia that are useful for modulating the activity and/or activities of muscarinic receptor(s). Compounds of formula Ia include:

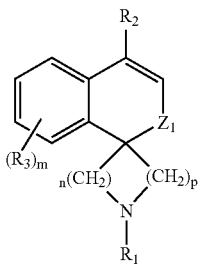

Ia or a pharmaceutically acceptable salt thereof, wherein $R_1$, $R_2$, $R_3$, $Z_1$, m, n and p are define above in formula I.

However, when $Z_1$ is a bond, n=2, and p=2, then $R_2$ is $Z^B R_5$, wherein each $Z^B$ is a bond, —CONR$^B$—, or —C(O)—; each $R_5$ is independently $R^B$, halo, —OH, —NH$_2$, —NO$_2$, —CN, or —OCF$_3$; and each $R^B$ is independently an optionally substituted aliphatic, an optionally substituted cycloaliphatic, or an optionally substituted heterocycloaliphatic.

In other examples, when $Z_1$ is absent, n=2, and p=2, then $R_2$ is —$Z^B R_5$, wherein each $Z^B$ is a bond or —C(O)NR$^B$—; each $R_5$ is $R^B$; and each $R^B$ is independently hydrogen or an optionally substituted aliphatic, an optionally substituted cycloaliphatic, an optionally substituted heterocycloaliphatic, an optionally substituted aryl, or an optionally substituted heteroaryl.

Another aspect of the present invention provides compounds of formula Ib that are useful for modulating the activity and/or activities of muscarinic receptor(s). Compounds of formula Ib include:

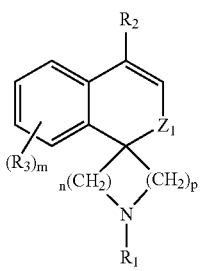

Ib or a pharmaceutically acceptable salt thereof, wherein $Z_1$, $R_3$, m, n, and p are define above in formula I.

$R_1$ is —$Z^A R_4$, wherein each $Z^A$ is independently a bond or —(CH$_2$)$_q$— where q is 1-2. Each $R_4$ is independently $R^A$, halo, —OH, —NH$_2$, —NO$_2$, —CN, or —OCF$_3$. Each $R^A$ is independently an (alkoxy)aliphatic, an (alkyl(sulfanyl))aliphatic, an unsubstituted aliphatic, an unsubstituted cycloaliphatic, or an optionally substituted heterocycloaliphatic.

$R_2$ is —$Z^B R_5$, wherein each $Z^B$ is a bond or —CONR$^B$—; each $R_5$ is independently hydrogen, an optionally substituted aliphatic, an optionally substituted cycloaliphatic, or an optionally substituted heterocycloaliphatic.

D. Combinations of Embodiments

Other embodiments include any combination of the aforementioned substituents $R_1$, $R_2$, $R_3$, $Z_1$, m, n, and p.

E. Exemplary Compounds

Specific exemplary compounds of formulae (I, Ia, and Ib) are shown below in Table 1.

TABLE 1

Exemplary compounds of formulae (I, Ia, and Ib).

| | |
|---|---|
| 1 | 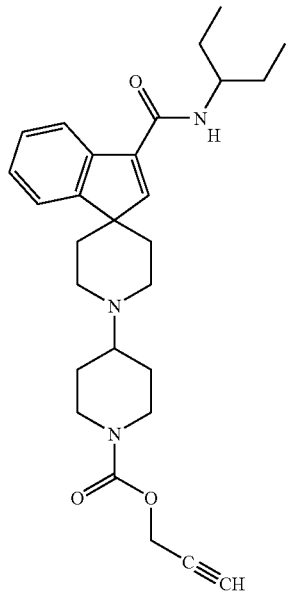 |
| 2 | 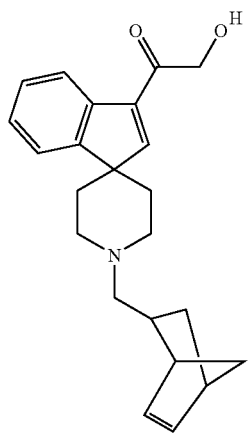 |
| 3 | 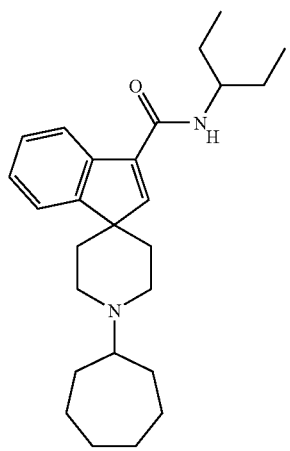 |

-continued
| | |
|---|---|
| 4 | 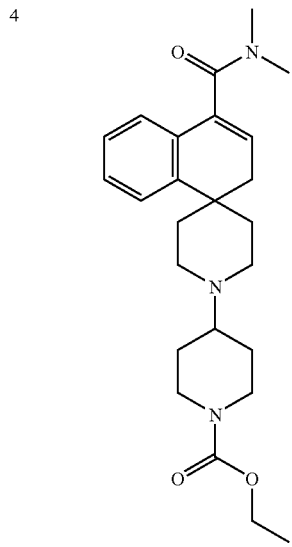 |
| 5 | 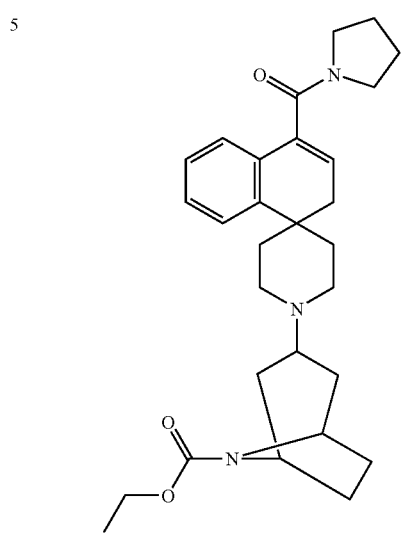 |
| 6 | 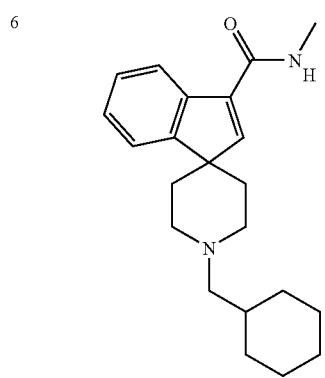 |
-continued
| | |
|---|---|
| 7 | 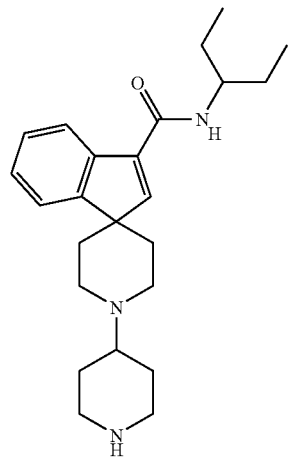 |
| 8 | 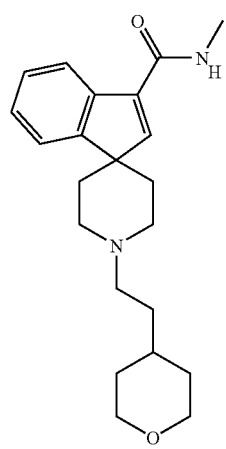 |
| 9 | 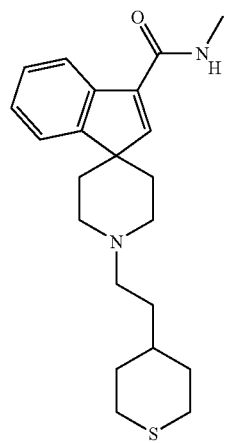 |

-continued
10
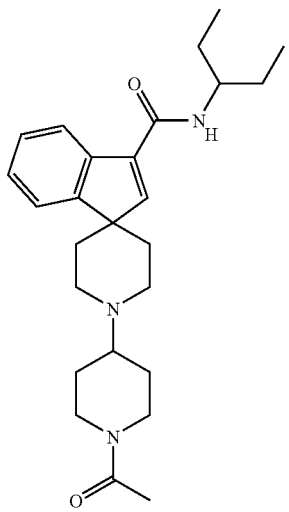
11
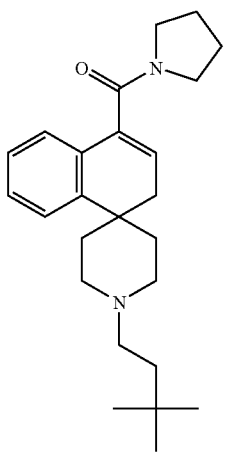
12
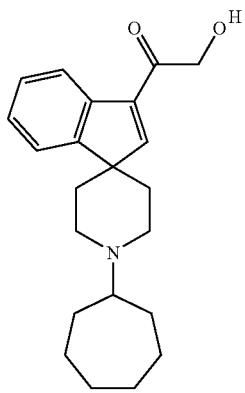
-continued
13
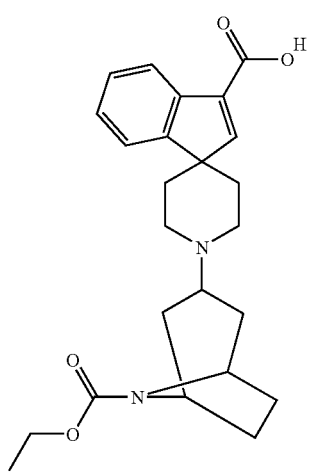
14
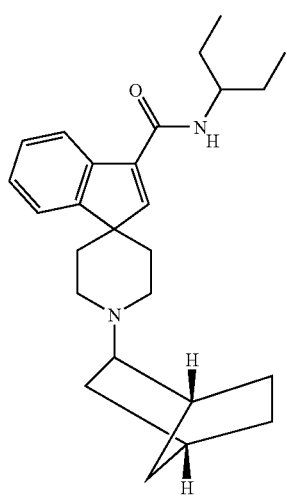
15
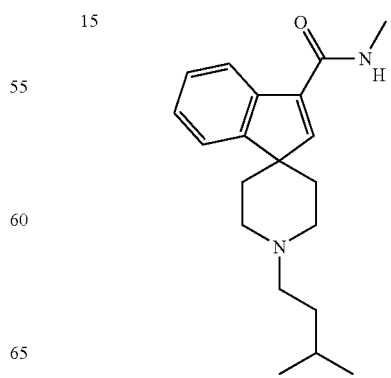

-continued
16
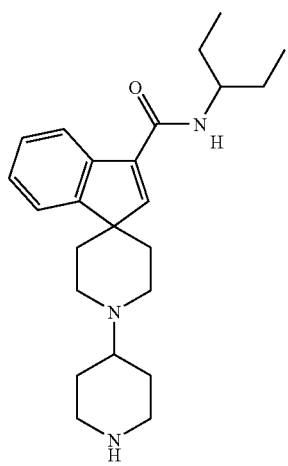
17
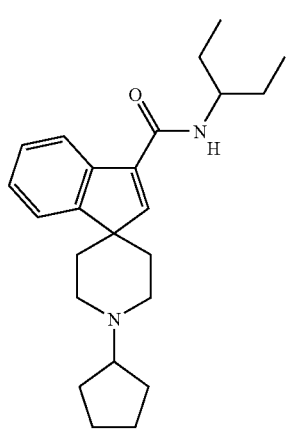
18
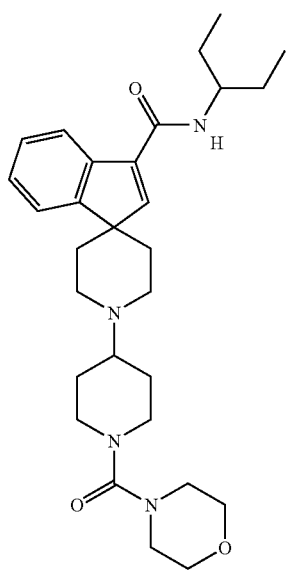
-continued
19
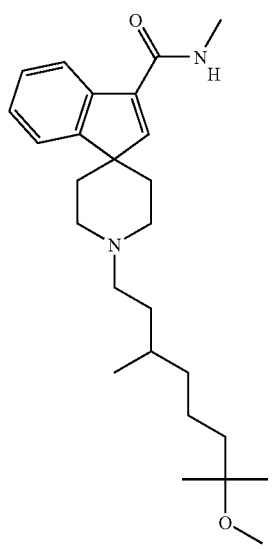
20
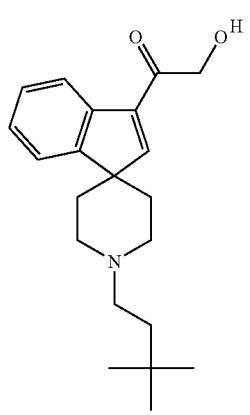
21
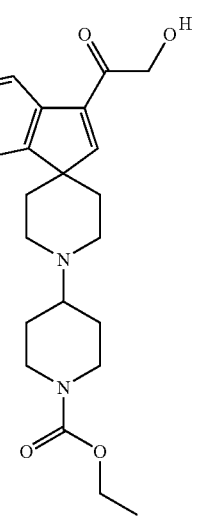

22
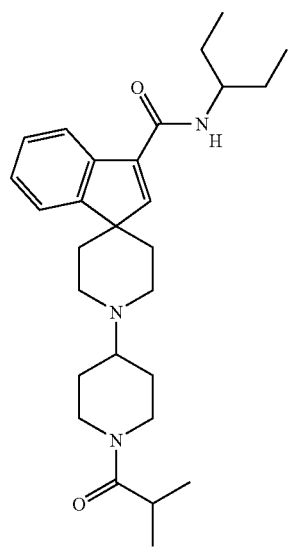
23
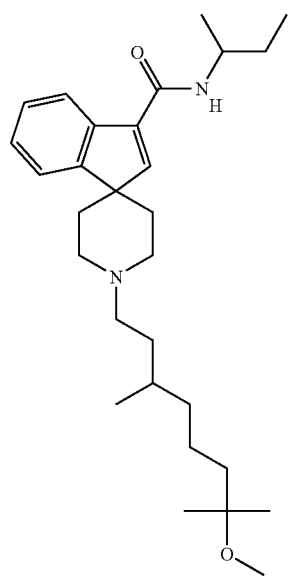
24
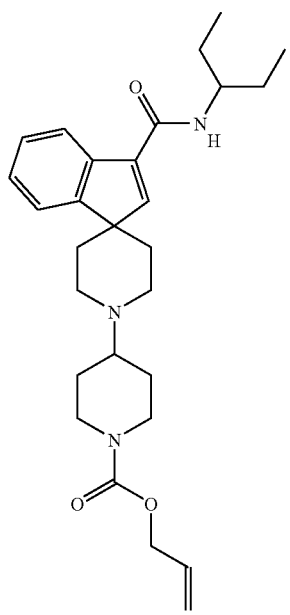
25
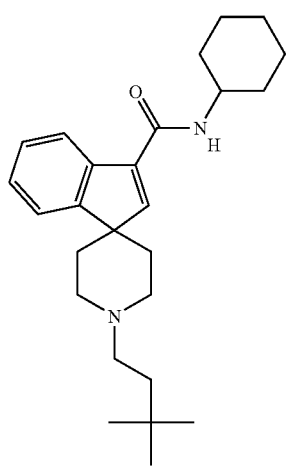
26
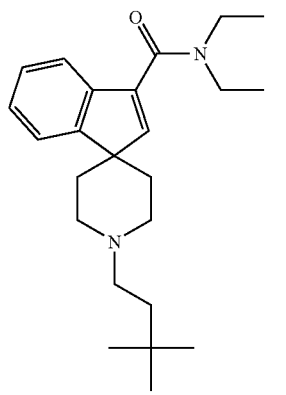

27
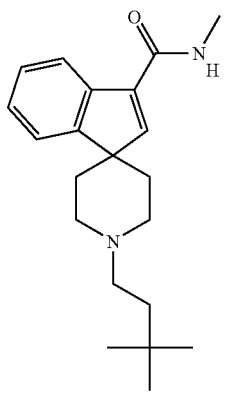
28
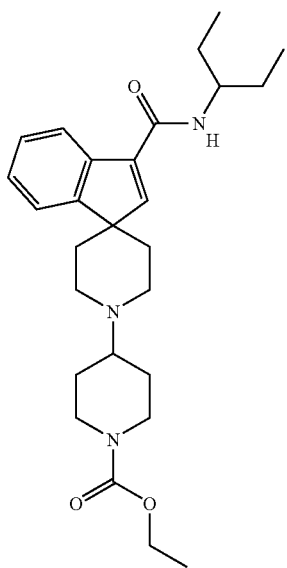
29
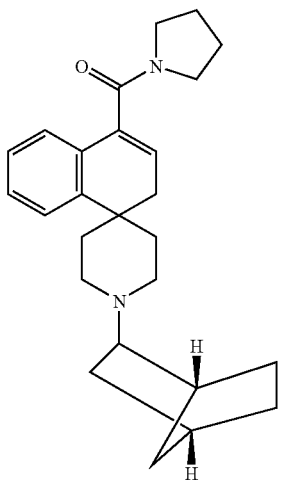
30
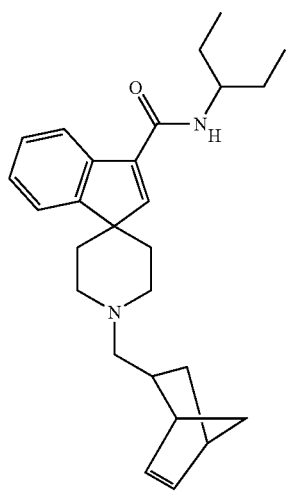
31
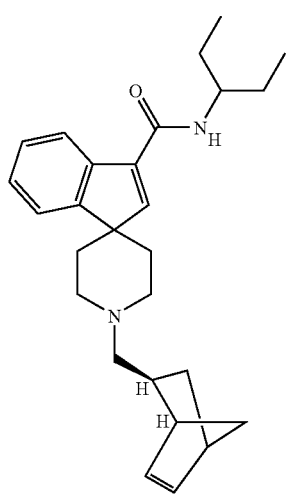
32
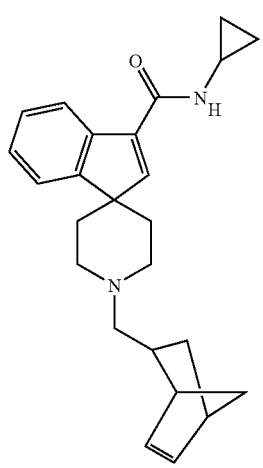

33
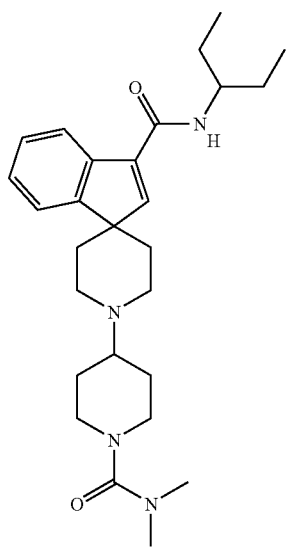
34
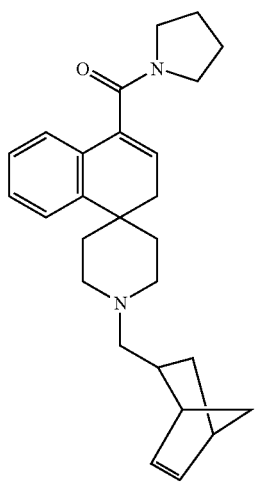
35
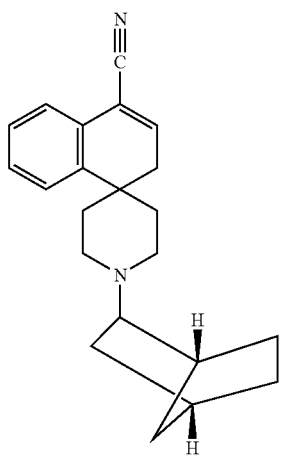
36
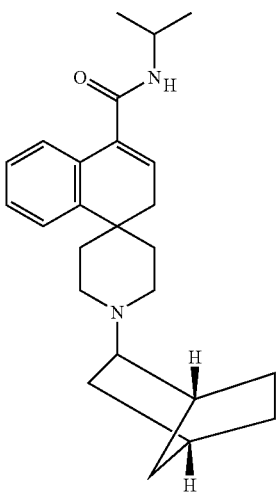
37
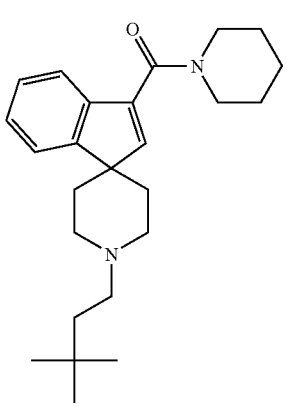
38
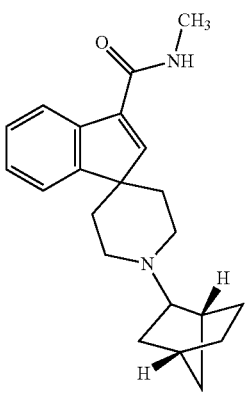

| | |
|---|---|
| 39 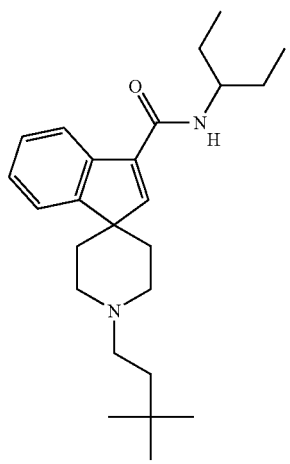 | 42 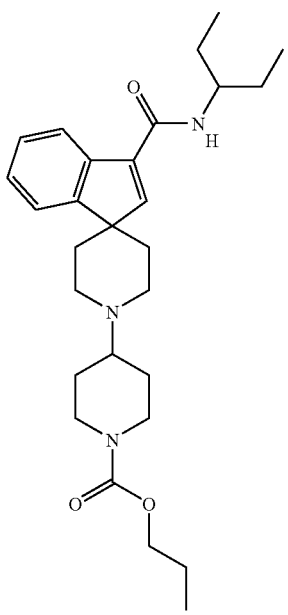 |
| 40 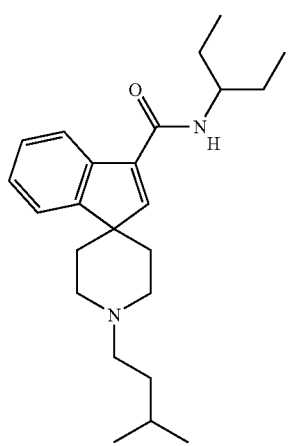 | 43 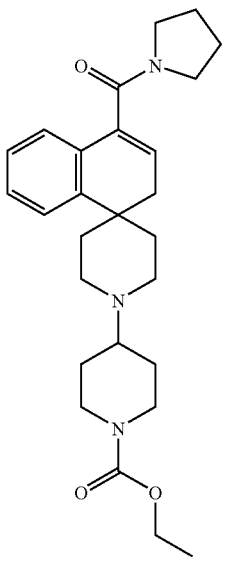 |
| 41 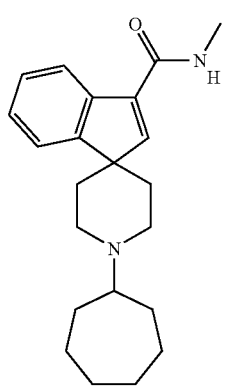 | 44 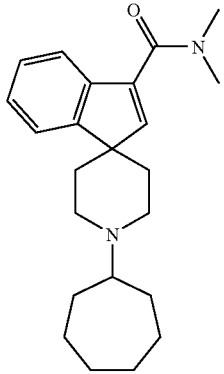 |

| 45 | 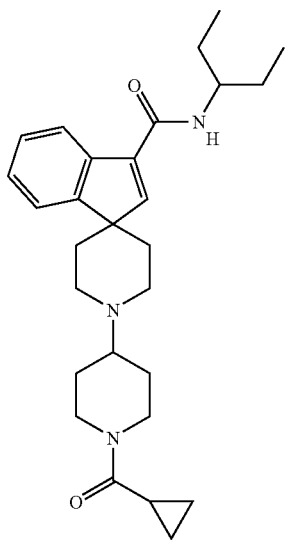 |
|---|---|
| 46 | 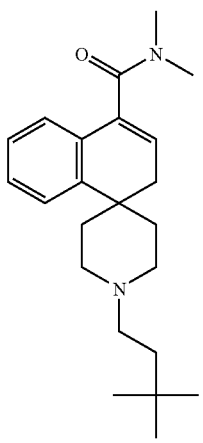 |
| 47 | 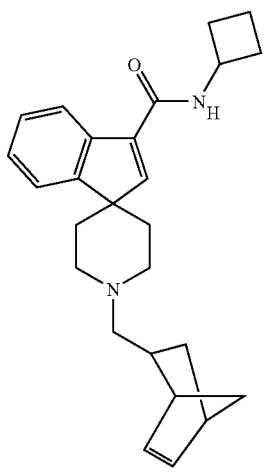 |
| 48 | 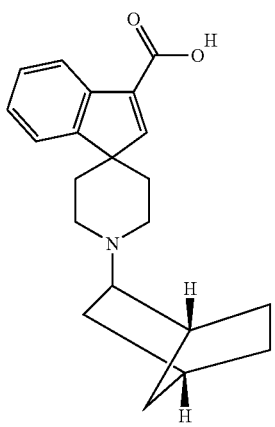 |
|---|---|
| 49 | 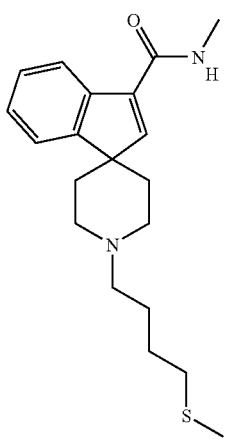 |
| 50 | 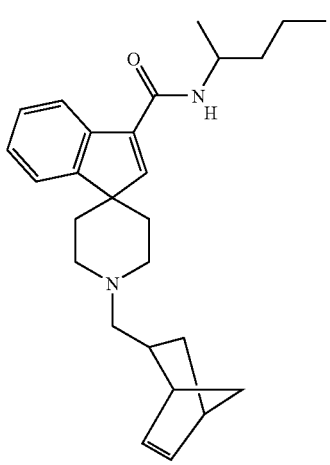 |

-continued
51
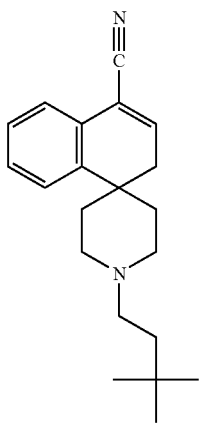
52
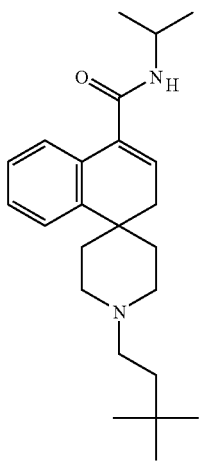
53
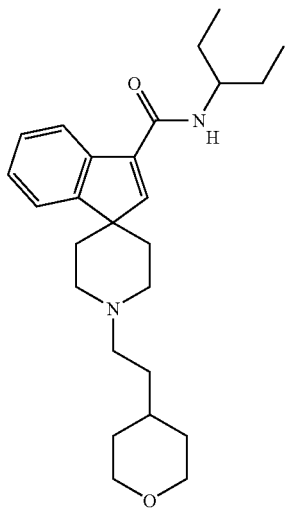
-continued
54
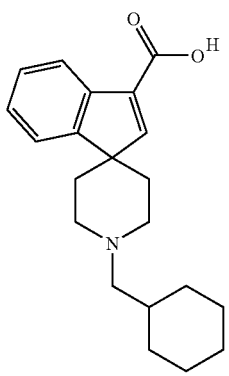
55
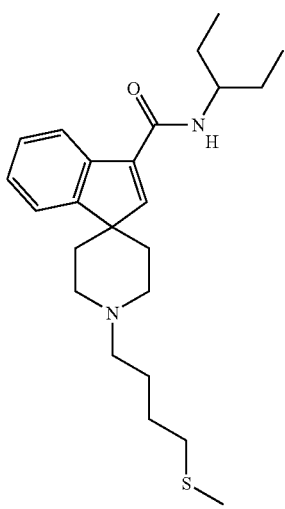
56
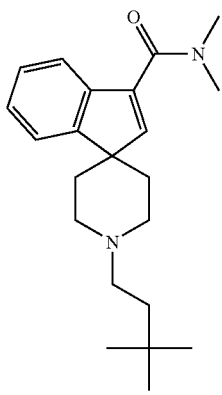
57
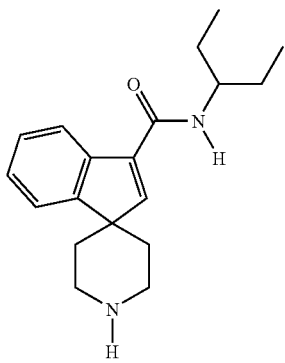

-continued
| | |
|---|---|
| 58 | 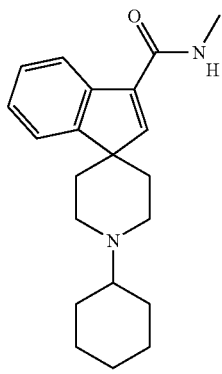 |
| 59 | 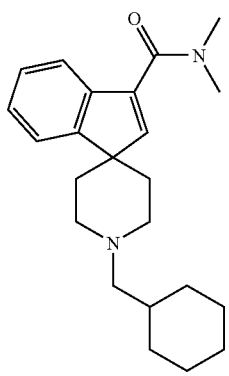 |
| 60 | 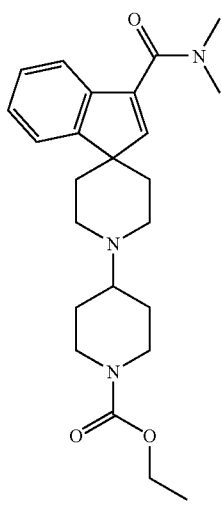 |
| 61 | 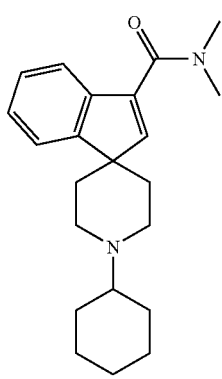 |
-continued
| | |
|---|---|
| 62 | 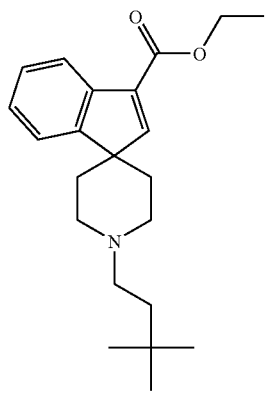 |
| 63 | 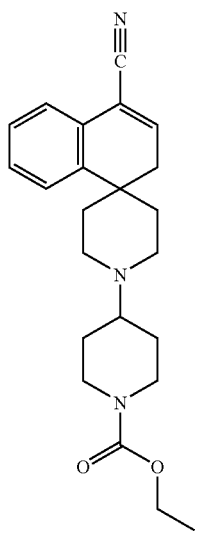 |
| 64 | 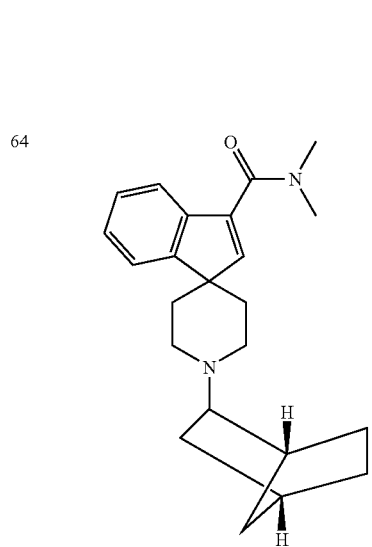 |

-continued
65 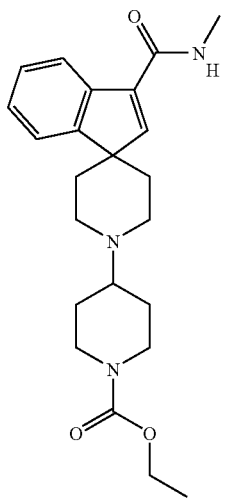
66 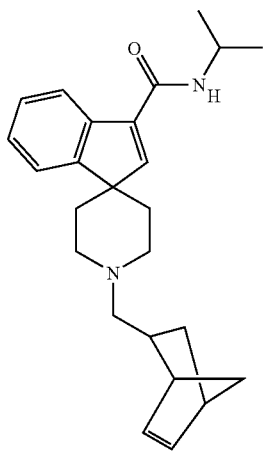
67 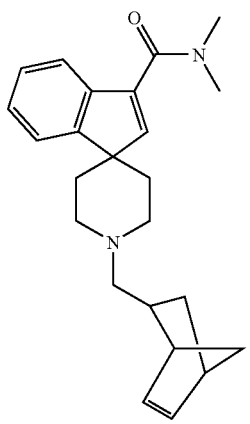
-continued
68 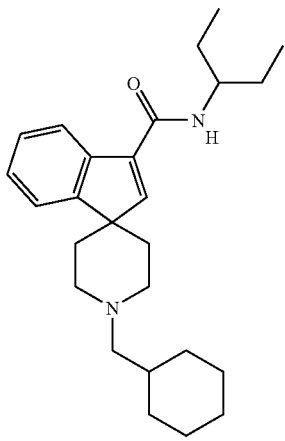
69 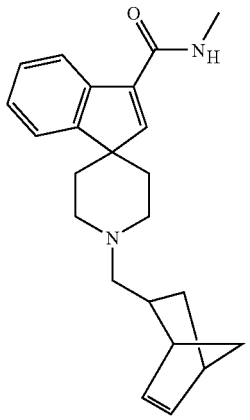
70 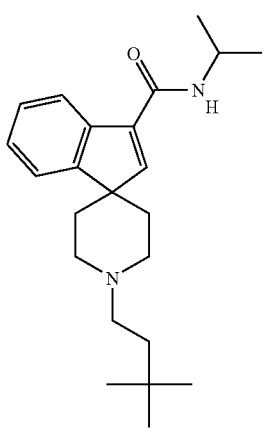

| | |
|---|---|
| 71 | 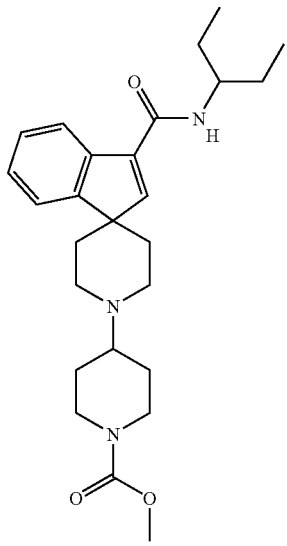 |
| 72 | 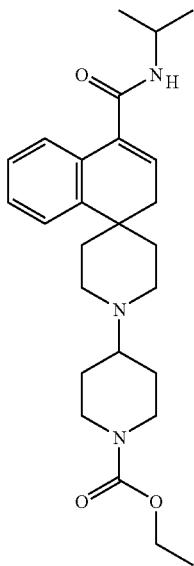 |
| 73 | 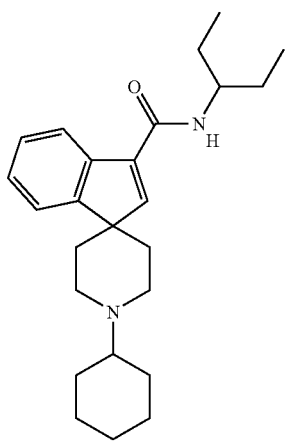 |
| 74 | 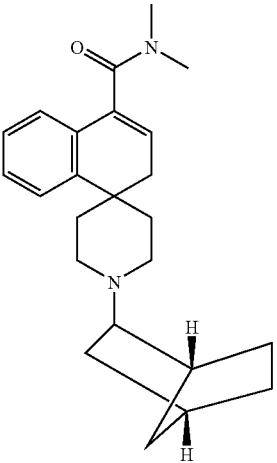 |
| 75 | 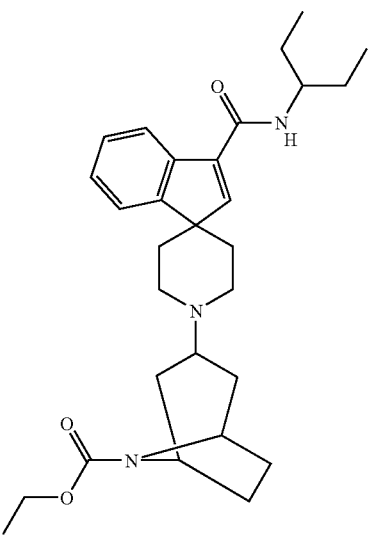 |
| 76 | 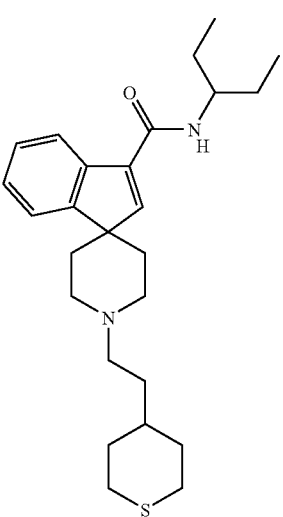 |

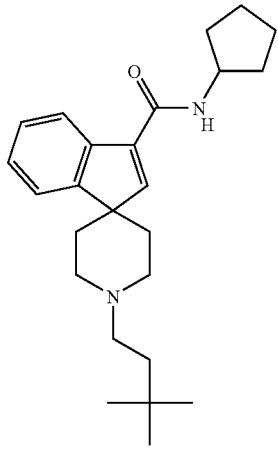

III. Synthetic Schemes

The compounds of formulae (I, Ia, and Ib) may be readily synthesized from commercially available starting materials using methods known in the art. Exemplary synthetic routes to produce compounds of formulae (I, Ia, and Ib), are provided below in Preparations A-O and Schemes 1-3. In the following generic schemes, for purposes of simplicity, a single formula is used wherein n and p are both 2, and $Z_1$ is —$CH_2$— or a bond. However, the generic schemes are not limiting and can be applied to preparation of other compounds of formulae (I, Ia, and Ib) having different variables.

Scheme 1 below depicts general conditions for the synthesis of compounds of formula I wherein $R_2$ is —$CONR^BR_5$.

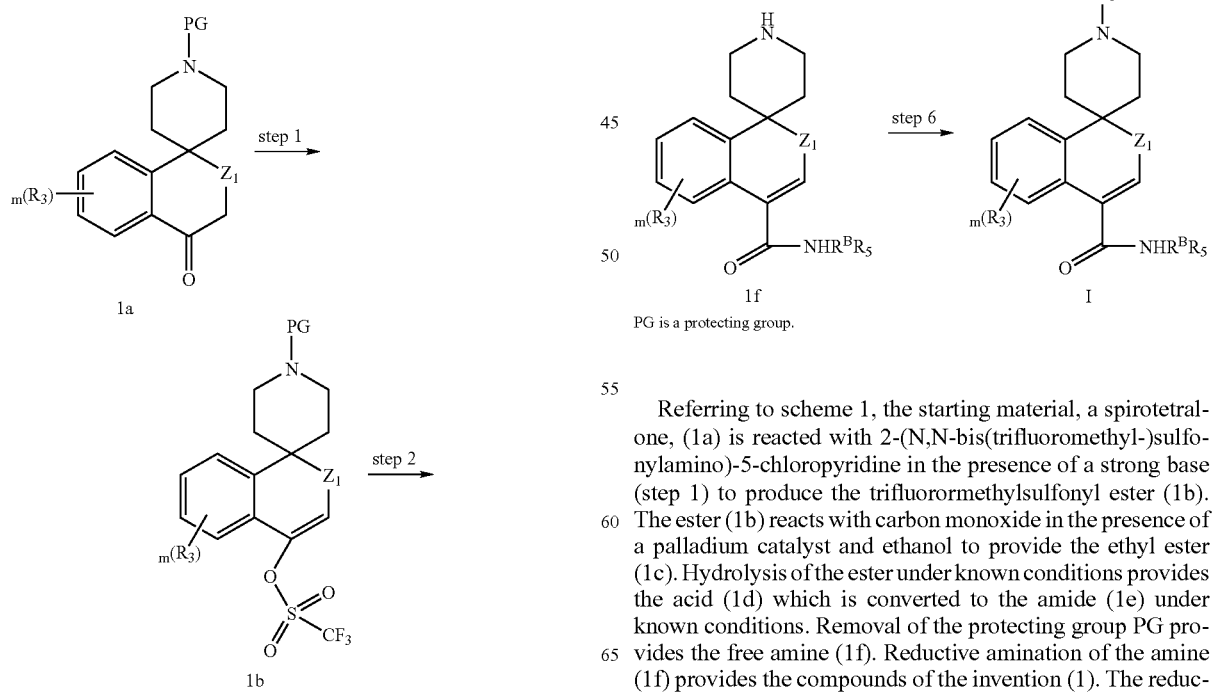

PG is a protecting group.

Referring to scheme 1, the starting material, a spirotetralone, (1a) is reacted with 2-(N,N-bis(trifluoromethyl-)sulfonylamino)-5-chloropyridine in the presence of a strong base (step 1) to produce the trifluorormethylsulfonyl ester (1b). The ester (1b) reacts with carbon monoxide in the presence of a palladium catalyst and ethanol to provide the ethyl ester (1c). Hydrolysis of the ester under known conditions provides the acid (1d) which is converted to the amide (1e) under known conditions. Removal of the protecting group PG provides the free amine (1f). Reductive amination of the amine (1f) provides the compounds of the invention (1). The reductive amination is conducted with an appropriate aldehyde or ketone in the presence of a reducing reagent such as sodium triacetoxyborohydride and, optionally, a catalyst such as, for example, trifluoroacetic acid or titanium (IV) isopropoxide. Compounds of formula I wherein R₁ contains, for example, a protected amine can be further modified by known methods to provide additional examples of compounds of formula I.

Scheme 2 below depicts alternative conditions for the synthesis of compounds of formula I.

Scheme 2:

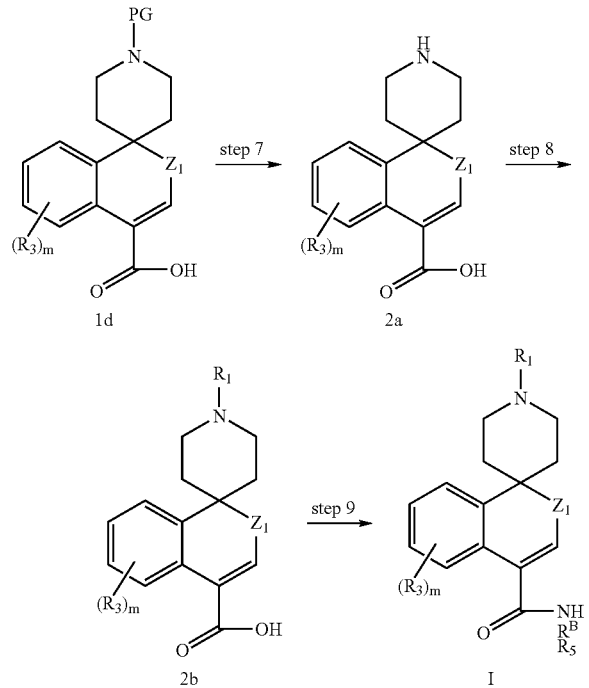

The acid (1d) (Scheme 1) is deprotected to provide the amine acid (2a). Reductive amination of (2a) as described above provides the acid (2b) which is converted to the amide of Formula I.

Preparation of the compounds of Formula I wherein R₂ is —CN may be prepared as illustrated in Scheme 3.

Scheme 3:

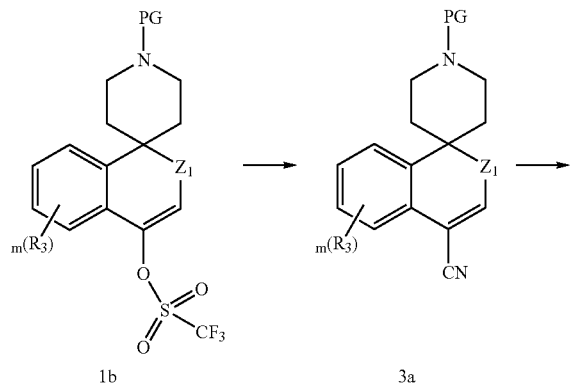

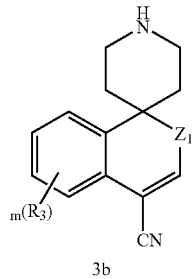

Reaction of the trifluorormethylsulfonyl ester (1b) (Scheme 1) with an alkaline metal cyanide such as, for example, sodium cyanide, in the presence of a copper catalyst such as, for example, copper iodide and tetrakis(triphenylphosphine)palladium (0) provides the protected nitrile (3a). Deprotection provides the compounds (3b) wherein R₂ is —CN, which can be converted to compounds of formula I as previously described.

IV. Formulations, Administrations, and Uses

The present invention includes within its scope pharmaceutically acceptable prodrugs of the compounds of the present invention. A "pharmaceutically acceptable prodrug" means any pharmaceutically acceptable salt, ester, salt of an ester, or other derivative of a compound of the present invention which, upon administration to a recipient, is capable of providing (directly or indirectly) a compound of this invention or an active metabolite or residue thereof. Preferred prodrugs are those that increase the bioavailability of the compounds of this invention when such compounds are administered to a mammal or which enhance delivery of the parent compound to a biological compartment relative to the parent species.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\ alkyl)_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intraarticular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the modulator can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

According to a preferred embodiment, the compounds of formulae (I, Ia, and Ib) are selective modulators of $M_1$, $M_2$ and $M_4$. More preferably, the compounds of formulae (I, Ia, and Ib) are selective modulators of $M_1$ and/or $M_4$. Yet more preferably, certain compounds of formulae (I, Ia, and Ib) are selective modulators of $M_1$. Or, preferably, certain compounds of formulae (I, Ia, and Ib) are selective modulators of $M_4$.

Applicants believe that the ability of the compounds of the present invention to modulate the activity of muscarinic receptors is derived from the affinity of these compounds to the muscarinic receptors. Such affinity, applicants believe, activates a muscarinic receptor (i.e., an agonist) or inhibits the activity of a muscarinic receptor.

The term "selective" as used herein means a measurably greater ability to modulate one muscarinic receptor subtype when compared to the other muscarinic receptor subtypes. E.g., the term "selective $M_4$ agonist" means a compound that has a measurably greater ability to act as an $M_4$ agonist when compared to that compound's agonist activity with the other muscarinic receptor subtype(s).

According to an alternative embodiment, the present invention provides a method of treating a muscarinic receptor mediated disease in a mammal, such as a human, including the step of administering to said mammal a composition comprising a compound of formulae (I, Ia, and Ib) or an embodiment thereof as set forth herein.

According to another embodiment, the present invention provides a method of treating a disease mediated by a muscarinic receptor including the step of administering to said mammal a composition comprising a compound of formulae (I, Ia, and Ib), or other embodiments thereof as set forth above. Preferably, said disease is mediated by $M_1$, or said disease is mediated by $M_4$.

According to yet another embodiment, the present invention provides a method of treating or reducing the severity of a disease in a patient, wherein said disease is selected from CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, sudden infant death syndrome, Parkinson's disease, peripheral disorders such as reduction of intra ocular pressure in Glaucoma and treatment of dry eyes and dry mouth including Sjögren's Syndrome, wherein said method comprises the step of contacting said patient with a compound according to the present invention.

According to an alternative embodiment, the present invention provides a method of treating or reducing the severity of a disease in a patient, wherein said disease is selected from pain, psychosis (including schizophrenia, hallucinations, and delusions), Alzheimer's disease, Parkinson's disease, glaucoma, bradycardia, gastric acid secretion, asthma, or GI disturbances.

According to a preferred embodiment, the present invention is useful for treating or reducing the severity of psychosis, Alzheimer's disease, pain, or Parkinson's disease.

All references cited within this document are incorporated herein by reference.

V. PREPARATIONS AND EXAMPLES

In order that the invention described herein may be more fully understood, the following examples are set forth. It should be understood that these examples are for illustrative purposes only and are not to be construed as limiting this invention in any manner.

Preparation A

Synthesis of 2H-spiro[naphthalene-1,4'-piperidine]-4-carbonitrile (A4)

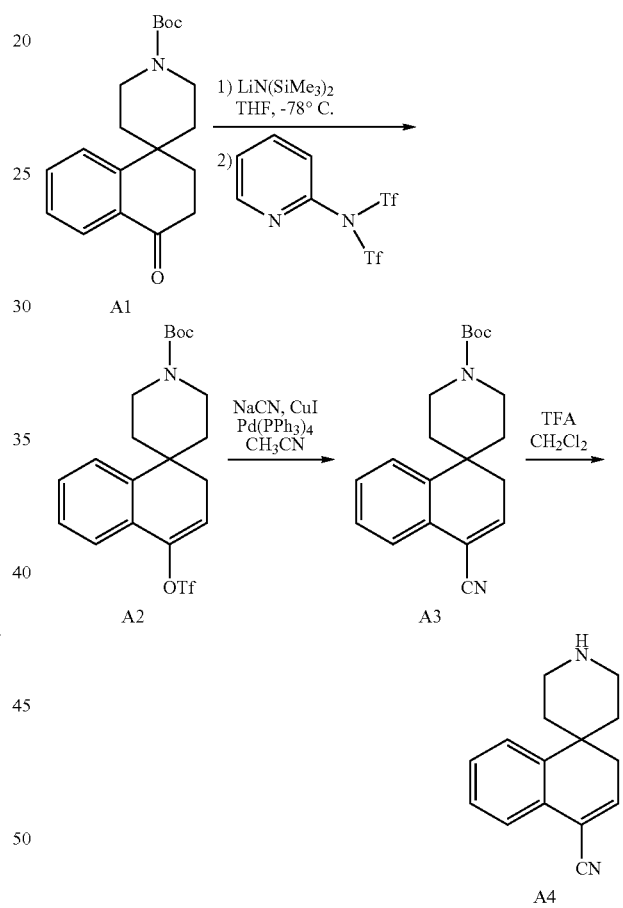

At −78° C., a solution of tert-butyl 4-oxo-3,4-dihydro-2H-spiro[naphthalene-1,4'-piperidine]-1'-carboxylate (A1) (2.66 g, 8.44 mmol) in THF (30 ml) was added dropwise to a solution of lithium bis(trimethylsilyl)amide (1.0M in hexane, 10.5 ml, 10.5 mmol) in THF (20 ml). After 30 min at −78° C., 2-(N,N-bis(trifluoromethylsulfonyl)amino)-pyridine (3.77 g, 10.5 mmol) was added and the reaction mixture was slowly warmed to 0° C. (ca. 2 h), poured into ice, extracted with ether, and purified by flash chromatography on silica gel (hexane/dichloromethane 8:2) to give tert-butyl 4-(trifluoromethylsulfonyloxy)-2H-spiro[naphthalene-1,4'-piperidine]-1'-carboxylate (A2). LC-MS: m/e=391.9 (M+H−C(CH$_3$)$_3$). $R_t$=4.19 min. $^1$H-NMR (500 MHz, DMSO-d$_6$):

7.50 (d, 1H), 7.40 (t, 1H), 7.30 (t, 1H), 6.16 (t, 1H), 3.83 (br. d, 2H), 3.05 (br. s, 2H), 2.67 (d, 2H), 1.72-1.67 (m, 4H), 1.41 (s, 9H).

A mixture of the triflate (A2) (447 mg, 1 mmol), sodium cyanide (100 mg, 2 mmol), copper (I) iodide (19 mg, 0.1 mmol) and tetrakis(triphenylphosphine)palladium(0) (58 mg, 0.05 mmol) in acetonitrile (10 ml) was degassed and heated under reflux under nitrogen for 4 h. After concentration, the residue was directly purified by flash chromatography (hexane/EtOAc 8:2) to give tert-butyl 4-cyano-2H-spiro[naphthalene-1,4'-piperidine]-1'-carboxylate (A3) (300 mg). LC-MS: m/e=269.0 (M+H−C(CH$_3$)$_3$. R$_t$=3.75 min. $^1$H-NMR (500 MHz, DMSO-d$_6$): 7.49 (d, 1H), 7.42-7.36 (m, 3H), 7.09 (t, 1H), 3.81 (br. d, 2H), 3.03 (br. s, 2H), 2.67 (d, 2H), 1.70 (td, 2H), 1.62 (d, 2H), 1.41 (s, 9H), A solution of the nitrile (A3) (300 mg) in dichloromethane (3 ml) was treated with TFA (1 ml) for 1 hour, concentrated, co-evaporated with acetonitrile and dissolved in dichloromethane (ca. 100 ml). The resulting solution was washed with a mixture of brine (ca. 20 ml) and 6N NaOH (2 ml), dried over Na$_2$SO$_4$, and concentrated to give 2H-spiro[naphthalene-1,4'-piperidine]-4-carbonitrile (A4) as a white solid. LC-MS: m/e=225.2 (M+H). R$_t$=1.53 min.

Preparation B: Synthesis of N,N-dimethyl-2H-spiro[naphthalene-1,4'-piperidine]-4-carboxamide (B3)

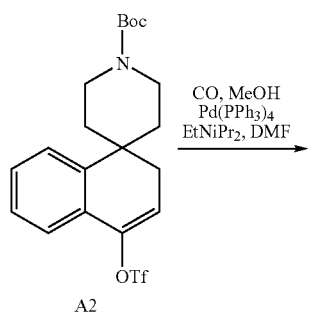

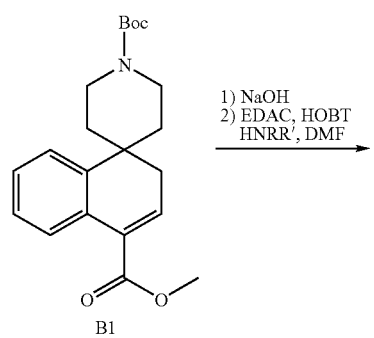

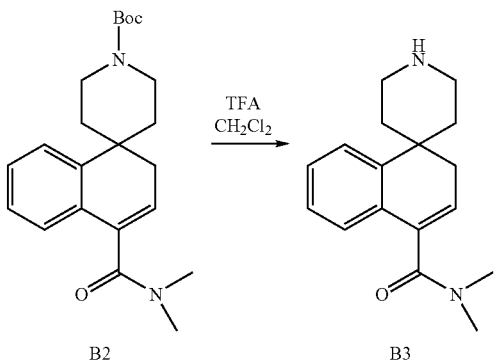

A mixture of the triflate (A2) (2.25 g, 5 mmol), methanol (10 ml), N,N-diisopropylethylamine (3 ml), tetrakis(triphenylphosphine)palladium(0) (340 mg), in DMF (20 ml) was degassed and exchanged with carbon monoxide. The mixture was stirred at 50° C. under 1 atmosphere of carbon monoxide for 20 h. After evaporation to remove the excess methanol, the mixture was poured into water, extracted with ether, and purified by flash chromatography to give 1'-tert-butyl 4-methyl 2H-spiro[naphthalene-1,4'-piperidine]-1',4-dicarboxylate (B1) (1.58 g). LC-MS: m/e=302.0 (M+H—C(CH$_3$)$_3$). R$_t$=3.82 min. $^1$H-NMR (500 MHz, DMSO-d$_6$): 7.67 (d, 1H), 7.41 (d, 1H), 7.30 (t, 1H), 7.24 (t, 1 H), 7.00 (t, 1 H), 3.82 (s, H), 3.78 (br. d, 2H), 2.75 (s, 3H), 3.29 (s, 3 H), 3.11 (br. s, 2H), 2.55 (s, 2H), 1.68 (m, 2 H), 1.61 (d, 2H), 1.41 (s, 9H).

A solution of the methyl ester (B1) (1.59 g, 4.66 mmol) in MeOH (20 ml) was heated with 6N NaOH (2 ml) at 65° C. for 2 h. The reaction mixture was cooled with in an ice-bath, its pH was adjusted to ca. 5 with 0.5N HCl, and extracted with dichloromethane three times. The combined extracts were dried with sodium sulfate, filtered and concentrated to give 1'-(tert-butoxycarbonyl)-2H-spiro[naphthalene-1,4'-piperidine]-4-carboxylic acid. LC-MS: m/e=344.0 (M+H), 288.0 (M+H—C(CH$_3$)$_3$), 244.0 (M+H−Boc). R$_t$=3.29 min. $^1$H-NMR (500 MHz, DMSO-d$_6$): 8.05 (dd, 1 H), 7.80 (d, 1 H), 7.68 (t, 1 H), 7.46 (t, 1 H), 6.74 (s, 1H), 4.03 (m, 2 H), 3.71 (s, 2H), 3.4 (m, 2H), 2.21 (td, 2H), 1.46 (s, 9H), 1.45 (m, 2H).

A solution of the above crude carboxylic acid (300 mg, ca. 0.87 mmol), dimethylamine (2.0M in THF, 0.88 ml, 1.76 mmol), 1-(3-dimethylaminopropyl)-3-ethylcarbodiimide hydrochloride (EDCI, 338 mg, 1.76 mmol), hydroxybenzotriazole hydrate (178 mg, 1.31 mmol) in DMF (10 ml) was stirred at room temperature for 24 h, poured into water, extracted with EtOAc (three times). The extracts were dried (Na$_2$SO$_4$), concentrated and purified by flash chromatography (hexane/EtOAc 1:0 to 0:1) to give tert-butyl 4-(dimethylcarbamoyl)-2H-spiro[naphthalene-1,4'-piperidine]-1'-carboxylate (B2) (156 mg). LC-MS: m/e=371.1 (M+H), 315.0 (M+H−C(CH$_3$)$_3$). R$_t$=3.16 min. $^1$H-NMR (500 MHz, CDCl$_3$): 7.32-7.27 (m, 2H), 7.13 (t, 1H), 6.97 (d, 1H), 6.00 (t, 1 H), 3.91 (br. d, 2H), 3.04 (br. s, 3H), 2.97 (t, 2H), 2.85 (br. s, 3H), 2.44 (br. s, 2H), 1.85 (m, 2H), 1.70 (d, 2H), 1.40 (s, 9H).

A solution of the dimethylamide (B2) (156 mg) in dichloromethane (5 ml) was treated with TFA (1 ml) for 1 h. After concentration and co-evaporation with acetonitrile, the residue was dissolved in dichloromethane, washed with a mixture of brine and 1 ml 6N NaOH, dried (Na$_2$SO$_4$), and concentrated to give N,N-dimethyl-2H-spiro[naphthalene-1,4'-piperidine]-4-carboxamide (B3) (135 mg). LC-MS: m/e=271.0 (M+H). R$_t$=1.30 min.

Method A: Reductive Amination of a Spiropiperidine with an Aldehyde—Synthesis of 1'-(3,3-dimethylbutyl)-2H-spiro[naphthalene-1,4'-piperidine]-4-carbonitrile (Compound No. 51)

Method B: Reductive Amination of a Spiropiperidine with a Ketone—Synthesis of ethyl 4-(4-(dimethylcarbamoyl)-2H-spiro[naphthalene-1,4'-piperidine]-1'-yl)piperidine-1-carboxylate (Compound No. 4)

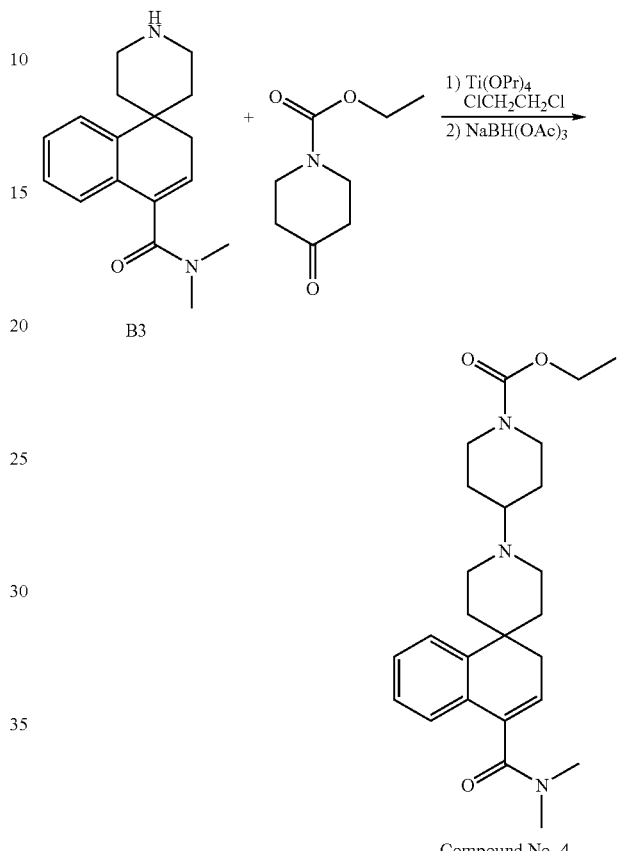

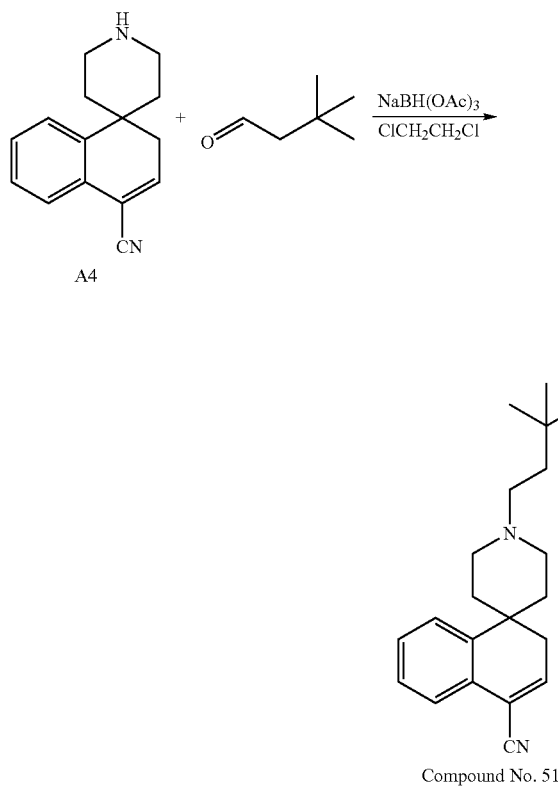

A solution of 2H-spiro[naphthalene-1,4'-piperidine]-4-carbonitrile (A4) (66 mg, 0.3 mmol), 3,3-dimethylbutanal (46 mg, 0.46 mmol) in 1,2-dichloroethane (5 ml) was stirred at 40° C. for 2 h. To the solution was added sodium triactoxyborohydride and the resulting mixture was stirred overnight, followed by treatment of MeOH (1 ml). Evaporation and the residue was dissolved in MeOH (2 ml) and purified by reverse phase C-18 HPLC to give 1'-(3,3-dimethylbutyl)-2H-spiro[naphthalene-1,4'-piperidine]-4-carbonitrile (Compound No. 51). LC-MS: m/e=309.1 (M+H). R$_t$=1.92 min. $^1$H-NMR (500 MHz, DMSO-d$_6$): 9.03 (br. s, 1H), 7.49-7.40 (m, 4H), 7.12 (t, 1H), 3.45 (d, 2H), 3.22-3.11 (m, 4H), 2.78 (d, 2H), 2.03 (td, 2H), 1.88 (d, 2H), 1.58-1.54 (m, 2H), 0.92 (s, 9H).

A solution of N,N-dimethyl-2H-spiro[naphthalene-1,4'-piperidine]-4-carboxamide (B3) (33 mg, 0.13 mmol) and ethyl 4-oxopiperidine-1-carboxylate (60 mg, 0.35 mmol) in 1,2-dichloroethane (2 ml) was stirred at 40° C. for 5 h, followed by addition of titanium (IV) isopropoxide (0.05 ml, 0.17 mmol). The reaction mixture was stirred for 18 h and treated with sodium triacetoxyborohydride (50 mg, 0.23 mmol) for 24 h. Methanol (1 ml) was added and the reaction mixture was stirred for 1 h, evaporated and the residue was dissolved in methanol (1 ml) and purified by C-18 HPLC to give ethyl 4-(4-(dimethylcarbamoyl)-2H-spiro[naphthalene-1,4'-piperidine]-1'-yl)piperidine-1-carboxylate (Compound No. 4). LC-MS: m/e=426.3 (M+H). R$_t$=1.55 min. $^1$H-NMR (500 MHz, DMSO-d$_6$): 9.32 (br. s, 1H), 7.39 (d, 1H), 7.34 (t, 1H), 7.26 (t, 1H), 6.95 (d, 1H), 5.97 (t, 1H), 4.12 (d, 2H), 4.05 (q, 2H), 4.04 (m, 2H), 3.43 (br. d, 2H), 3.22 (q, 2H), 2.98 (s, 3H), 2.81 (s, 3H), 2.80 (m, 1H), 2.56 (d, 2H), 2.14-2.07 (m, 4H), 1.92 (d, 2H), 1.56 (qd, 2H), 1.19 (t, 3H).

The examples in Table 2 generally follow the synthetic preparations and methods described above in Preparations A-B and Methods A-B; however, these preparation and methods are only exemplary, and other suitable preparations and methods may be used.

TABLE 2

Exemplary compounds synthesized following preparations A-B and methods A-B.

| Example No. | Comp. No. | R₁ | R₂ | Method |
|---|---|---|---|---|
| 1 | 51 | neohexyl (CH₂CH₂C(CH₃)₃) | -CN | A |
| 2 | 35 | norbornyl (exo) | -CN | B |
| 3 | 63 | ethyl piperidine-1-carboxylate (4-yl) | -CN | B |
| 4 | 46 | neohexyl | -C(O)N(CH₃)₂ | A |
| 5 | 74 | norbornyl (exo) | -C(O)N(CH₃)₂ | B |
| 6 | 4 | ethyl piperidine-1-carboxylate (4-yl) | -C(O)N(CH₃)₂ | B |
| 7 | 11 | neohexyl | -C(O)-pyrrolidin-1-yl | A |
| 8 | 29 | norbornyl (exo) | -C(O)-pyrrolidin-1-yl | B |
| 9 | 43 | ethyl piperidine-1-carboxylate (4-yl) | -C(O)-pyrrolidin-1-yl | B |
| 10 | 5 | ethyl azabicyclic carboxylate | -C(O)-pyrrolidin-1-yl | B |
| 11 | 34 | norbornenyl-methyl | -C(O)-pyrrolidin-1-yl | A |
| 12 | 52 | neohexyl | -C(O)NHCH(CH₃)₂ | A |

TABLE 2-continued
Exemplary compounds synthesized following preparations A-B and methods A-B.
| Example No. | Comp. No. | R₁ | R₂ | Method |
|---|---|---|---|---|
| 13 | 36 | norbornyl | isopropyl carboxamide | B |
| 14 | 72 | ethyl piperidine carbamate | isopropyl carboxamide | B |
Preparation C: Synthesis of N-methylspiro[indene-1,4'-piperidine]-3-carboxamide (C6)
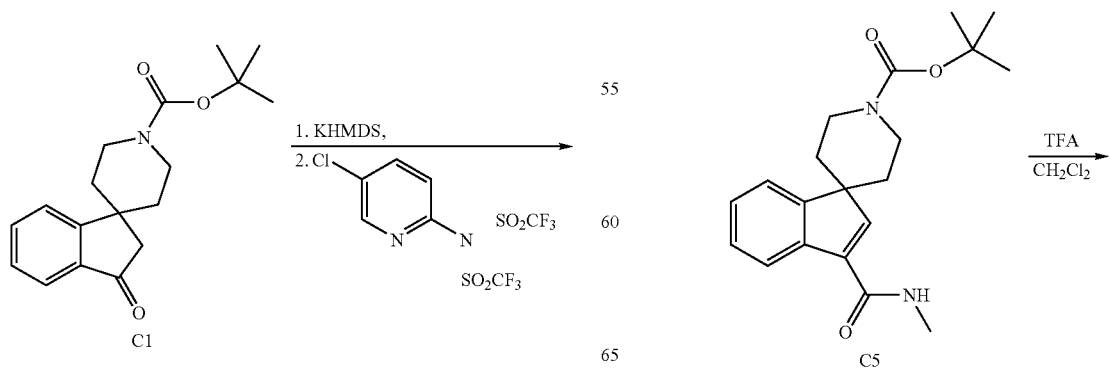
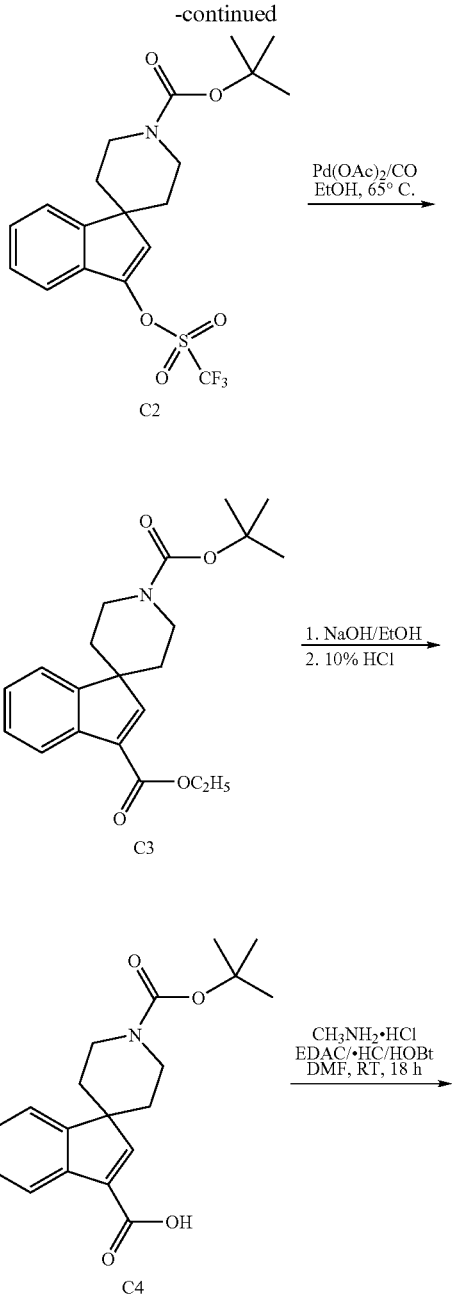

-continued

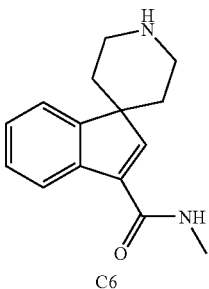

C6

To a stirred solution of tert-butyl 3-oxo-2,3-dihydrospiro[indene-1,4'-piperidine]-1'-carboxylate (C1) (2.5 g, 8.30 mmol) in THF (50 mL) at 0° C. was added KHMDS (0.5M in toluene, 21 mL, 10.37 mmol) dropwise over 10 min under nitrogen. The resulting solution was stirred at room temperature for 3 h. 2-(N,N-Bis(trifluoromethylsulfonylamine)-5-chloropyridine (4.0 g, 10.37 mmol) was added and the solution was stirred for 2 h at room temperature. The solvent was removed under reduced pressure, and the residue dissolved in water (50 mL) then extracted with EtOAc (3×50 mL). The organic layer was dried and concentrated under reduced pressure. The crude product was purified by Biotage SP1 on silica gel eluting with 7-60% EtOAc in hexanes to provide tert-butyl 3-(trifluoromethylsulfonyloxy)spiro[indene-1,4'-piperidine]-1-carboxylate (C2) as a viscous oil (3.6 g). $^1$HNMR (500 MHz, CDCl$_3$) δ 7.37 (m, 4H), 6.66 (s, 1H), 4.25 (br. m, 2H), 3.05 (m, 2H), 2.06 (ddd, 2H), 1.50 (s, 9H), 1.40 (m, 2H).

A mixture of tert-butyl 3-(trifluoromethylsulfonyloxy)spiro[indene-1,4'-piperidine]-1-carboxylate (C2) (3.4 g, 7.85 mmol), Pd(OAc)$_2$ (0.050 g, 0.22 mmol), triphenylphosphine (0.15 g, 0.57 mmol), triethylamine (2.2 mL, 16 mmol) in DMF (30 mL), and ethanol (15 mmol) was degassed and then stirred at 65° C. under carbon monoxide for 18 h. The reaction was filtered and the filtrate was concentrated under reduced pressure. The residue was dissolved in water (50 mL) and extracted with EtOAc (3×50 mL). The organic layer was dried and concentrated under reduced pressure to give the crude product which was purified by Biotage SP1 on silica gel eluting with 2-60% EtOAC in hexanes to provide 1'-tert-butyl 3-ethyl spiro[indene-1,4'-piperidine]-1,3'-dicarboxylate (C3) as a viscous oil (2.8 g). $^1$HNMR (500 MHz, CD$_3$OD) δ 7.91 (d, 1H), 7.82 (s, 1H), 7.38 (d, 1H), 7.29 (m, 2H), 4.36 (q, 2H), 4.17 (m, 2H), 3.15 (m, 2H), 2.03 (ddd, 2H), 1.50 (s, 9H), 1.38 (t, 3H), 1.25 (m, 2H).

A mixture of 1'-tert-butyl 3-ethyl spiro[indene-1,4'-piperidine]-1,3'-dicarboxylate (C3) (1.6 g, 4.48 mmol), solid NaOH (1.6 g, 40 mmol) in water (5 mL), and ethanol (25 mL) was heated at reflux for 2 h and then cooled to room temperature. The solution was concentrated and the residue was dissolved in water (25 mL). The solution was slowly acidified with 10% HCl solution. The aqueous layer was extracted with EtOAc (3×50 mL), dried and concentrated under reduced pressure to provide 1'-(tert-butyoxycarbonyl)spiro[indene-1,4'-piperidine]-3-carboxylic acid (C4) as a white solid (1.3 g). LC/MS (10-90% over 3 min with 0.9% FA) m/z 328.4 (M−1), retention time 3.2 minutes. $^1$HNMR (500 MHz, d6-DMSO) δ 12.81 (s, 1H), 7.85 (m, 2H), 7.48 (d, 1H), 7.27 (m, 2H), 4.02 (m, 2H), 3.18 (m, 2H), 1.95 (m, 2H), 1.44 (s, 9H), 1.26 (m, 2H).

A solution of methylamine in THF (2 mL) was added to a stirred solution of 1'-(tert-butyoxycarbonyl)spiro[indene-1,4'-piperidine]-3-carboxylic acid (C4) (0.51 g, 1.55 mmol), EDAC HCl (0.6 g, 3.00 mmol), HOBt (0.31 g ) in DMF (10 mL), and the solution was stirred at room temperature for 12 h. The solution was poured into water (50 mL), the aqueous layer was extracted with EtOAc (3×50 mL), dried, and concentrated under reduced pressure. The crude product was purified by Biotage SP1 on silica gel eluting with 12-100% EtOAc in hexanes to provide tert-butyl 3-(methylcarbamoyl)spiro[indene-1,4'-piperidine]-1'-carboxylate (C5) as a white solid (0.45 g). LC/MS (10-90% over 3 min with 0.9% FA) m/z 343 (M+1), R$_t$ 3.0 minutes. $^1$HNMR (500 mHz, CDCl$_3$) δ 7.73 (d, 1H), 7.23 (m, 3H), 7.14 (s, 1H), 6.05 (brm, 1H), 4.11 (m, 2H), 3.03 (m, 2H), 2.93 (d, 3H), 1.95 (m, 2H), 1.44 (s, 9H), 1.30 (m, 2H).

Trifluoroacetic acid (2 mL) was added to a stirred solution of tert-butyl 3-(methylcarbamoyl)spiro[indene-1,4'-piperidine]-1'-carboxylate (C5) (0.45 g, 1.30 mmol) in dichloromethane (5 mL) and the solution was stirred at room temperature for 1 h. The solvent was removed under reduced pressure and dried under high vacuum for 18 h to provide N-methylspiro[indene-1,4'-piperidine]-3-carboxamide (C6) as an oil (0.46 g). LC/MS (10-90% over 3 min with 0.9% FA) m/z 243 (M+1), R$_t$ 1.2 minutes.

Method C: Synthesis of 1'-(3,3-dimethylbutyl)-N-methylspiro[indene-1,4'-piperidine]-3-carboxamide (Compound No. 27)

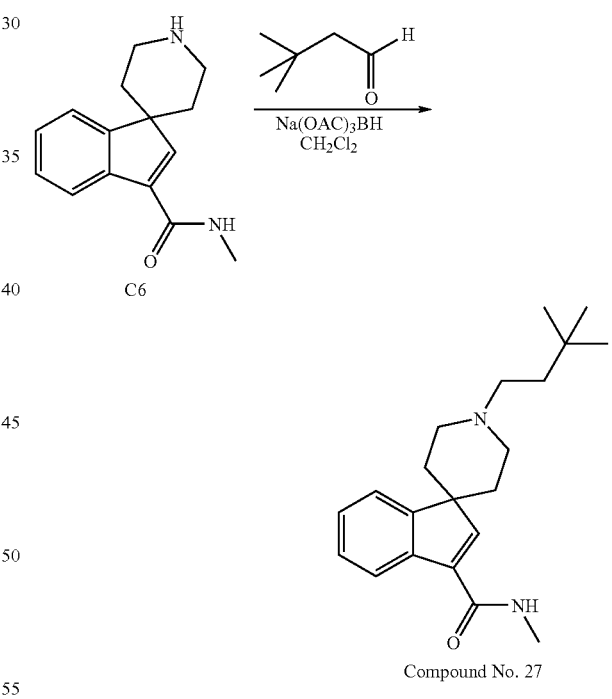

Compound No. 27

Sodium triacetoxyborohydride (0.013 g, 0.073 mmol) was added to a stirred a solution of (C6) (0.015 g, 0.073 mmol) and 3-3-dimethylbutyraldehyde (0.0126 g, 0.126 mmol) in dichloroethane (1 mL), and the resulting solution was stirred at room temperature for 2 h. The solvent was evaporated and the product was purified by reverse phase preparative HPLC to afford Compound No. 27 as a TFA salt (0.012 g). LC/MS (10-90% over 3 min with 0.9% FA) m/z 327.2 (M+1), retention time 1.9 minutes. $^1$HNMR (500 MHz, CD$_3$OD): 7.73 (d, 1H), 7.31-7.40 (m, 4H), 3.77 (m, 2H), 3.30 (m, 4H), 2.91 (s, 3H), 2.46 (m, 2H), 1.73 (m, 2H), 1.59 (m, 2H), 1.03 (s, 9H).

Method D: Synthesis of 1'-(bicyclo[2.2.1]heptan-2-yl)-N-methylspiro[indene-1,4'-piperidine]-3-carboxamide (Compound No. 38)

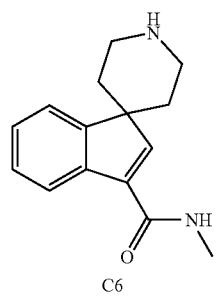

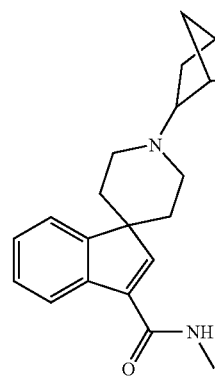

Compound No. 38

A mixture of (C6) (0.015 g, 0.073 mmol), titanium (IV) isopropoxide (0.065 mL, 0.22 mmol) and (1R,4S)-bicyclo[2.2.1]heptan-2-one (3 eq) was stirred at room temperature for 18 h in dichloroethane (0.5 mL). Sodium triacetoxyborohydride (0.013 g, 0.073 mmol) was added and the reaction stirred at room temperature for 1 h. The solvent was evaporated and 6N NaOH (0.5 mL) and methanol (1 mL) was added and triturated to give a white solid. The solid was washed with methanol (1 mL) and EtOAc (1 mL). The filtrate was concentrated under reduced pressure to afford the crude product that was purified by reverse phase preparative HPLC to afford 1'-(bicyclo[2.2.1]heptan-2-yl)-N-methylspiro[indene-1,4'-piperidine]-3-carboxamide (Compound No. 38) (0.012 g) as an oil. LC/MS (10-90% over 3 min with 0.9% FA) m/z 337.2 (M+1), $R_t$ 1.7 minutes. $^1$HNMR (500 MHz, CD$_3$OD): δ 7.74 (d, 1H), 7.35 (m, 4H), 3.73 (m, 2H), 3.55 (m, 1H), 3.30 (m, 2H), 2.91 (s, 3H), 2.42-2.74 (m, 5H), 2.19 (m, 2H), 1.54-1.74 (m, 8H), 1.31 (m, 1H)

The examples in Table 3 generally follow the synthetic preparations and methods described above in Preparation C and Methods C-D using appropriate reagents; however, these preparation and methods are only exemplary, and other suitable preparations and methods may be used.

TABLE 3

Exemplary compounds synthesized following preparation C and methods C-D.

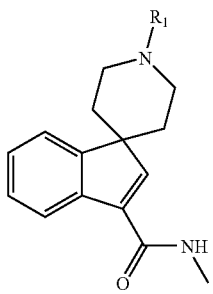

| Example No. | Compound No. | R$_1$ | Method |
|---|---|---|---|
| 15 | 27 |  | C |
| 16 | 69 | 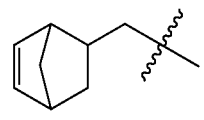 | C |
| 17 | 6 | 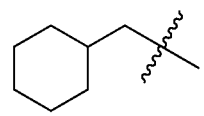 | C |
| 18 | 15 | 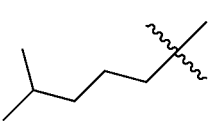 | C |
| 19 | 8 | 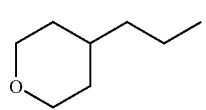 | C |
| 20 | 49 | 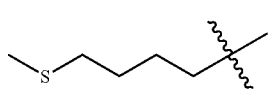 | C |
| 21 | 19 | 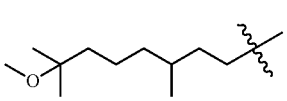 | C |
| 22 | 9 | 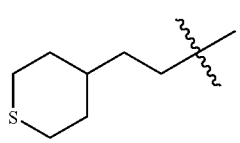 | C |

TABLE 3-continued

Exemplary compounds synthesized following preparation C and methods C-D.

| Example No. | Compound No. | R₁ | Method |
|---|---|---|---|
| 23 | 58 | cyclohexyl | D |
| 24 | 41 | cycloheptyl | D |
| 25 | 38 | bicyclic (norbornyl) | D |
| 26 | 65 | 1-(ethoxycarbonyl)piperidin-4-yl | D |

Preparation D: Synthesis of spiro[indene-1,4'-piperidine]-3-carboxylic acid

Trifluoroacetic acid (2 mL) was added to a stirred solution of 1'-(tert-butyoxycarbonyl)spiro[indene-1,4'-piperidine]-3-carboxylic acid (C4) (0.25 g, 0.76 mmol) in dichloromethane (5 mL) and the solution was stirred at room temperature for 1 h. The solvent was removed under reduced pressure and dried under high vacuum for 18 h to provide spiro[indene-1,4'piperidine]-3-carboxylate (D1) as an oil (0.26 g, quantitative, TFA salt). LC/MS (10-90% over 3 min with 0.9% FA) m/z 230.3 (M+1), R$_t$ 1.3 minutes. ¹HNMR (500 MHz, DMSO-d6): 12.91 (brs, 1H), 7.95 (s, 1H), 7.88 (d, 1H), 7.35 (m, 3H), 3.31-3.43 (m, 4H), 2.27 (m, 2H), 1.42 (m,2H).

Method E: Synthesis of 1'-(3,3-dimethylbutyl)spiro[indene-1,4'-piperidine]-3-carboxylic acid (Compound No. 20)

-continued

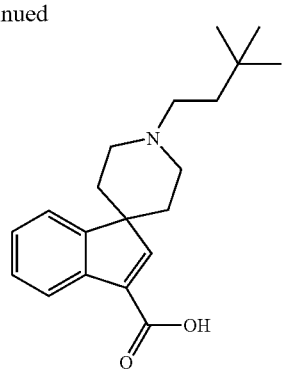

Compound No. 20

Sodium triacetoxyborohydride (0.28 g, 1.34 mmol) was added to a stirred a solution of (D1) (0.38 g, 1.12 mmol) and 3-3-dimethylbutyraldehyde (0.134 g, 1.34 mmol) in dichloromethane (5 mL) and the resulting suspension was heated at 70° C. for 18 h. The solvent was evaporated and the crude product was dissolved in water (10 mL). The aqueous layer was extracted with EtOAc (4×25 mL), dried and concentrated under reduced pressure to afford 1'-(3,3-dimethylbutyl)spiro[indene-1,4'-piperidine]-3-carboxylic acid (Compound No. 20) (0.21 g). The analytical sample was prepared by reverse preparative HPLC. LC/MS (10-90% over 3 min with 0.9% FA) m/z 314.1 (M+1), retention time 2.0 minutes.

Method F: Synthesis of 1'-(bicyclo[2.2.1]heptan-2-yl)spiro[indene-1,4'-piperidine]-3-carboxylic acid (Compound No. 48)

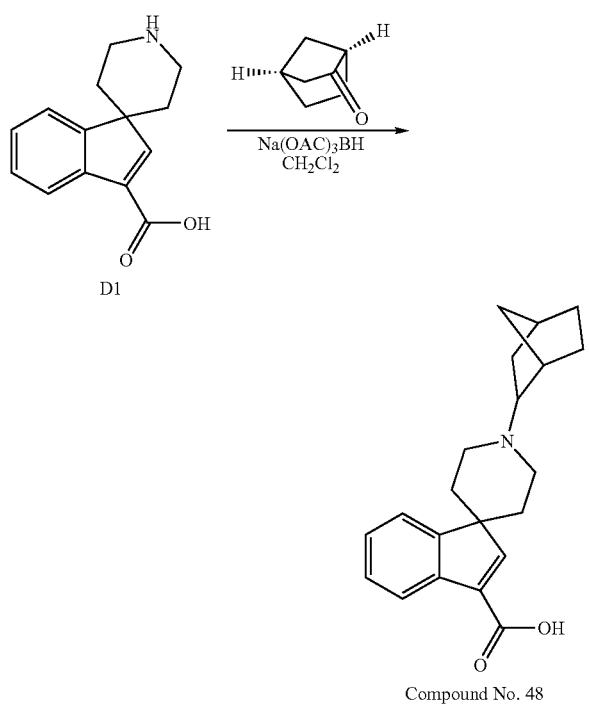

A mixture of compound (D1) (0.020 g, 0.058 mmol), titanium (IV) isopropoxide (0.052 mL, 0.174 mmol), and (1R,4S)-bicyclo[2.2.1]heptan-2-one (3 eq) was stirred at room temperature for 18 h in dichloroethane (0.5 mL). Sodium triacetoxyborohydride (0.012 g, 0.058 mmol) was added and stirred at room temperature for 1 h. The solvent was evaporated and 6N NaOH (0.5 mL) and methanol (1 mL) was added and then triturated to form a white solid. The solid was washed with methanol (1 mL) and EtOAc (1 mL). The filtrate was concentrated under reduced pressure to afford the crude product which was purified by reverse phase preparative HPLC to afford 1'-(bicyclo[2.2.1]heptan-2-yl)spiro[indene-1,4'-piperidine]-3-carboxylic acid (Compound No. 48) (0.002 g). LC/MS (10-90% over 3 min with 0.9% FA) m/z 324.1 (M+1), $R_t$ 1.9 minutes.

The examples in Table 4 generally follow the synthetic preparations and methods described above in Preparation D and Methods E-F using appropriate reagents; however, these preparation and methods are only exemplary, and other suitable preparations and methods may be used.

TABLE 4

Exemplary compounds synthesized following preparation D and methods E-F.

| Example No. | Compound No. | $R_1$ | Method |
|---|---|---|---|
| 27 | 2 | norbornylmethyl | E |
| 28 | 54 | cyclohexylmethyl | E |
| 29 | 12 | cycloheptyl | F |
| 30 | 48 | bicyclo[2.2.1]heptan-2-yl | F |

TABLE 4-continued

Exemplary compounds synthesized following preparation D and methods E-F.

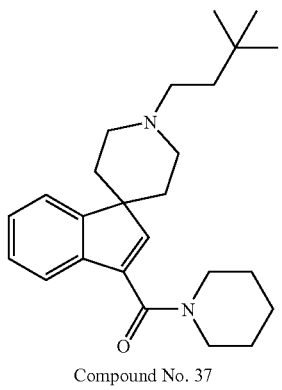

| Example No. | Compound No. | $R_1$ | Method |
|---|---|---|---|
| 31 | 21 | (ethyl carbamate piperidin-4-yl) | F |
| 32 | 13 | (ethyl carbamate bicyclic) | F |

Preparation E: Synthesis of 1'-(3,3-dimethylbutyl)spiro[indene-1,4'-piperidine]-3-yl)(piperidin-1-yl)methanone (Compound No. 37)

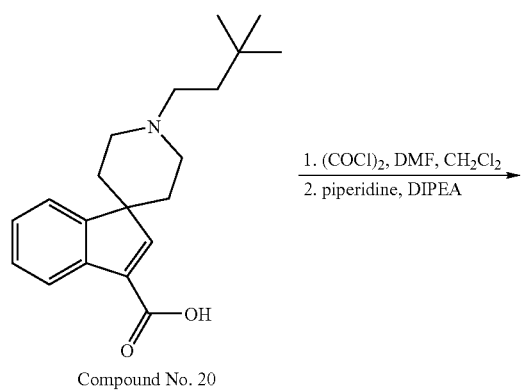

Compound No. 20

1. (COCl)$_2$, DMF, CH$_2$Cl$_2$
2. piperidine, DIPEA

→

Compound No. 37

A solution oxalyl chloride in dichloromethane (2M, 0.05 mL, 0.1 mmol) was added to a stirred solution of 1'-(3,3-dimethylbutyl)spiro[indene-1,4'-piperidine]-3-carboxylic acid (0.020 g, 0.064 mmol) in dichloromethane (0.5 mL) and DMF (0.05 mL)$_p$; and the solution was stirred at room temperature for 30 min. Diisopropylethylamine (0.1 mL) and piperidine (0.1 mL) were added. The solution was stirred at room temperature for 2 hr and concentrated under reduced pressure. The crude product was purified by reverse phase preparative HPLC to afford 1'-(3,3-dimethylbutyl)spiro[indene-1,4'-piperidine]-3-yl)(piperidin-1-yl)methanone (Compound No. 37) (0.014 g). LC/MS (10-90% over 3 min with 0.9% FA) m/z 381.3 (M+1), R$_t$ 2 minutes. $^1$HNMR (500 MHz, CD$_3$OD): 7.31-7.43 (m, 4H), 7.08 (s, 1H), 3.76 (m, 4H), 3.56 (m, 2H), 3.44 (m, 2H), 3.30 (m, 2H), 2.47 (m, 2H), 1.53-1.75 (m, 10H), 1.03 (s,9H).

The examples in Table 5 generally follow the synthetic preparations and methods described above in Preparation E using appropriate reagents; however, these preparation and methods are only exemplary, and other suitable preparations and methods may be used.

TABLE 5

Exemplary compounds synthesized following preparation E.

| Example No. | Compound. No. | $R_1$ | $R_{2a}$ | $R_{2b}$ |
|---|---|---|---|---|
| 33 | 39 | (3,3-dimethylbutyl) | H | (isobutyl) |

TABLE 5-continued

Exemplary compounds synthesized following preparation E.

| Example No. | Compound. No. | R₁ | R₂ₐ | R₂ᵦ |
|---|---|---|---|---|
| 34 | 70 | neopentyl-CH | H | isopropyl |
| 35 | 77 | neopentyl-CH | H | cyclopentyl |
| 36 | 25 | neopentyl-CH | H | cyclohexyl |
| 37 | 56 | neopentyl-CH | H | CH₂-N(CH₃)₂ |
| 38 | 50 | norbornyl-CH₂ | H | 2-methylpentyl |
| 39 | 30 | norbornyl-CH₂ | H | 3-pentyl |
| 40 | 67 | norbornyl-CH₂ | H | CH₂-N(CH₃)₂ |

TABLE 5-continued

Exemplary compounds synthesized following preparation E.

| Example No. | Compound. No. | R₁ | R₂ₐ | R₂ᵦ |
|---|---|---|---|---|
| 41 | 66 | norbornenyl-CH₂ | H | isopropyl |
| 42 | 32 | norbornenyl-CH₂ | H | cyclopropyl |
| 43 | 47 | norbornenyl-CH₂ | H | cyclobutyl |

Preparation F: Synthesis of N-(pentan-3-yl)spiro[indene-1,4'-piperidine]-3-carboxamide (F2)

C4 + NH₂-pentan-3-yl → (EDAC·HC/HOBt, DMF, RT)

-continued

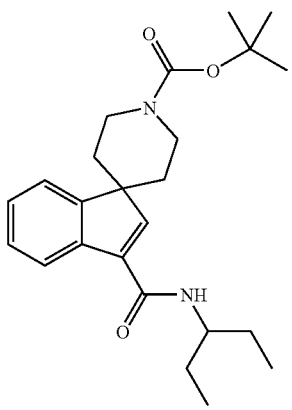

F1

 TFA / CH$_2$Cl$_2$ →

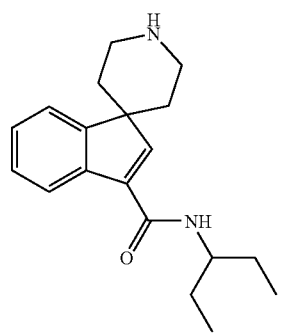

F2

Method G: cl Synthesis of 1'-(cyclohexylmethyl)-N-(pentan-3-yl)spiro[indene-1,4'-piperidine]-3-carboxamide (Compound No. 68)

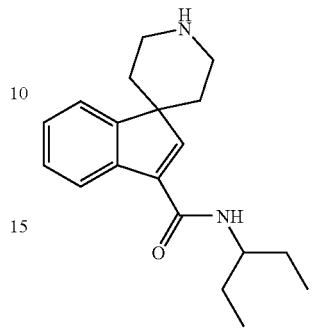 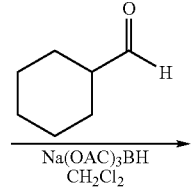 Na(OAc)$_3$BH / CH$_2$Cl$_2$ →

F2

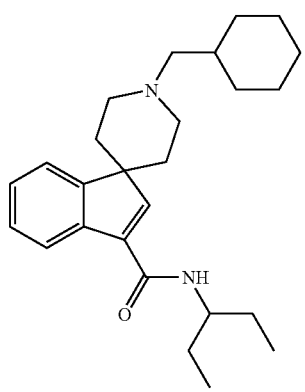

Compound No. 68

A solution of 1-ethylpropylamine (0.5 mL) was added to a stirred solution of compound (C4) (0.50 g, 1.52 mmol), EDAC.HCl (0.6 g, 3.00 mmol), HOBt (0.31 g, 2.32 mmol) in DMF (10 mL) and the solution was stirred at room temperature for 2 h. The solution was poured into water (50 mL) and the aqueous layer was extracted with EtOAc (3×50 mL), dried over Na2SO4 and concentrated under reduced pressure. The crude product was purified by Biotage SP1 on silica gel eluting with 5-70% EtOAc in hexanes to provide tert-butyl 3-(pentan-3-ylcarbamoyl)spiro[inden-1,4'-piperidine]-1'-carboxylate (F1) as a white solid (0.6 g). LC/MS (10-90% over 3 min with 0.9% FA) m/z 399 (M+1), R$_t$ 3.66 minutes. $^1$HNMR (500 MHz, DMSO-d6) δ 7.78 (d, 1H), 7.55 (m, 1H), 7.43 (d, 1H), 7.23 (br m, 1H), 4.07 (m, 2H), 3.75 (m,1H), 3.15 (m, 2H), 1.98 (d, 2H), 1.55 (m, 2H), 1.45 (s, 9H), 1.25 (m,2H), 0.88 (m, 6H).

Trifluoroacetic acid (5 mL) was added to a stirred solution of compound (F1) (0.60 g, 1.50 mmol) in dichloromethane (10 mL) and the solution was stirred at room temperature for 1 h. The solvent was removed under reduced pressure and dried under high vacuum for 18 h to provide N-(pentan-3-yl)spiro[indene-1,4'-piperidine]-3-carboxamide (F2) as an oil (0.62 g). LC/MS (10-90% over 3 min with 0.9% FA) m/z 299 (M+1) R$_t$ 1.9 minutes.

Sodium triacetoxyborohydride (0.011 g, 0.05 mmol) was added to a stirred a solution of 9 (0.020 g, 0.05 mmol) and cyclohexanecarboxaldehyde (0.017 g, 0.15 mmol) in dichloromethane (5 mL) and the resulting suspension was stirred at room temperature for 18 h. The solvent was evaporated and the crude product was purified by reverse phase preparative HPLC to afford 1'-(cyclohexylmethyl)-N-(pentan-3-yl)spiro[indene-1,4'-piperidine]-3-carboxamide (Compound No. 68). LC/MS (10-90% over 3 min with 0.9% FA) m/z 314.1 (M+1), R$_t$ 2.0 minutes. R$_t$ 2.3 minutes.

Method H: Synthesis of 1'-(bicyclo[2.2.1]heptan-2-yl)-N-(pentan-3-yl)spiro[indene-1,4'-piperidine]-3-carboxamide (Compound No. 14)

A mixture of (F2) (0.020 g, 0.05 mmol), titanium (IV) isopropoxide (0.045 mL, 0.15 mmol) and (1R,4S)-bicyclo[2.2.1]heptan-2-one (3 eq) was stirred at room temperature for 18 h in dichloroethane (0.5 mL). Sodium triacetoxyborohydride (0.011 g, 0.050 mmol) was added and the mixture stirred at room temperature for 1 h. The solvent was evaporated and 6N NaOH (0.5 mL) and methanol (1 mL) was added and then triturated to give a white solid that was washed with methanol (1 mL) and EtOAc (1 mL). The filtrate was concentrated under reduced pressure to afford the crude product which was purified by reverse phase preparative HPLC to afford 1'-(bicyclo[2.2.1]heptan-2-yl)-N-(pentan-3-yl)spiro[indene-1,4'-piperidine]-3-carboxamide (Compound No. 14) (0.013 g). LC/MS (10-90% over 3 min with 0.9% FA) m/z 324.1 (M+1), retention time 2.2 minutes.

Method I: Synthesis of tert-butyl 4-(3-(pentan-3-ylcarbamoyl)spiro[indene-1,4'-piperidine]-1'-yl)piperidine-1-carboxylate (Compound No. 1)

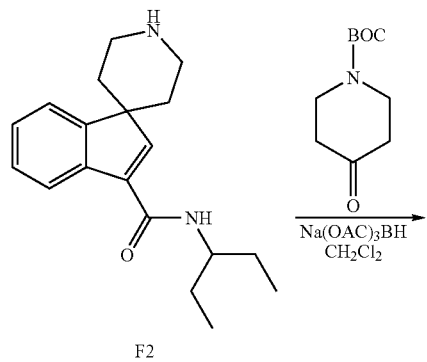

F2

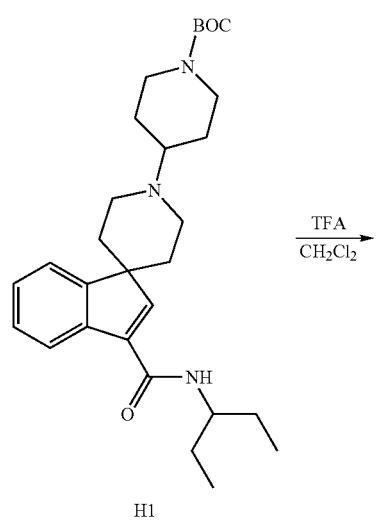

H1

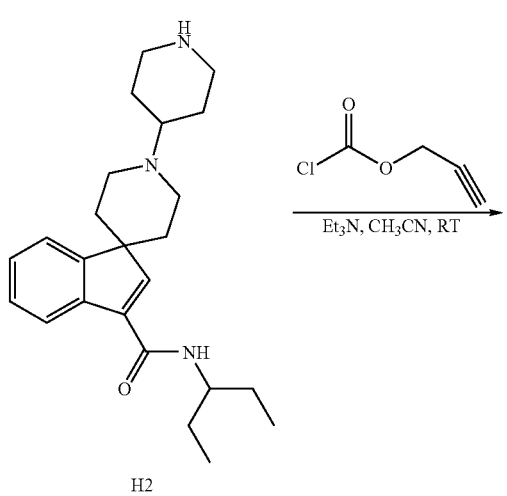

H2

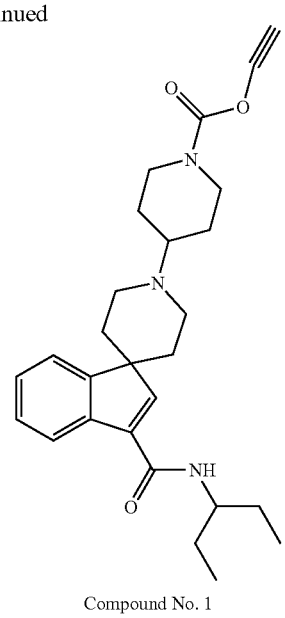

Compound No. 1

A mixture of compound (F2) (0.29 g, 0.71 mmol), tert-butyl-4-oxo-1-piperidinecarboxylate (0.175 g, 0.88 mmol), Na(OAc)$_3$BH (0.19 g, 0.88 g) in dichloromethane (5 mL) was heated at 70° C. for 24 h. The reaction mixture was cooled room temperature and concentrated. The residue was dissolved in water (10 mL) and basified with saturated NaHCO$_3$. The aqueous layer was extracted with EtOAc (3×10 mL), dried, and concentrated to give tert-butyl 4-(3-(pentan-3-ylcarbamoyl)spiro[indene-1,4'-piperidine]-1'-yl)piperidine-1-carboxylate (H1) as an oil (0.25 g). LC/MS (10-90% over 3 min with 0.9% FA) m/z 482 (M+1).

Trifluoroacetic acid (2 mL) was added to a stirred solution of compound (H1) (0.24 g, 0.50 mmol) in dichloromethane (5 mL) and the solution was stirred at room temperature for 1 h. The solvent was removed under reduced pressure and dried under vacuum for 18 h to provide N-(pentan-3-yl)-1'-(piperidin-4-yl)spiro[indene-1,4'-piperidine]-3-carboxamide (H2) as an oil (0.49 g, 100%, TFA salt). LC/MS (10-90% over 3 min with 0.9% FA) m/z 382.3 (M+1) R$_t$, 1.7 minutes Propargyl chloroformate (0.005 g, 0.045 mmol) was added to a stirred solution of TFA salt of (H2) (0.015 g, 0.03 mmol) in CH$_3$CN (0.5 mL) and Et$_3$N (0.1 mL) and the solution was stirred at room temperature for 2 h. The solvent was removed under reduced pressure and the residue was purified by reverse phase preparative HPLC to afford tert-butyl 4-(3-(pentan-3-ylcarbamoyl)spiro[indene-1,4'-piperidine]-1'-yl) piperidine-1-carboxylate (Compound No. 1) (0.006 g). LC/MS (10-90% over 3 min with 0.9% TFA) m/z 464.2 (M+1), retention time 2.2 minutes. $^1$HNMR (500 MHz, CD$_3$OD) δ 7.70 (d, 1H), 7.32-7.40 (m, 4H), 4.73 (m, 2H), 4.36 (m, 2H), 3.85 (m, 1H), 3.75 (m, 2H), 3.42 (m, 3H), 2.94 (m, 1H), 2.93 (t, 1H), 2.49 (m, 2H), 1.50-1.80 (m, 8H), 1.00 (t, 6H).

The examples in Table 6 generally follow the synthetic preparations and methods described above in Preparation F and Methods G-I using appropriate reagents; however, these preparation and methods are only exemplary, and other suitable preparations and methods may be used.

TABLE 6
Exemplary compounds synthesized following preparation F and methods G-I.
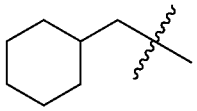
| Example No. | Compound No. | R₁ | Method |
|---|---|---|---|
| 44 | 68 | 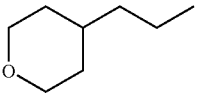 | G |
| 45 | 40 | 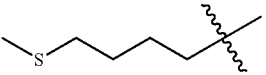 | G |
| 46 | 53 | 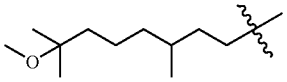 | G |
| 47 | 55 | 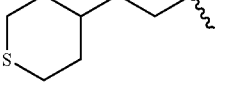 | G |
| 48 | 23 | 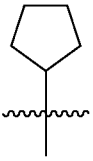 | G |
| 49 | 76 | 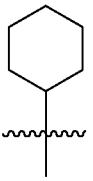 | G |
| 50 | 17 | 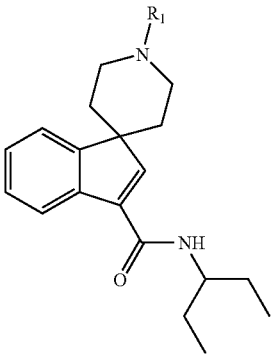 | H |
| 51 | 73 |  | H |
TABLE 6-continued
Exemplary compounds synthesized following preparation F and methods G-I.
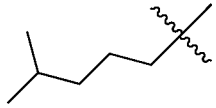
| Example No. | Compound No. | R₁ | Method |
|---|---|---|---|
| 52 | 3 |  | H |
| 53 | 14 |  | H |
| 54 | 28 | 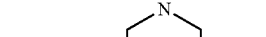 | H |
| 55 | 75 | 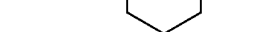 | H |

TABLE 6-continued

Exemplary compounds synthesized following preparation F and methods G-I.

| Example No. | Compound No. | R₁ | Method |
|---|---|---|---|
| 56 | 71 | ethyl carbamate (pyrrolidine-type) | I |
| 57 | 42 | propyl piperidine-1-carboxylate | I |
| 58 | 24 | allyl piperidine-1-carboxylate | I |
| 59 | 22 | isobutyryl piperidine | I |
| 60 | 33 | N,N-dimethylpiperidine-1-carboxamide | I |
| 61 | 45 | cyclopropanecarbonyl piperidine | I |
| 62 | 10 | acetyl piperidine | I |
| 63 | 18 | morpholine-4-carbonyl piperidine | I |

A person skilled in the chemical arts can use the examples and schemes along with known synthetic methodologies to synthesize compounds of the present invention, including the compounds in Table 7 below.

TABLE 7

Physical Characteristics of compounds in Table 1.

| Cmd No. | LCMS_Plus | LCMS_RT | NMR |
|---|---|---|---|
| 2 | 336.2 | 2 | |
| 3 | 395.3 | 2.3 | |
| 5 | 478.3 | 1.76 | |
| 6 | 339.2 | 1.9 | CD$_3$OD: 7.73 (d, 1H), 7.31-7.39 (m, 4H), 3.75 (m, 2H), 3.10 (d, 2H), 2.91 (s, 3H), 2.54 (m, 2H), 1.80-1.89 (m, 7H), 1.73 (m, 1H), 1.17-1.41 (m, 5H) |
| 7 | 382.3 | 1.7 | |
| 8 | 355.2 | 1.56 | |
| 9 | 371.2 | 1.8 | |
| 10 | 424.3 | 1.9 | CD$_3$OD: 7.71 (d, 1H), 7.30-7.40 (m, 4H), 4.16 (m, 2H), 3.90 (m, 1H), 3.61-3.80 (m, 3H), 3.43 (m, 2H), 3.23 (m, 1H), 2.70 (m, 1H), 2.49 (m, 2H), 2.26 (m, 2H), 2.15 (s, 6H), 1.50-1.85 (m, 8H), 0.99 (t, 6H) |
| 11 | 381.3 | 1.79 | DMSO (d6): 9.04 (br.s, 1H), 7.37 (d, 1H), 7.34 (t, 1H), 7.26 (t, 1H), 7.04 (d, 1H), 6.05 (t, 1H), 3.45 (t, 4H), 3.21 (t, 2H), 3.18-3.12 (m, 4H), 2.57 (d, 2H), 2.04 (td, 2H), 1.91 (d, 2H), 1.85 (dt, 2H), 1.79 (dt, 2H), 1.55-1.51 (m, 2H), 0.92 (s, 9H). |
| 12 | 326.1 | 2 | |
| 13 | 411.2 | 1.9 | |
| 15 | 313.2 | 1.8 | |
| 16 | 382.3 | 1.7 | |
| 17 | 367.27 | 2.1 | |
| 18 | 495.3 | 2 | |
| 19 | 412.3 | 2.1 | |
| 21 | 385.1 | 1.8 | |
| 22 | 452.3 | 2 | |
| 23 | 469.3 | 2.4 | |
| 24 | 466.3 | 2.2 | |
| 25 | 395.3 | 2.3 | |
| 26 | 369.3 | 2.2 | CD$_3$OD: 7.25-7.45 (m, 4H), 7.07 (s, 1H), 3.78 (m, 2H), 3.59 (m, 2H), 3.26-3.38 (m, 6H), 2.48 (m, 2H), 1.73 (m, 2H), 1.62 (m, 2H), 1.27 (m, 3H), 1.15 (m, 3H), 1.05 (s, 9H) |
| 28 | 454.3 | 2.1 | |
| 29 | 391.3 | 1.71 | DMSO (d6): 8.59 (br.s, 1H), 7.40 (d, 1H), 7.35 (t, 1H), 7.26 (t, 1H), 7.05 (d, 1H), 6.04 (t, 1H), 3.45 (t, 4H), 3.21 (t, 2H), 3.34 (dd, 1H), 2.57 (d, 2H), 2.29 (br. s, 1H), 2.22 (td, 1H), 2.13 (td, 1H), 2.07-1.66 (m, 9H), 1.62-1.33 (m, 5H), 1.16 (m, 1H). |
| 30 | 405.2 | 2.3 | |
| 31 | 405.2 | 2.3 | |
| 32 | 375.2 | 2 | CD$_3$OD: 7.74 (d, 1H) 7.31-7.38 (m, 4H), 6.32 (m, 1H), 6.08 (m, 1H), 3.78 (m, 2H), 3.13 (m, 1H), 3.04 (m, 1H), 2.80-2.90 (m, 3H), 2.50-2.60 (m, 3H), 2.13 (m, 1H), 1.54 (m, 3H), 1.40 (m, 2H), 0.82 (m, 3H), 0.63 (m, 2H) |
| 33 | 453.3 | 2 | CD$_3$OD: 7.71 (d, 1H), 7.32-7.40 (m, 4H), 3.75-3.90 (m, 5H), 3.40-3.55 (m, 3H), 2.92 (m, 2H), 2.87 (s, 6H), 2.50 (m, 2H), 2.19 (m2H), 1.82 (m, 2H), 1.67 (m, 4H), 1.53 (m, 2H), 0.99 (t, 6H) |
| 34 | 403.2 | 1.79 | DMSO (d6): 9.01 (br. s, H), 7.38 (d, 1H), 7.34 (t, 1H), 7.26 (t, 1H), 7.04 (d, 1H), 6.26 (td, 0.6H), 6.15 (t, 0.7H), 6.07-6.03 (m, 1.7H), 3.45 (t, 4H), 3.27-3.20 (m, 5H), 2.96-2.76 (m, 4H), 2.58-2.56 (m, 2H), 2.11 (q, 2H), 1.99 (ddd, 1H), 1.90-1.74 (m, 6H), 1.35 (dd, 2H), 0.67 (dt, 1H). |
| 35 | 319.1 | 1.79 | DMSO (d6): 8.72 (br.s, 1H), 7.48-7.40 (m, 4H), 7.11 (t, 1H), 3.57-3.53 (m, 2H), 3.36 (dd, 2H), |

TABLE 7-continued

Physical Characteristics of compounds in Table 1.

| Cmd No. | LCMS_Plus | LCMS_RT | NMR |
|---|---|---|---|
| | | | 3.26-3.14 (m, 2H), 2.78 (d, 2H), 2.18 (dt, 2H), 1.99 (t, 1H), 1.85 (t, 2H), 1.62-1.53 (m, 4H), 1.42-1.31 (m, 3H), 1.17 (d, 1H). |
| 36 | 379.3 | 1.7 | |
| 39 | 383.3 | 2.3 | |
| 40 | 369.2 | 2.2 | |
| 41 | 339.2 | 1.8 | |
| 42 | 468.3 | 2.2 | |
| 43 | 452.3 | 1.68 | DMSO (d6): 9.07 (br.s, 1H), 7.38 (d, 1H), 7.34 (t, 1H), 7.26 (t, 1H), 7.04 (d, 1H), 6.03 (t, 1H), 4.10 (m, 2H), 4.01 (q, 2H), 3.77 (t, 4H), 3.45 (t, 4H), 3.21 (m, 2H), 3.00 (m, 1H), 2.55 (d, 2H), 2.36 (t, 2H), 1.94 (d, 2H), 1.84 (q, 2H), 1.79 (q, 2H), 1.70-1.65 (m, 2H), 1.55 (qd, 2H), 1.16 (t, 3H). |
| 44 | 353.2 | 1.9 | |
| 45 | 450.3 | 2 | CD$_3$OD: 7.71 (d, 1H), 7.32-7.40 (m, 4H), 4.51 (m, 1H), 3.40-3.90 (m, 4H), 3.42 (m, 4H), 2.70 (m1H), 2.45 (m2H), 2.25 (m, 2H), 2.03 (m, 2H), 1.67 (m, 4H), 1.52 (m, 2H), 0.99 (t, 6H), 0.83-0.89 (m4H) |
| 46 | 355.2 | 1.69 | DMSO (d6): 9.13 (br.s, 1H), 7.38 (d, 1H), 7.34 (t, 1H), 7.26 (t, 1H), 6.95 (d, 1H), 5.98 (t, 1H), 3.46 (d, 2H), 3.19 (q, 2H), 3.14 (m, 2H), 2.98 (s, 3H), 2.86 (s, 3H), 2.59 (d, 2H), 2.05 (td, 2H), 1.90 (d, 2H), 1.58-1.55 (m, 2H), 0.92 (s, 9H). |
| 47 | 389.2 | 2.2 | |
| 49 | 345.1 | 1.7 | |
| 50 | 405.2 | 2.4 | CD$_3$OD: 7.69 (d, 1H), 7.31-7.38 (m, 4H), 6.32 (m, 1H), 6.08 (m, 1H), 4.11 (m, 1H), 3.78 (m, 2H), 3.14 (m, 1H), 3.04 (m, 1H), 2.93 (m, 2H), 2.45-2.60 (m, 3H), |

TABLE 7-continued

Physical Characteristics of compounds in Table 1.

| Cmd No. | LCMS_Plus | LCMS_RT | NMR |
|---|---|---|---|
| | | | 2.14 (m, 1H), 1.43-1.60 (m, 9H), 1.24 (d, 3H), 0.97 (t, 3H), 0.82 (m, 1H) |
| 52 | 369.2 | 1.81 | |
| 53 | 411.3 | 2 | |
| 54 | 326.1 | 2.1 | |
| 55 | 401.2 | 2.2 | |
| 56 | 341.22 | 1.65 | CD$_3$OD: 7.32-7.43 (m, 4H), 7.12 (s, 1H), 3.77 (m, 2H), 3.30 (m, 4H), 3.14 (s, 3H), 3.06 (s, 3H), 2.46 (m, 2H), 1.72 (m, 2H), 1.64 (m, 2H), 1.03 (s, 9H |
| 57 | 299.2 | 1.7 | |
| 58 | 325.2 | 1.7 | |
| 59 | 353.2 | 1.9 | |
| 60 | 412.2 | 1.7 | |
| 61 | 339.2 | 1.8 | |
| 62 | 342.2 | 2.3 | CD$_3$OD: 7.96 (d, 1H), 8.90 (s, 1H), 7.33-7.41 (m, 3H), 4.37 (q, 2H), 3.75 (m, 2H), 3.36 (m, 2H), 2.49 (m, 2H), m1.72 (m, 2H), 1.62 (m, 2H), 1.40 (t, 3H), 1.04 (s, 9H) |
| 63 | 380.2 | 1.76 | DMSO (d6): 9.20 (br.s, 1H), 7.49-7.20 (m, 4H), 7.09 (t, 1H), 4.10 (d, 2H), 4.04 (q, 2H), 3.42 (m, 3H), 3.22 (q, 2H), 2.82 (m, 2H), 2.76 (m, 2H), 2.07 (d, 4H), 1.90 (d, 2H), 1.54 (qd, 2H), 1.19 (t, 3H). |
| 64 | 351.2 | 1.8 | |
| 65 | 397.2 | 1.7 | CD$_3$OD: 7.74 (d, 1H), 7.30-7.42 (m, 4H), 4.35 (m, 2H) < 4.14 (q, 2H), 3.75 (m, 2H), 3.55 (m, 1H), 3.38 (m, 2H), 2.89 (m, 5H), 2.50 (m, 2H), 2.22 (m, 2H), 1.72 (m, 2H), 1.63 (m, 2H), 1.28 (t, 3H) |
| 66 | 377.2 | 2.1 | CD$_3$OD: 7.72 (d, 1H), 7.31-7.39 (m, 4H), 6.32 (m, 1H), 6.08 (m, 1H), 4.19 (m, 1H), 3.79 (m, 2H), 3.15 (m, 1H), 3.04 (m, 1H), 2.92 (m, 2H), 2.50-2.65 (m, 3H), |

TABLE 7-continued

Physical Characteristics of compounds in Table 1.

| Cmd No. | LCMS_Plus | LCMS_RT | NMR |
|---|---|---|---|
|  |  |  | 2.04 (m, 1H),<br>1.53-1.60 (m, 4H),<br>1.41 (m, 2H),<br>1.25 (d, 6H),<br>0.80 (m, 1H). |
| 67 | 363.2 | 1.9 |  |
| 69 | 349 | 1.9 | CD$_3$OD:<br>7.73 (d, 1H),<br>7.31-7.39 (m, 4H),<br>6.32 (m, 1H),<br>6.08 (m, 1H),<br>3.78 (m, 2H),<br>2.95-3.15 (m, 4H),<br>2.90 (s, 3H),<br>2.51 (m, 2H),<br>2.15 (m, 1H),<br>1.25-1.60 (m4H),<br>0.89 (m, 1H) |
| 70 | 355.3 | 2.1 |  |
| 71 | 440.3 | 2 |  |
| 72 | 440.3 | 1.65 |  |
| 73 | 381.2 | 2.2 |  |
| 74 | 365.2 | 1.58 | DMSO (d6):<br>8.72 (br.s, 1H),<br>7.40 (d, 1H), 7.35 (t, 1H), 7.27 (t, 1H),<br>6.96 (d, 1H),<br>5.98 (t, 1H),<br>3.51 (m, 1H), 3.41 (d, 1H), 3.34 (d, 1H),<br>3.26-3.14 (m, 2H), 2.98 (s, 3H), 2.86 (s, 3H), 2.59 (br.s, 2H), 2.25 (td, 1H), 2.16 (td, 1H),<br>2.08-1.96 (m, 1H), 1.87 (t, 2H),<br>1.62-1.52 (m, 2H),<br>1.41-1.33 (m, 6H),<br>1.17 (dd, 1H). |
| 75 | 480.3 | 2.2 |  |
| 76 | 426.27 | 2.2 |  |
| 77 | 381.3 | 2.1 | CD$_3$OD:<br>7.71 (d, 1H),<br>7.31-7.40 (m, 4H),<br>4.31 (m, 1H),<br>3.77 (m, 2H) < 3.26-3.34 (m, 4H), 2.46 (m, 2H),<br>1.50-1.95 (m, 12H),<br>1.05 (s, 9H) |

VI. Assays for Detecting and Measuring Inhibition Properties of Compounds

Functional Mobilization of Intracellular Calcium to Determine Muscarinic Receptor Activity:

CHO cells expressing muscarinic receptors ($M_1$ to $M_5$) are grown as monolayers in tissue culture flasks at 37° C. in a humidified atmosphere containing 5% $CO_2$ and passaged every 3-5 days. The growth media is Dulbecco's modified eagles medium (DMEM, Gibco Cat# 12430-054), containing 25 mM Hepes and supplemented with Fetal Bovine Serum (Hyclone, cat# SH30071.03), 0.1 mM of MEM non-essential amino acids (GIBCO, Cat# 11140-050), 1 mM MEM Sodium Pyruvate (GIBCO Cat# 11360-070) and 100 units/ml of Penicillin G and 100 μg/ml of Streptomycin (GIBCO Cat# 15140-122). The recombinant muscarinic receptor cell lines are grown under antibiotic pressure with media containing 25 μg/ml zeocin and 500 μg/ml G418 ($M_1$-CHO), 4 μg/ml puromycin, 50 μg/ml zeocin and 2.5 μg/ml blasticidin ($M_2$ and $M_4$-CHO) or 50 μg/ml zeocin and 4 μg/ml puromycin ($M_3$ and $M_5$-CHO).

Cells are harvested at 80-90% confluence using Versene (GIBCO Cat# 15040-066), collected by centrifugation and seeded 18-24 hours prior to running the calcium assay at a density of 5,000-10,000 cells/well in back-walled, clear-bottomed 384-well plates (BD Biocoat, poly-D-lysine, Cat#356663). The day of the experiment, the cells are washed with a plate washer (Bioteck Instruments, ELX 405) using bath buffer (140-mM NaCl, 4.5-mM KCl, 2-mM $CaCl_2$, 1-mM $MgCl_2$, 10-mM Hepes-Na, 10-mM Glucose, pH 7.4, with NaOH) containing 1 mM Probenecid. Next, the calcium dye Fluo-3 (25 μl/well of Fluo-3 μM at 4 μM, Molecular Probes F-1241, in Bath 1 buffer containing 1 mM Probenecid) is added to the 25 μl of Bath 1 remaining in each well after the plate wash and the dye is loaded at 37° C. in the tissue culture incubator for 60-90 min. The fluorescent dye is removed using the plate washer with Bath 1 containing 1 mM Probenecid, leaving 25 μl/well of this solution after the wash. Alternatively, cells can be loaded with the calcium indicator from Molecular Devices (Calcium 3 Assay Reagents, Cat # R7181) adding 5 μl of a 5× solution dye in Bath 1 containing 1 mM Probenecid (10 ml per dye flask cat# R7182 to generate a solution 20×) to 20 μl of the same buffer. After loading for 60 min, the experiment can be run without having to remove the dye.

Compounds are prepared at a 2× fold concentration in a 96-well plate (round bottom, Costar Corning cat# 3656), by reconstituting the pre-spotted compounds in bath 1 containing 1 mM probenecid. The final concentration DMSO is 0.5%, and the amount of DMSO is normalized across the assay plate. To determine an agonist action of the compounds on muscarinic receptors, the reconstituted compounds are added (25 μl compound/well) to the cell assay plate (containing 25 μl/well) using the multi-channel robotic system of the FLIPR 3 Instrument (Molecular Devices, Sunnyvale, Calif.). To determine a functional inhibitory-action of the compounds on muscarinic receptors, the reconstituted compounds are added (25 μl compound/well) to the assay plate and pre-incubated for 15 min prior to adding 25 μl of Carbachol at 3× the EC80 for each muscarinic subtype. Alternatively, the compounds can be co-applied simultaneously with the agonist. In both assay modes, the fluorescence is recorded for 60 sec (excitation wavelength is 488 nM and emission wavelength 540 nm) using the FLIPR 3 instrument.

The potency, efficacy and selectivity of the muscarinic compounds were evaluated by screening the compound activity across the whole family ($M_1$ to $M_5$ cells). Compounds were also screened for activity on other proteins such as other GPCRs and ion channels to determine selectivity on $M_4$ receptors.

The compounds of the present invention were found to modulate the $M_1$ and/or $M_4$ muscarinic receptors selectively over the other receptor types.

Examples of activities and efficacies of the muscarinic compounds of formulae (I, Ia, and Ib) on modulating $M_1$ and $M_4$ receptors are shown below in Table 8. The compound activity for the $M_1$ and $M_4$ is illustrated with "+++" if activity was measured to be less than 2.0 μM, "++" if activity was measured to be from 2.0 μM to 10.0 μM, "+" if activity was measured to be greater than 10.0 μM, and "−" if no data was available. The efficacy for $M_1$ and $M_4$ modulation is illustrated with "+++" if efficacy was calculated to be greater than 100%, "++" if efficacy was calculated to be from 100% to 25%, "+" if efficacy was calculated to be less than 25%, and "–" if no data was available. It should be noted that 100% efficacy is the maximum response obtained with the Carbachol control.

TABLE 8

Activities and efficacies of compounds of formulae (I, Ia, and Ib).

| Cmd No. | $M_1$ Activity | $M_4$ Activity | $M_1$ Efficacy | $M_4$ Efficacy |
|---|---|---|---|---|
| 1 | +++ | +++ | ++ | ++ |
| 2 | + | ++ | + | + |
| 3 | + | ++ | + | ++ |
| 4 | +++ | +++ | ++ | ++ |
| 5 | +++ | +++ | ++ | ++ |
| 6 | + | +++ | ++ | ++ |
| 7 | + | + | + | + |
| 8 | + | + | ++ | + |
| 9 | + | + | ++ | + |
| 10 | + | + | + | + |
| 11 | ++ | ++ | ++ | + |
| 12 | + | + | + | ++ |
| 13 | +++ | +++ | ++ | ++ |
| 14 | + | + | + | ++ |
| 15 | + | +++ | ++ | ++ |
| 16 | + | + | + | + |
| 17 | + | + | + | ++ |
| 18 | + | + | + | + |
| 19 | + | + | ++ | + |
| 20 | + | +++ | + | + |
| 21 | ++ | +++ | +++ | +++ |
| 22 | + | + | + | + |
| 23 | + | + | + | + |
| 24 | + | ++ | ++ | ++ |
| 25 | ++ | + | ++ | + |
| 26 | + | + | + | + |
| 27 | +++ | +++ | ++ | ++ |
| 28 | ++ | +++ | ++ | ++ |
| 29 | + | + | + | + |
| 30 | + | +++ | + | ++ |
| 31 | – | – | – | – |
| 32 | + | +++ | ++ | ++ |
| 33 | + | + | + | + |
| 34 | +++ | + | ++ | + |
| 35 | + | ++ | + | + |
| 36 | + | + | + | + |
| 37 | +++ | +++ | ++ | ++ |
| 38 | + | +++ | ++ | ++ |
| 39 | + | ++ | + | ++ |
| 40 | + | ++ | + | ++ |
| 41 | ++ | +++ | ++ | ++ |
| 42 | + | + | + | + |
| 43 | +++ | +++ | ++ | ++ |
| 44 | + | +++ | ++ | ++ |
| 45 | + | + | + | ++ |
| 46 | ++ | +++ | ++ | ++ |
| 47 | ++ | +++ | ++ | ++ |
| 48 | + | + | ++ | ++ |
| 49 | + | + | + | + |
| 50 | + | +++ | + | ++ |
| 51 | +++ | +++ | ++ | ++ |
| 52 | + | + | + | + |
| 53 | + | +++ | + | ++ |
| 54 | + | + | + | + |
| 55 | + | + | + | + |
| 56 | + | +++ | + | ++ |
| 57 | + | + | + | + |
| 58 | + | +++ | ++ | ++ |
| 59 | + | +++ | + | ++ |
| 60 | +++ | +++ | ++ | ++ |
| 61 | + | +++ | + | ++ |
| 62 | + | +++ | ++ | ++ |
| 63 | +++ | +++ | ++ | ++ |
| 64 | + | +++ | + | ++ |
| 65 | +++ | +++ | ++ | ++ |
| 66 | + | +++ | + | ++ |
| 67 | + | +++ | ++ | ++ |
| 68 | + | ++ | + | ++ |
| 69 | +++ | +++ | ++ | ++ |
| 70 | + | + | ++ | ++ |

TABLE 8-continued

Activities and efficacies of compounds of formulae (I, Ia, and Ib).

| Cmd No. | $M_1$ Activity | $M_4$ Activity | $M_1$ Efficacy | $M_4$ Efficacy |
|---|---|---|---|---|
| 71 | + | +++ | + | ++ |
| 72 | +++ | +++ | ++ | ++ |
| 73 | + | ++ | + | ++ |
| 74 | + | ++ | + | + |
| 75 | ++ | +++ | ++ | ++ |
| 76 | + | + | + | + |
| 77 | + | + | ++ | + |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of formula Ia:

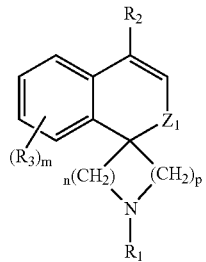

Ia or a pharmaceutically acceptable salt thereof, wherein
$R_1$ is a $C_{1-12}$ aliphatic; or
$R_1$ is a methyl, ethyl, propyl, butyl, pentyl, hexyl, heptyl, or octyl, each of which is optionally substituted with 1-3 of halo or a cycloaliphatic, a heterocycloaliphatic, an alkylsulfanyl, an alkoxy, an amino, an acyl, or combinations thereof; or
$R_1$ is a 3-8 membered monocyclic cycloaliphatic, a 7-10 membered bicyclic cycloalkyl or a 7-10 membered bicyclic cycloalkenyl; or
$R_1$ is a 3-8 membered monocyclic heterocycloaliphatic having 1-3 heteroatoms selected from N, O, and S, which is optionally substituted with 1-3 of halo, aminocarbonyl, alkoxycarbonyl, acyl, carboxy or combinations thereof; or
$R_1$ is a 7-10 membered bridged bicyclic heterocycloaliphatic, which is optionally substituted with 1-3 of halo, aminocarbonyl, alkoxycarbonyl, acyl, carboxy or combinations thereof;
$R_2$ is a straight or branched ($C_{1-10}$ aliphatic(amino))carbonyl; or
$R_2$ is a monocyclic cycloaliphaticaminocarbonyl; or
$R_2$ is hydroxycarbonyl, a straight or branched ($C_{1-8}$ aliphatic(oxy))carbonyl group, or a (heterocycloaliphatic)carbonyl;
Each $R_3$ is independently hydrogen, halo, or $C_{1-6}$ aliphatic;
$Z_1$ is a bond;
m is 0-4;

n is 2; and p is 2.

2. A compound according to claim 1, wherein $R_1$ is a $C_{1-12}$ aliphatic.

3. A compound according to claim 2, wherein $R_1$ is isopropyl, 3,3-dimethylbutyl, 2,2-dimethylbutane, tert-butyl, 3-methylbutyl, butyl, 2-ethylbutyl, propyl, butan-3-one-yl, butan-2-one-yl, but-2-yn-yl, methoxyethyl, isopentyl, or 3,7-dimethyloctyl.

4. A compound according to claim 1, wherein $R_1$ is a methyl, ethyl, propyl, butyl, pentyl, hexyl, heptyl, or octyl, each of which is optionally substituted with 1-3 of halo or a cycloaliphatic, a heterocycloaliphatic, an alkylsulfanyl, an alkoxy, an amino, an acyl, or combinations thereof.

5. A compound according to claim 4, wherein $R_1$ is selected from cyclohexylmethyl, (tetrahydro-2H-pyran-4-yl)ethyl, 4-(methyl(sulfanyl))butyl, 3,7--dimethyl-7-methoxyoctyl and (tetrahydro-2H-thiopyran-4-yl)ethyl.

6. A compound according to claim 1, wherein $R_1$ is an optionally substituted 3-8 membered monocyclic cycloaliphatic, a 7-10 membered bicyclic cycloalkyl or a 7-10 membered bicyclic cycloalkenyl.

7. A compound according to claim 6, wherein $R_1$ is cyclopropyl, cyclobutyl, cyclopentyl, cyclohexyl, cycloheptyl, cyclooctyl, bicyclo[2.1.1]hexane-yl, bicyclo[2.2.1]heptane-yl, bicyclo[2.2.2]octane-yl, bicyclo[3.1.1]heptane-yl, bicyclo[3.2.1]octane-yl, bicyclo[3.3.1]nonane-yl, bicyclo[2.1.1]hex-2-ene-yl, bicyclo[2.2.1]hept-2-ene-yl, or bicyclo[2.2.2]oct-2-ene-yl.

8. A compound according to claim 1, wherein $R_1$ is a 3-8 membered monocyclic heterocycloaliphatic having 1-3 heteroatoms selected from N, O, and S, which is optionally substituted with 1-3 of halo, aminocarbonyl, alkoxycarbonyl, acyl, carboxy or combinations thereof.

9. A compound according to claim 8, wherein $R_1$ is tetrahydrofuran-yl, tetrahydro-2H-thiopyran-yl, pyrrolidine-yl, imidazolidine-yl, 1,4-dioxane-yl, morpholine-yl, piperidine-yl, piperazine-yl, tetrahydro-2H-pyran-yl, pyrazolidine-yl, or thiomorpholine-yl, each of which is optionally substituted with 1-3 of halo, aminocarbonyl, alkoxycarbonyl, acyl, carboxy or combinations thereof.

10. A compound according to claim 9, wherein $R_1$ is piperidine-yl, which is optionally substituted with aminocarbonyl, alkoxycarbonyl, acyl, carboxy or combinations thereof.

11. A compound according to claim 1, wherein $R_1$ is a 7-10 membered bridged bicyclic heterocycloaliphatic, which is optionally substituted with 1-3 of halo, aminocarbonyl, alkoxycarbonyl, acyl, carboxy or combinations thereof.

12. A compound according to claim 11, wherein $R_1$ is 8-azabicyclo[3.2.1]octane-yl, or azabicyclo[2.2.1]heptane-yl, which is optionally substituted with 1-3 of halo, aminocarbonyl, alkoxycarbonyl, acyl, carboxy or combinations thereof.

13. A compound according to claim 1, wherein $R_2$ is a straight or branched ($C_{1-10}$ aliphatic(amino))carbonyl.

14. A compound according to claim 13, wherein $R_2$ is pent-3-ylaminocarbonyl, methylaminocarbonyl, 1-methylbutylaminocarbonyl, isopropyl aminocarbonyl, or N,N-diethylaminocarbonyl.

15. A compound according to claim 1, wherein $R_2$ is a monocyclic cycloaliphaticaminocarbonyl.

16. A compound according to claim 15, wherein $R_2$ is a cyclobutylaminocarbonyl, a cyclopentylaminocarbonyl, a cyclohexylaminocarbonyl, a cycloheptylaminocarbonyl, or a cyclooctylaminocarbonyl.

17. A compound according to claim 1, wherein $R_2$ is hydroxycarbonyl, a straight or branched ($C_{1-8}$ aliphatic(oxy)) carbonyl group, or a (heterocycloaliphatic)carbonyl.

18. A compound according to claim 17, wherein $R_2$ is hydroxycarbonyl, methoxycarbonyl, ethoxycarbonyl, propoxycarbonyl, butoxycarbonyl, isopropoxycarbonyl, tert-butoxycarbonyl or (piperidine-1-yl)carbonyl.

19. A compound according to claim 1, wherein each $R_3$ is independently hydrogen.

20. A compound according to claim 19, wherein $R_1$ is isopropyl, 3,3-dimethylbutyl, 2,2-dimethylbutane, tert-butyl, 3-methylbutyl, butyl, 2-ethylbutyl, propyl, butan-3-one-yl, butan-2-one-yl, but-2-yn-yl, methoxyethyl, isopentyl, or 3,7-dimethyloctyl.

21. A compound according to claim 19, wherein $R_1$ is selected from cyclohexylmethyl, (tetrahydro-2H-pyran-4-yl) ethyl, 4-(methyl(sulfanyl))butyl, 3,7-dimethyl-7-methoxyoctyl and (tetrahydro-2H-thiopyran-4-yl)ethyl.

22. A compound according to claim 19, wherein $R_1$ is cyclopropyl, cyclobutyl, cyclopentyl, cyclohexyl, cycloheptyl, cyclooctyl, bicyclo[2.1.1]hexane-yl, bicyclo[2.2.1]heptane-yl, bicyclo[2.2.2]octane-yl, bicyclo[3.1.1]heptane-yl, bicyclo[3.2.1]octane-yl, bicyclo[3.3.1]nonane-yl, bicyclo[2.1.1]hex-2-ene-yl, bicyclo[2.2.1]hept-2-ene-yl, or bicyclo[2.2.2] oct-2-ene-yl.

23. A compound according to claim 19, wherein $R_1$ is tetrahydrofuran-yl, tetrahydro-2H-thiopyran-yl, pyrrolidine-yl, imidazolidine-yl, 1,4-dioxane-yl, morpholine-yl, piperidine-yl, piperazine-yl, tetrahydro-2H-pyran-yl, pyrazolidine-yl, or thiomorpholine-yl, each of which is optionally substituted with 1-3 of halo, aminocarbonyl, alkoxycarbonyl, acyl, carboxy or combinations thereof.

24. A compound according to claim 19, wherein $R_1$ is 8-azabicyclo[3.2.1]octane-yl, or azabicyclo[2.2.1]heptane-yl, which is optionally substituted with 1-3 of halo, aminocarbonyl, alkoxycarbonyl, acyl, carboxy or combinations thereof.

25. A compound according to claim 19, wherein $R_2$ is pent-3-ylaminocarbonyl, methylaminocarbonyl, 1-methylbutylaminocarbonyl, isopropylaminocarbonyl, or N,N-diethylaminocarbonyl.

26. A compound according to claim 19, wherein $R_2$ is a cyclobutylaminocarbonyl, a cyclopentylaminocarbonyl, a cyclohexylaminocarbonyl, a cycloheptylaminocarbonyl, or a cyclooctylaminocarbonyl.

27. A compound according to claim 19, wherein $R_2$ is hydroxycarbonyl, methoxycarbonyl, ethoxycarbonyl, propoxycarbonyl, butoxycarbonyl, isopropoxycarbonyl, tert-butoxycarbonyl or (piperidine-1-yl)carbonyl.

28. A compound according to claim 1, wherein
$R_1$ is isopropyl, 3,3-dimethylbutyl, 2,2-dimethylbutane, tert-butyl, 3-methylbutyl, butyl, 2-ethylbutyl, propyl, butan-3-one-yl, butan-2-one-yl, but-2-yn-yl, methoxyethyl, isopentyl, 3,7-dimethyloctyl, cyclohexylmethyl, (tetrahydro-2H-pyran-4-yl)ethyl, 4-(methyl(sulfanyl)) butyl, 3,7-dimethyl-7-methoxyoctyl, (tetrahydro-2H-thiopyran-4-yl)ethyl, cyclopropyl, cyclobutyl, cyclopentyl, cyclohexyl, cycloheptyl, cyclooctyl, bicyclo[2.1.1]hexane-yl, bicyclo[2.2.1]heptane-yl, bicyclo[2.2.2]octane-yl, bicyclo[3.1.1]heptane-yl, bicyclo[3.2.1]octane-yl, bicyclo[3.3.1]nonane-yl, bicyclo[2.1.1]hex-2-ene-yl, bicyclo[2.2.1]hept-2-ene-yl, bicyclo[2.2.2]oct-2-ene-yl, tetrahydrofuran-yl, tetrahydro-2H-thiopyran-yl, pyrrolidine-yl, imidazolidine-yl, 1,4-dioxane-yl, morpholine-yl, piperidine-yl, piperazine-yl, tetrahydro-2H-pyran-yl, pyrazolidine-yl, thiomorpholine-yl, 8-azabicyclo[3.2.1]octane-yl, or azabicyclo[2.2.1]heptane-yl, wherein the tetrahydrofuran-yl, tetrahydro-2H-thiopyran-yl, pyrrolidine-yl, imidazolidine-yl, 1,4-dioxane-yl, morpholine-yl, piperidine-yl, piperazine-yl, tetrahydro-2H-pyran-yl, pyrazolidine-yl, thiomorpholine-yl, 8-azabicyclo[3.2.1]octane-yl, and azabicyclo[2.2.1]heptane-yl, are optionally substituted with 1-3 of halo, aminocarbonyl, alkoxycarbonyl, acyl, carboxy or combinations thereof;

$R_2$ is pent-3-ylaminocarbonyl, methylaminocarbonyl, 1-methylbutylaminocarbonyl, isopropylaminocarbonyl, N,N-diethylaminocarbonyl, a cyclobutylaminocarbonyl, a cyclopentylaminocarbonyl, a cyclohexylaminocarbonyl, a cycloheptylaminocarbonyl, a cyclooctylaminocarbonyl, hydroxycarbonyl, methoxycarbonyl, ethoxycarbonyl, propoxycarbonyl, butoxycarbonyl, isopropoxycarbonyl, tert-butoxycarbonyl or (piperidine-1-yl) carbonyl; and each $R_3$ is independently hydrogen.

29. A compound selected from:

1

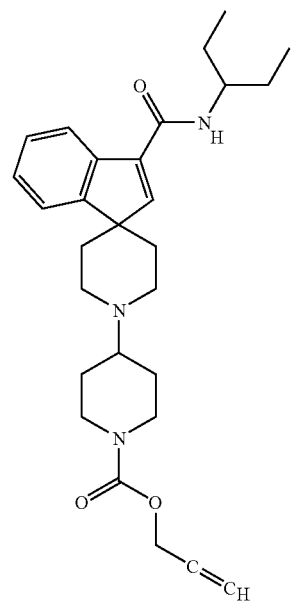

2

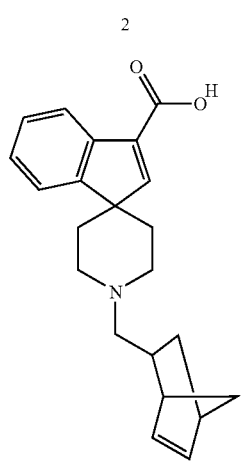

3

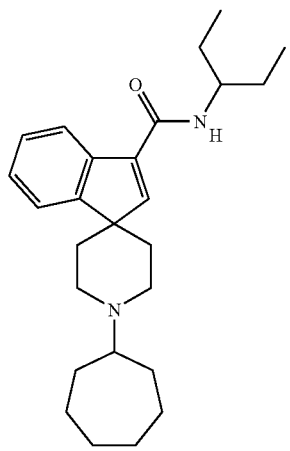

6

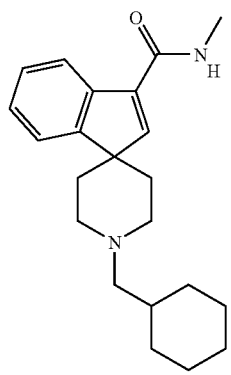

7

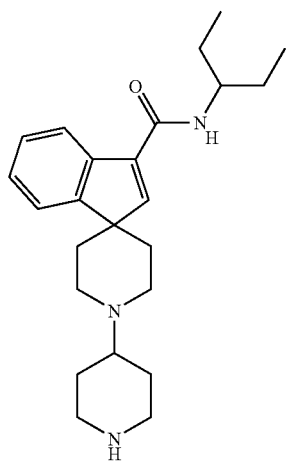

8
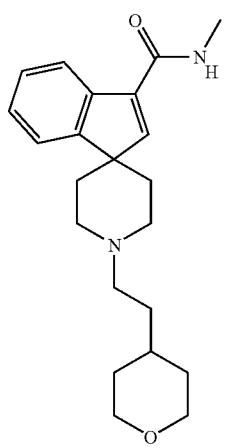
9
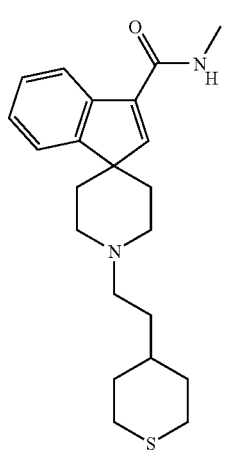
10
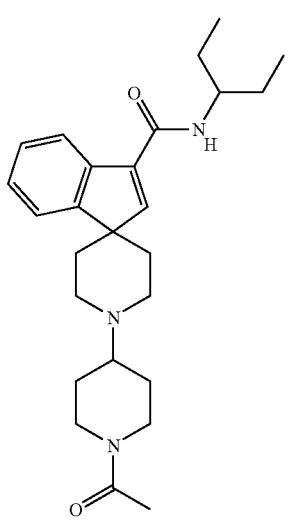
12
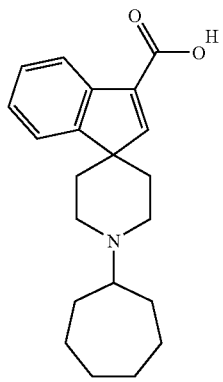
13
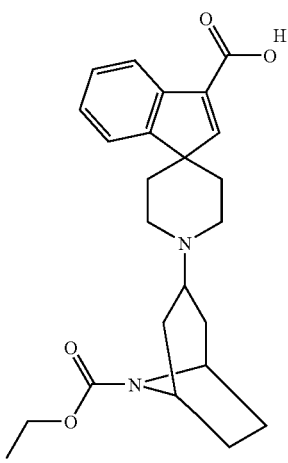
14
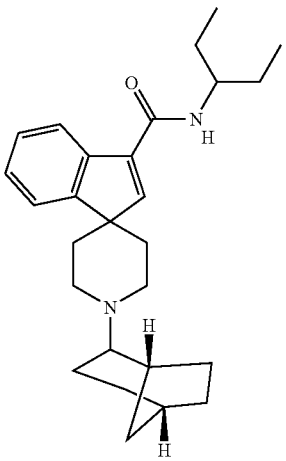

-continued
15
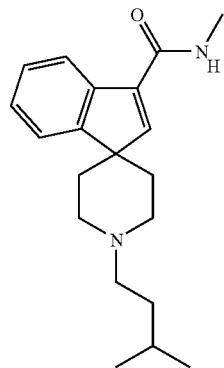
16
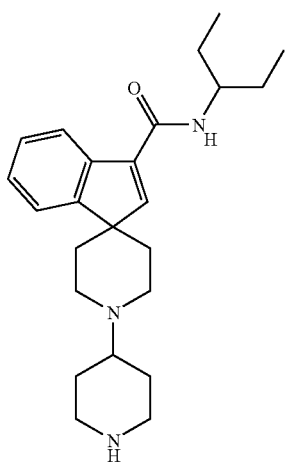
17
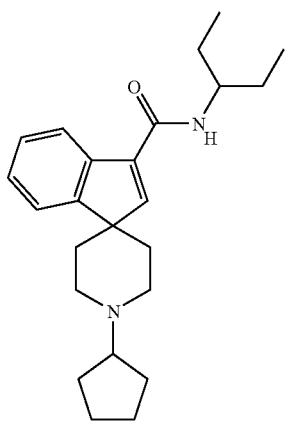
-continued
18
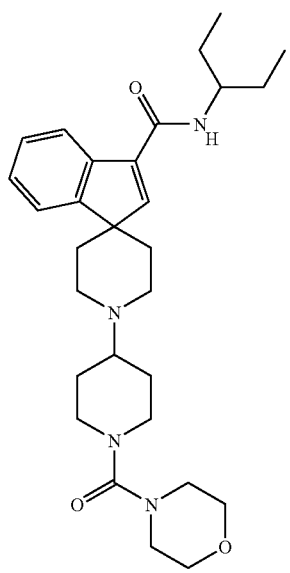
19
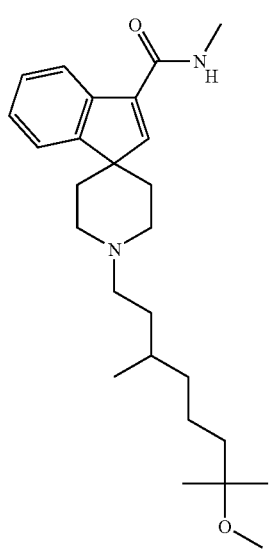
20
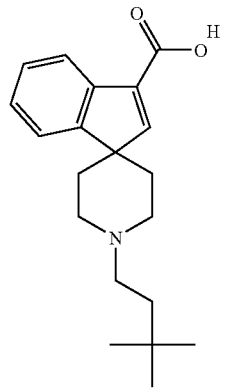

-continued
21
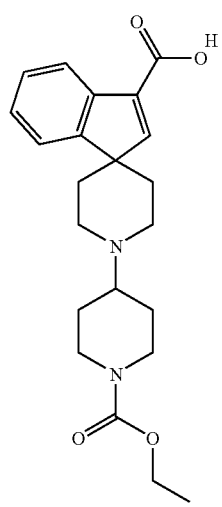
22
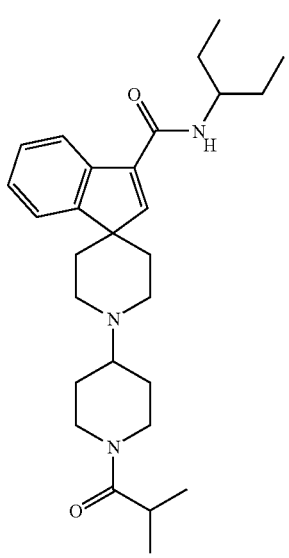
-continued
23
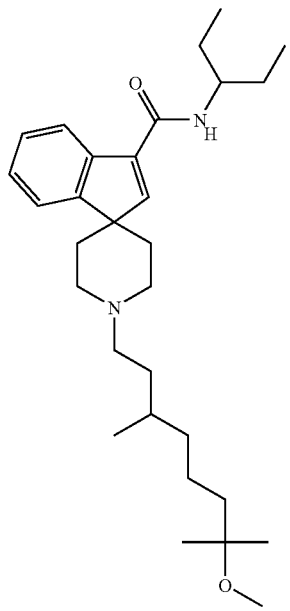
24
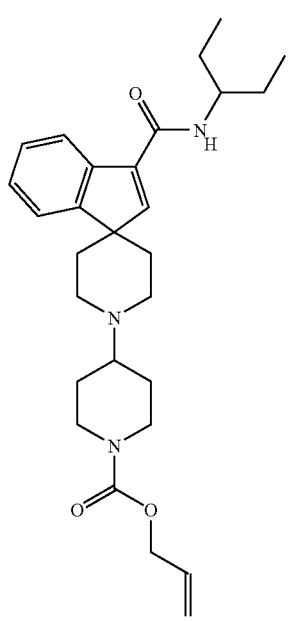

-continued
25
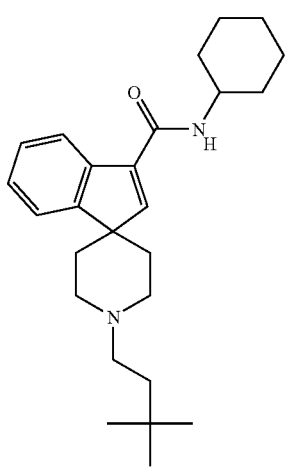
26
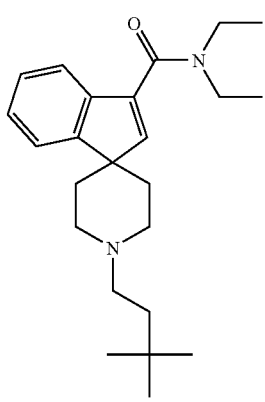
27
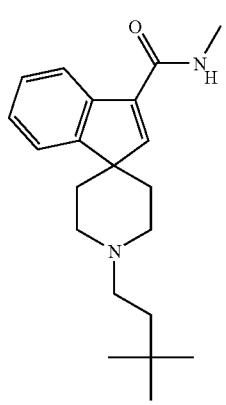
-continued
28
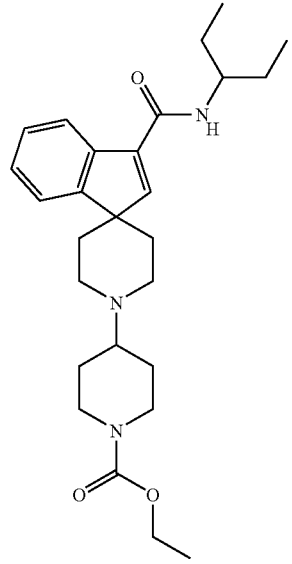
30
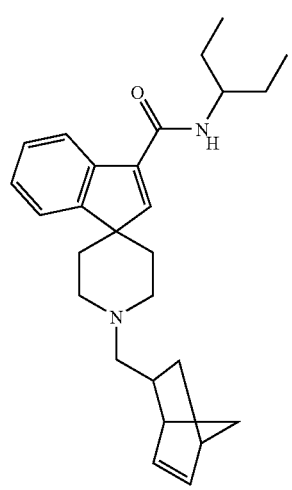
31
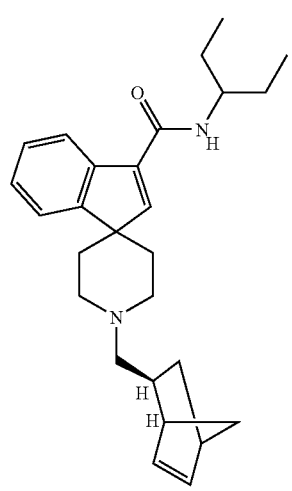

-continued
32
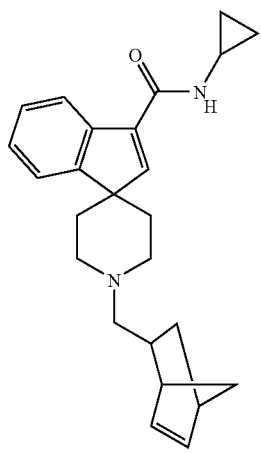
33
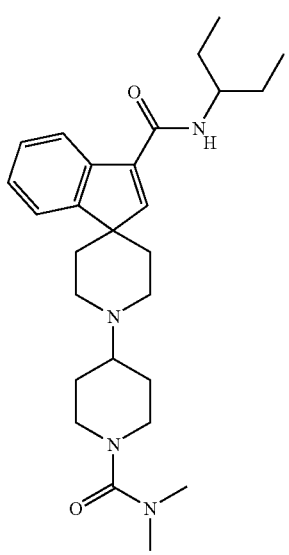
37
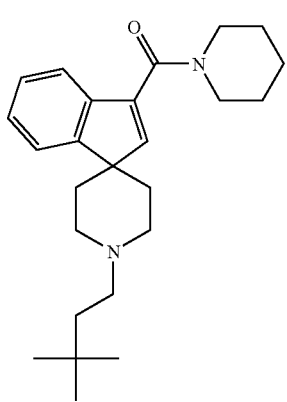
-continued
38
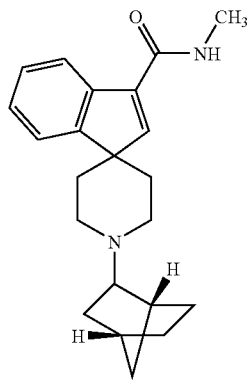
39
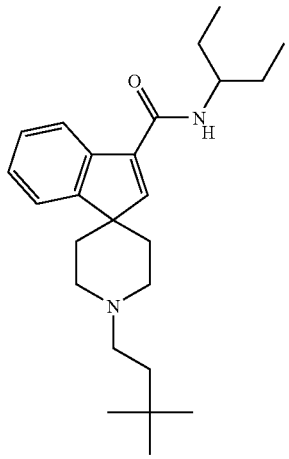
40
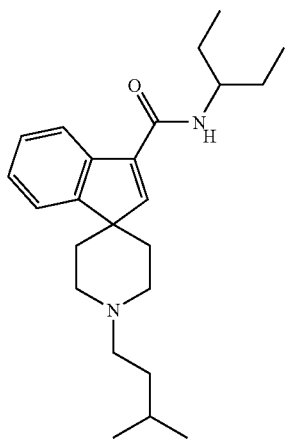

-continued
41
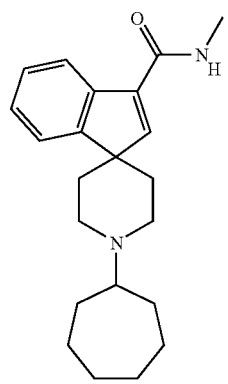
42
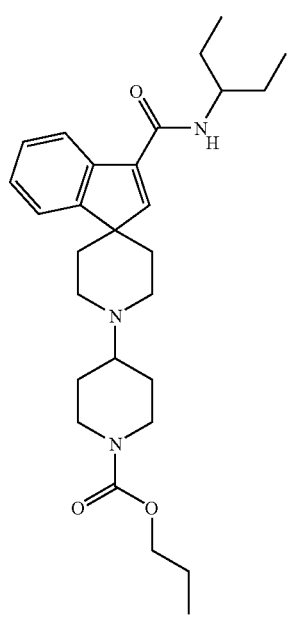
44
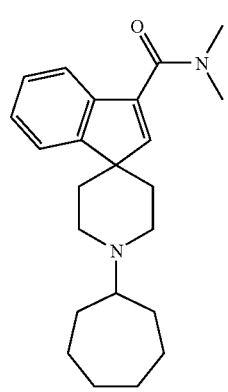
-continued
45
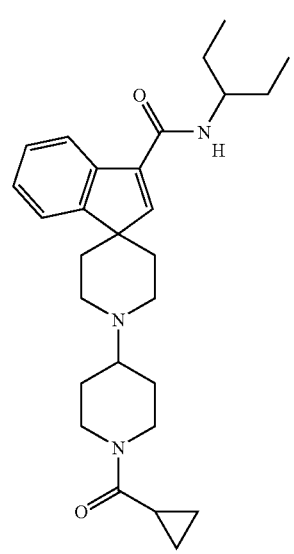
47
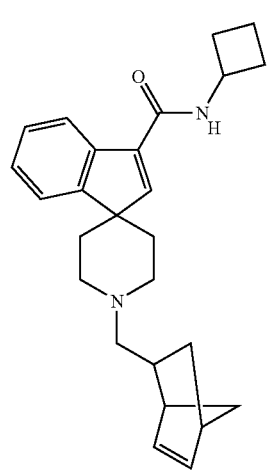
48
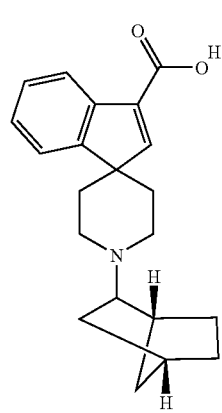

-continued
49
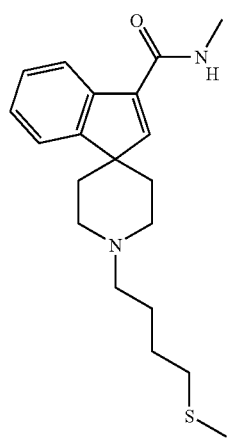
50
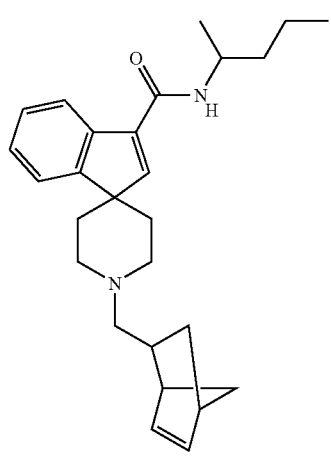
53
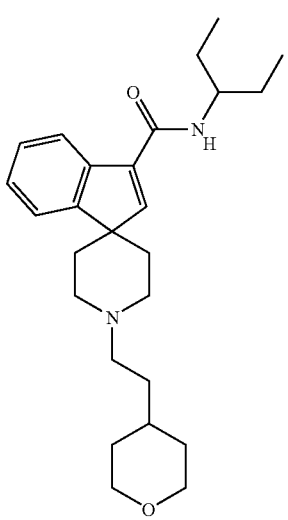
-continued
54
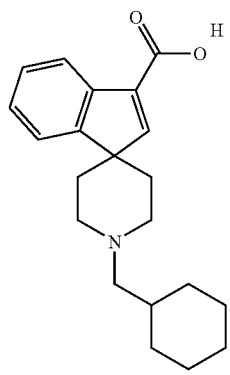
55
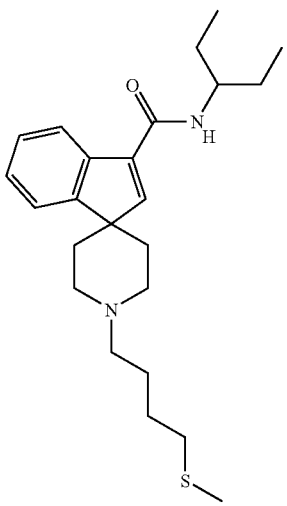
56
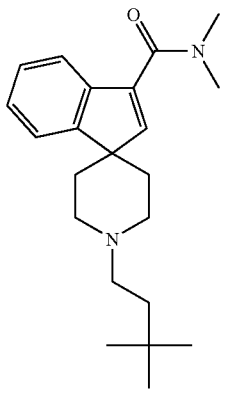

-continued
57
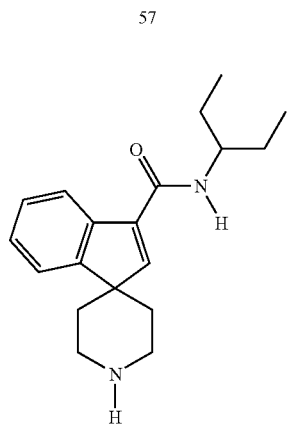
58
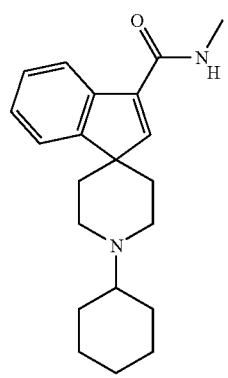
59
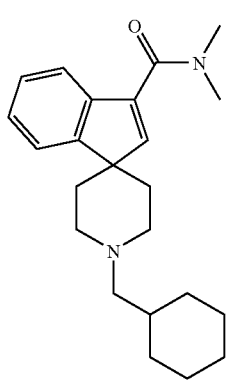
-continued
60
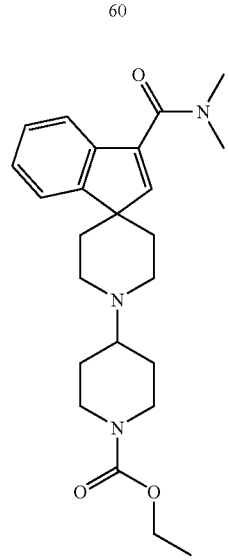
61
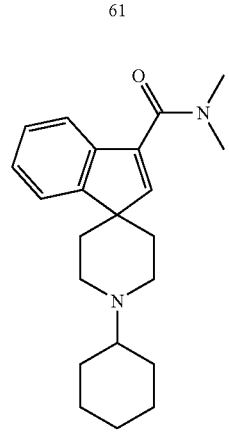
62
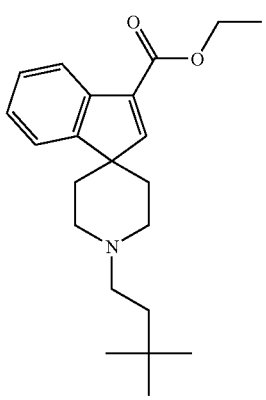

US 7,858,790 B2
| 107 | 108 |
|---|---|
| -continued | -continued |
64
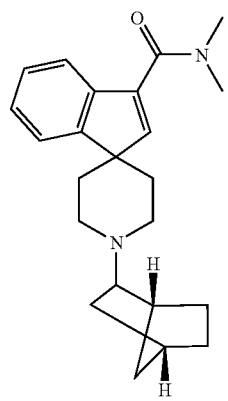
65
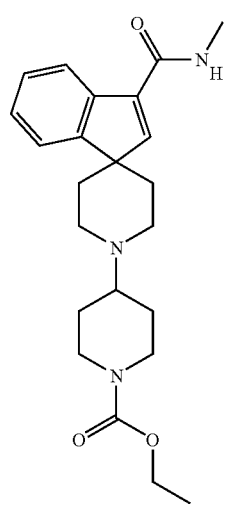
66
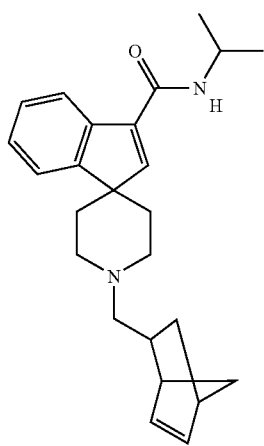
67
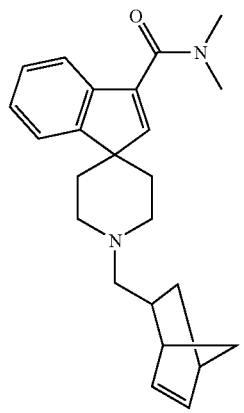
68
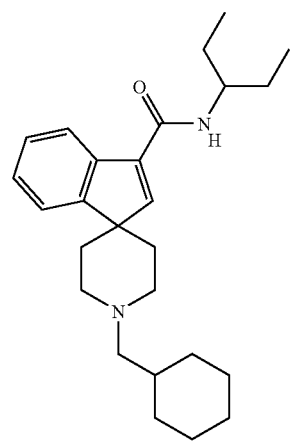
69
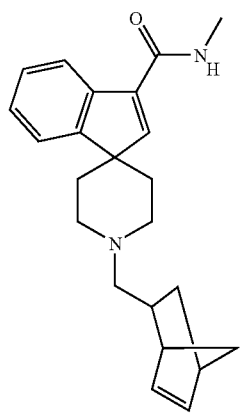

-continued
70
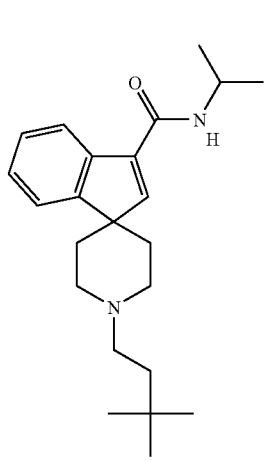
71
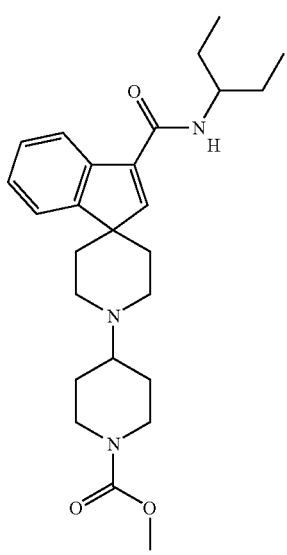
73
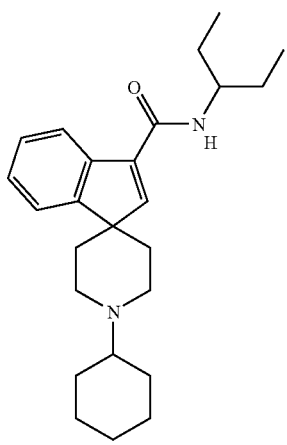
-continued
75
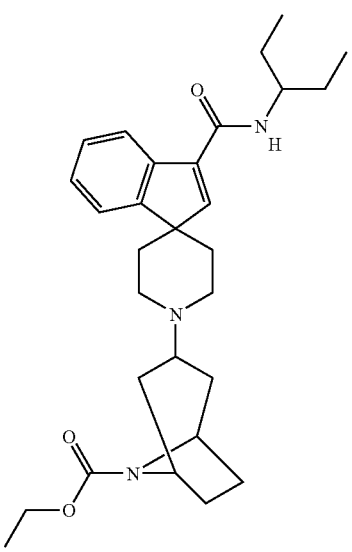
76
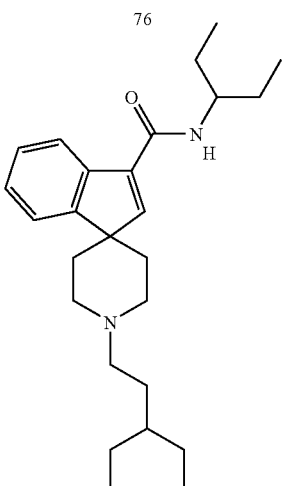
77
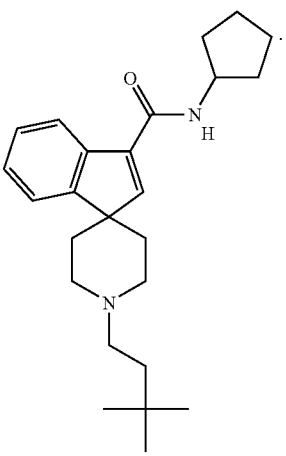
* * * * *